(12) United States Patent
Austin et al.

(10) Patent No.: US 8,198,033 B2
(45) Date of Patent: Jun. 12, 2012

(54) METHODS AND MATERIALS FOR OBSERVING APOPTOSIS

(75) Inventors: Cary D. Austin, San Carlos, CA (US); David A. Lawrence, San Francisco, CA (US); Avi Ashkenazi, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 456 days.

(21) Appl. No.: 12/308,542

(22) PCT Filed: Jun. 20, 2007

(86) PCT No.: PCT/US2007/014382
§ 371 (c)(1), (2), (4) Date: Dec. 16, 2008

(87) PCT Pub. No.: WO2007/149486
PCT Pub. Date: Dec. 27, 2007

(65) Prior Publication Data
US 2011/0244473 A1   Oct. 6, 2011

Related U.S. Application Data

(60) Provisional application No. 60/814,955, filed on Jun. 20, 2006.

(51) Int. Cl.
*G01N 33/53* (2006.01)
*G01N 33/567* (2006.01)
*G01N 33/574* (2006.01)
*G01N 33/00* (2006.01)

(52) U.S. Cl. ...... 435/7.1; 435/7.21; 435/7.23; 435/7.91; 435/7.92

(58) Field of Classification Search ........................ None
See application file for complete search history.

(56) References Cited

U.S. PATENT DOCUMENTS
2006/0019256 A1 *   1/2006   Clarke et al. ................... 435/6

FOREIGN PATENT DOCUMENTS
WO    WO00/17648    3/2000

OTHER PUBLICATIONS

PCT/US2007/014382 International Search Report and Written Opinion, Feb. 1, 2008.
Wettey et al., "Controlled Elimination of Clathrin Heavy-Chain Expression in DT40 Lymphocytes", Science, vol. 297, Aug. 30, 2002.
Hansen et al., "Stabilin-1 and stabilin-2 are both directed into the early endocytic pathway in hepatic sinusoidal endothelium via interactions with clathrin/AP-2, independent of ligand binding", Science Direct, Experimental Cell Research 303, (2005) 160-173.
Austin et al., "Death-receptor activation halts clathrin-dependent endocytosis", PNAS, Jul. 5, 2006, vol. 103.
Enari et al., "Requirement of clathrin heavy chain for p53-mediated transcription", Genes & Development, Jan. 16, 2008.

* cited by examiner

*Primary Examiner* — Peter J Reddig
(74) *Attorney, Agent, or Firm* — Gates & Cooper LLP

(57) ABSTRACT

The invention provides methods and materials for observing protein fragments generated during apoptosis in order to observe this process in mammalian cells. Embodiments of the invention can be used for example to observe apoptosis in order to examine the sensitivity of a mammalian cancer cell to apoptosis inducing agents.

9 Claims, 14 Drawing Sheets

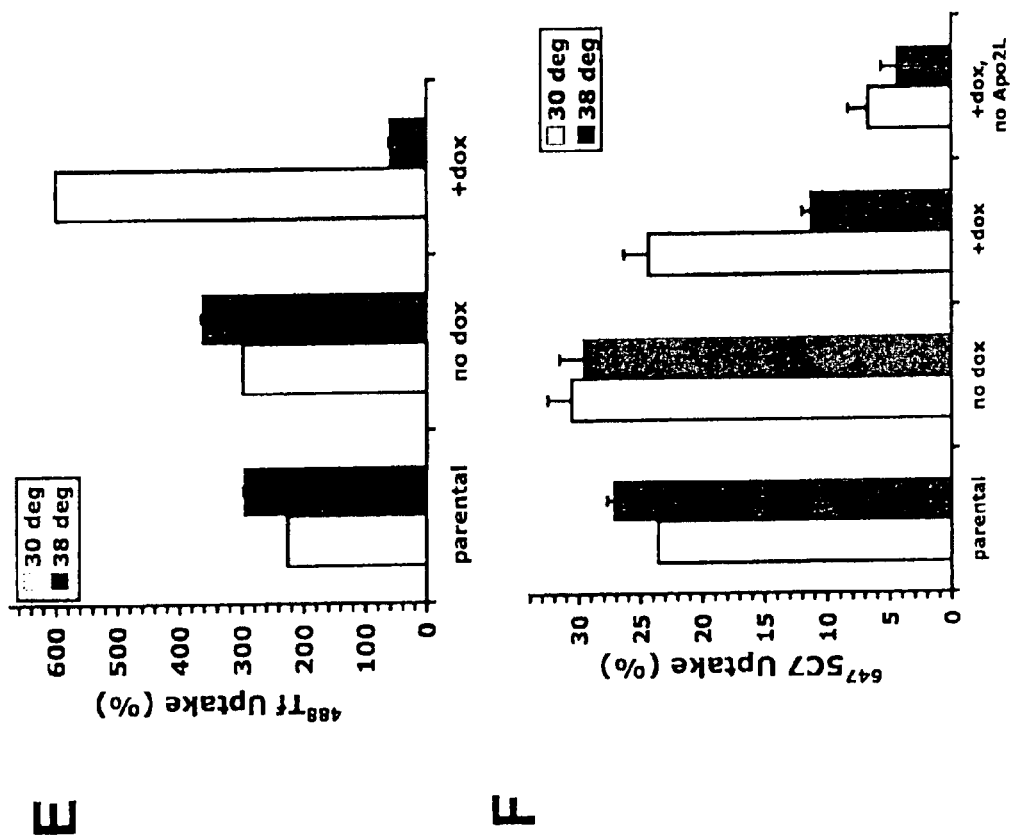

A Clip

...DVFDGPAAQPSLGPTPEEAFLSPGPEDIGPPIPEADELLNKFVCKNNGVLFENQLLQIGVKSEFRQNLG
RMYLFYGNKTSVQFQNFSPTVVHPGDLQTQLAVQTKRVAAQVDGGAQVQQVLNIECLRDFLTPPLLSVR
FRYGGAPQALTLKLPVTINKFFQPTEMAAQDFFQRWKQLSLPQQEAQKIFKANHPMDAEVTKAKLLGFG
SALLDNVDPNPENFVGAGIIQTKALQVGCLLRLEPNAQAQMYRLTLRTSKEPVSRHLCELLAQQF (residues 684 to 955 of SEQ ID NO: 1)

B

METHODS AND MATERIALS FOR OBSERVING APOPTOSIS

CROSS REFERENCE TO RELATED APPLICATIONS

This application claims the benefit of U.S. provisional patent application No. 60/814,955, filed Jun. 20, 2006, the entire contents of which are incorporated herein by reference.

FIELD OF THE INVENTION

This invention relates generally to methods for observing apoptosis in mammalian cells such as human cancer cells exposed to an apoptosis inducing agent.

BACKGROUND OF THE INVENTION

Control of cell numbers in mammals is determined, in part, by a balance between cell proliferation and cell death. One form of cell death, sometimes referred to as necrotic cell death, is typically characterized as a pathologic form of cell death resulting from some trauma or cellular injury. In contrast, there is another, "physiologic" form of cell death which usually proceeds in an orderly or controlled manner. This orderly or controlled form of cell death is often referred to as "apoptosis" (see, e.g., Barr et al., *Bio/Technology,* 12:487-493 (1994); Steller et al., *Science,* 267:1445-1449 (1995)). Apoptotic cell death naturally occurs in many physiological processes, including embryonic development and clonal selection in the immune system (Itoh et al., *Cell,* 66:233-243 (1991)).

Various molecules, such as tumor necrosis factor-α ("TNF-α"), tumor necrosis factor-β ("TNF-β" or "lymphotoxin-α"), lymphotoxin-β ("LT-β"), CD30 ligand, CD27 ligand, CD40 ligand, OX-40 ligand, 4-1BB ligand, Apo-1 ligand (also referred to as Fas ligand or CD95 ligand), Apo-2 ligand (also referred to as TRAIL), Apo-3 ligand (also referred to as TWEAK), osteoprotegerin (OPG), APRIL, RANK ligand (also referred to as TRANCE), and TALL-1 (also referred to as BlyS, BAFF or THANK) have been identified as members of the tumor necrosis factor ("TNF") family of cytokines (See, e.g., Gruss and Dower, *Blood,* 85:3378-3404 (1995); Pitti et al., *J. Biol. Chem.,* 271:12687-12690 (1996); Wiley et al., *Immunity,* 3:673-682 (1995); Browning et al., *Cell,* 72:847-856 (1993); Armitage et al. *Nature,* 357:80-82 (1992), WO 97/01633 published Jan. 16, 1997; WO 97/25428 published Jul. 17, 1997; Marsters et al., *Curr. Biol.,* 8:525-528 (1998); Simonet et al., *Cell,* 89:309-319 (1997); Chichepor-tiche et al., *Biol. Chem.,* 272:32401-32410 (1997); Hahne et al., *J. Exp. Med.,* 188:1185-1190 (1998); WO98/28426 published Jul. 2, 1998; WO98/46751 published Oct. 22, 1998; WO/98/18921 published May 7, 1998; Moore et al., *Science,* 285:260-263 (1999); Shu et al., *J. Leukocyte Biol.,* 65:680 (1999); Schneider et al., *J. Exp. Med.,* 189:1747-1756 (1999); Mukhopadhyay et al., *J. Biol. Chem.,* 274:15978-15981 (1999)). Among these molecules, TNF-α, TNF-β, CD30 ligand, 4-1BB ligand, Apo-1 ligand, Apo-2 ligand (Apo2L/TRAIL) and Apo-3 ligand (TWEAK) have been reported to be involved in apoptotic cell death. Both TNF-α and TNF-β have been reported to induce apoptotic death in susceptible tumor cells (Schmid et al., *Proc. Natl. Acad. Sci.,* 83:1881 (1986); Dealtry et al., *Eur. J. Immunol.,* 17:689 (1987)).

Additional molecules believed to be members of the TNF cytokine family are reported to be involved in apoptosis. For instance, in Pitti et al., *J. Biol. Chem.,* 271:12687-12690 (1996), a molecule referred to as Apo-2 ligand is described. See also, WO 97/25428 published Jul. 17, 1997. The full length human Apo-2 ligand is reported to be a 281 amino acid polypeptide that induces apoptosis in various mammalian cells. Other investigators have described related polypeptides referred to as TRAIL (Wiley et al., *Immunity,* 3:673-682 (1995); WO 97/01633 published Jan. 16, 1997) and AGP-1 (WO 97/46686 published Dec. 11, 1997).

Various molecules in the TNF family also have purported role(s) in the function or development of the immune system (Gruss et al., *Blood,* 85:3378 (1995)). Zheng et al. have reported that TNF-α is involved in post-stimulation apoptosis of CD8-positive T cells (Zheng et al., *Nature,* 377:348-351 (1995)). Other investigators have reported that CD30 ligand may be involved in deletion of self-reactive T cells in the thymus (Amakawa et al., Cold Spring Harbor Laboratory Symposium on Programmed Cell Death, Abstr. No. 10, (1995)). CD40 ligand activates many functions of B cells, including proliferation, immunoglobulin secretion, and survival (Renshaw et al., *J. Exp. Med.,* 180:1889 (1994)). Another recently identified TNF family cytokine, TALL-1 (BlyS), has been reported, under certain conditions, to induce B cell proliferation and immunoglobulin secretion. (Moore et al., supra; Schneider et al., supra; Mackay et al., *J. Exp. Med.,* 190:1697 (1999)).

Mutations in the mouse Fas/Apo-1 receptor or ligand genes (called lpr and gld, respectively) have been associated with some autoimmune disorders, indicating that Apo-1 ligand may play a role in regulating the clonal deletion of self-reactive lymphocytes in the periphery (Krammer et al., *Curr. Op. Immunol.,* 6:279-289 (1994); Nagata et al., *Science,* 267:1449-1456 (1995)). Apo-1 ligand is also reported to induce post-stimulation apoptosis in CD4-positive T lymphocytes and in B lymphocytes, and may be involved in the elimination of activated lymphocytes when their function is no longer needed (Krammer et al., supra; Nagata et al., supra). Agonist mouse monoclonal antibodies specifically binding to the Apo-1 receptor have been reported to exhibit cell killing activity that is comparable to or similar to that of TNF-α (Yonehara et al., *J. Exp. Med.,* 169:1747-1756 (1989)).

Induction of various cellular responses mediated by such TNF family ligands is typically initiated by their binding to specific cell receptors. Some, but not all, TNF family ligands bind to, and induce various biological activity through, cell surface "death receptors" to activate caspases, or enzymes that carry out the cell death or apoptosis pathway (Salvesen et al., *Cell,* 91:443-446 (1997). Included among the members of the TNF receptor superfamily identified to date are TNFR1, TNFR2, TACI, GITR, CD27, OX-40, CD30, CD40, HVEM, Fas (also referred to as Apo-1 or CD95), DR4 (also referred to as TRAIL-R1), DR5 (also referred to as Apo-2 or TRAIL-R2), DcR1, DcR2, osteoprotegerin (OPG), RANK. and Apo-3 (also referred to as DR3 or TRAMP) (see, e.g., Ashkenazi, *Nature Reviews,* 2:420-430 (2002); Ashkenazi and Dixit, *Science,* 281:1305-1308 (1998); Ashkenazi and Dixit, *Curr. Opin. Cell Biol,* 11:255-260 (2000); Golstein, *Curr. Biol.,* 7:750-753 (1997) Wallach, *Cytokine Reference,* Academic Press, 2000, pages 377-411; Locksley et al., *Cell,* 104:487-501 (2001); Gruss and Dower, Blood, 85:3378-3404 (1995); HohMan et al., *J. Biol. Chem.,* 264:14927-14934 (1989); Brockhaus et al., *Proc. Natl. Acad. Sci.,* 87: 3127-3131 (1990); EP 417,563, published Mar. 20, 1991; Loetscher et al., *Cell,* 61:351 (1990); Schall et al., *Cell,* 61:361 (1990); Smith et al *Science,* 248:1019-1023 (1990); Lewis al., *Proc. Natl. Acad. Sci.,* 88: 2830-2834 (1991); Goodwin et al., *Cell. Biol.,* 11:3020-3026 (1991); Stamenkovic et al., *EMBO J.,* 8:1403-1410 (1989); Mallett al., *EMBO J.,* 9:1063-1068 (1990); Anderson al., *Nature*, 390:175-179 (1997); Chicheportiche et al., *J. Biol. Chem.*, 272:32401-32410 (1997); Pan al., *Science*, 276: 111-113 (1997); Pan et al., *Science*, 277:815-818 (1997); Sheridan et al., *Science* 277: 818-821 (1997); Degli-Esposti et al., *J. Exp. Med.*, 186:1165-1170 (1997); Marsters et al., *Curr. Biol.*, 7:1003-1006 (1997); Tsuda et al., *BBRC*, 234: 137-142 (1997); Nocentini et al., *Proc. Natl. Acad. Sci.*, 94: 6216-6221 (1997); vonBulow et al., *Science*, 278:138-141 (1997)).

Most of these TNF receptor family members share the typical structure of cell surface receptors including extracellular, transmembrane and intracellular regions, while others are found naturally as soluble proteins lacking a transmembrane and intracellular domain. The extracellular portion of typical TNFRs contains a repetitive amino acid sequence pattern of multiple cysteine-rich domains (CRDs), starting from the $NH_2$-terminus.

The ligand referred to as Apo-2L or TRAIL was identified several years ago as a member of the TNF family of cytokines. (see, e.g., Wiley et al., Immunity, 3:673-682 (1995); Pitti et al., J. Biol. Chem., 271:12697-12690 (1996); WO 97/01633; WO 97/25428; U.S. Pat. No. 5,763,223 issued Jun. 9, 1998; U.S. Pat. No. 6,284,236 issued Sep. 4, 2001). The full-length native sequence human Apo2L/TRAIL polypeptide is a 281 amino acid long, Type II transmembrane protein. Some cells can produce a natural soluble form of the polypeptide, through enzymatic cleavage of the polypeptide's extracellular region (Mariani et al., J. Cell. Biol., 137:221-229 (1997)).

Crystallographic studies of soluble forms of Apo2L/TRAIL reveal a homotrimeric structure similar to the structures of TNF and other related proteins (Hymowitz et al., *Molec Cell*, 4:563-571 (1999); Cha et al., *Immunity*, 11:253-261 (1999); Mongkolsapaya et al., *Nature Structural Biology*, 6:1048 (1999); Hymowitz et al., Biochemistry, 39:633-644 (2000)). Apo2L/TRAIL, unlike other TNF family members however, was found to have a unique structural feature in that three cysteine residues (at position 230 of each subunit in the homotrimer) together coordinate a zinc atom, and that the zinc binding is important for trimer stability and biological activity. (Hymowitz et al., supra; Bodmer et al., J. Biol. Chem., 275:20632-20637 (2000)).

It has been reported in the literature that Apo2L/TRAIL may play a role in immune system modulation, including autoimmune diseases such as rheumatoid arthritis (see, e.g., Thomas et al., J. Immunol., 161:2195-2200 (1998); Johnsen et al., Cytokine, 11:664-672 (1999); Griffith et al., J. Exp. Med., 189:1343-1353 (1999); Song et al., J. Exp. Med., 191: 1095-1103 (2000)).

Soluble forms of Apo2L/TRAIL have also been reported to induce apoptosis in a variety of cancer cells, including colon, lung, breast, prostate, bladder, kidney, ovarian and brain tumors, as well as melanoma, leukemia, and multiple myeloma (see, e.g., Wiley et al., supra; Pitti et al., supra; U.S. Pat. No. 6,030,945 issued Feb. 29, 2000; U.S. Pat. No. 6,746, 668 issued Jun. 8, 2004; Rieger et al., FEBS Letters, 427:124-128 (1998); Ashkenazi et al., J. Clin. Invest., 104:155-162 (1999); Walczak et al., Nature Med., 5:157-163 (1999); Keane et al., Cancer Research, 59:734-741 (1999); Mizutani et al., Clin. Cancer Res., 5:2605-2612 (1999); Gazitt, Leukemia, 13:1817-1824 (1999); Yu et al., Cancer Res., 60:2384-2389 (2000); Chinnaiyan et al., Proc. Natl. Acad. Sci., 97:1754-1759 (2000)). In vivo studies in murine tumor models further suggest that Apo2L/TRAIL, alone or in combination with chemotherapy or radiation therapy, can exert substantial anti-tumor effects (see, e.g., Ashkenazi et al., supra; Walczak et al., supra; Gliniak et al., Cancer Res., 59:6153-6158 (1999); Chinnaiyan et al., supra; Roth et al., Biochem. Biophys. Res. Comm., 265:1999 (1999); PCT Application US/00/15512; PCT Application US/01/23691). In contrast to many types of cancer cells, most normal human cell types appear to be resistant to apoptosis induction by certain recombinant forms of Apo2L/TRAIL (Ashkenazi et al., supra; Walczak et al., supra). Jo et al. has reported that a polyhistidine tagged soluble form of Apo2L/TRAIL induced apoptosis in vitro in normal isolated human, but not non-human, hepatocytes (Jo et al., Nature Med., 6:564-567 (2000); see also, Nagata, Nature Med., 6:502-503 (2000)). It is believed that certain recombinant Apo2L/TRAIL preparations may vary in terms of biochemical properties and biological activities on diseased versus normal cells, depending, for example, on the presence or absence of tag molecule, zinc content, and % trimer content (See, Lawrence et al., Nature Med., Letter to the Editor, 7:383-385 (2001); Qin et al., Nature Med., Letter the Editor, 7:385-386 (2001)).

Apo2L/TRAIL has been found to bind at least five different receptors. At least two of the receptors which bind Apo2L/TRAIL contain a functional, cytoplasmic death domain. One such receptor has been referred to as "DR4" (and alternatively as TR4 or TRAIL-R1) (Pan et al., *Science*, 276:111-113 (1997); see also WO98/32856 published Jul. 30, 1998; WO99/37684 published Jul. 29, 1999; WO 00/73349 published Dec. 7, 2000; US 2003/0036168 published Feb. 20, 2003; U.S. Pat. No. 6,433,147 issued Aug. 13, 2002; U.S. Pat. No. 6,461,823 issued Oct. 8, 2002, and U.S. Pat. No. 6,342, 383 issued Jan. 29, 2002).

Another such receptor for Apo2L/TRAIL has been referred to a DR5 (it has also been alternatively referred to as Apo-2; TRAIL-R. or TRAIL-R2, TR6, Tango-63, hAPO8, TRICK2 or KILLER) (see, e.g., Sheridan et al., *Science*, 277:818-821 (1997), Pan et al., *Science*, 277:815-818 (1997), WO98/ 51793 published Nov. 19,199 WO98/41629 published Sep. 24, 1998; Screaton et al., *Curr. Biol.*, 7:693-696 (1997); Walcak et al., *EMBO J.*, 16:5386-5387 (1997); Wu et al., *Nature Genetics*, 17:141-143 (1997); WO98/35986 published Aug. 20, 1998; EP870,827 published Oct. 14, 1998; WO98/46643 published Oct. 22, 1998; WO99/02653 published Jan. 21, 1999; WO99/09165 published Feb. 25, 1999; WO99/11791 published Mar. 11, 1999; WO 03/042367 published May 22, 2003; WO 02/097033 published Dec. 5, 2002; WO 03/038043 published May 8, 2003; US 2002/0072091 published Aug. 13, 2002; US 2002/0098550 published Dec. 7, 2001; U.S. Pat. No. 6,313,269 issued Dec. 6, 2001; US 2001/ 0010924 published Aug. 2, 2001; US 2003/01255540 published Jul. 3, 2003; US 2002/0160446 published Oct. 31, 2002, US 2002/0048785 published Apr. 25, 2.002; US 2004/ 0141952 published Jul. 21, 2004; US 2005/0129699 published Jun. 16, 2005; US 2005/0129616 published Jun. 16, 2005; U.S. Pat. No. 6,342,369 issued February, 2002; U.S. Pat. No. 6,569,642 issued May 27, 2003, U.S. Pat. No. 6,072, 047 issued Jun. 6, 2000, U.S. Pat. No. 6,642,358 issued Nov. 4, 2003; U.S. Pat. No. 6,743,625 issued Jun. 1, 2004). Like DR4, DR5 is reported to contain a cytoplasmic death domain and be capable of signaling apoptosis upon ligand binding (or upon binding a molecule, such as an agonist antibody, which mimics the activity of the ligand). The crystal structure of the complex formed between Apo-2L/TRAIL and DR5 is described in Hymowitz al., *Molecular Cell*, 4:563-571 (1999). Another identified death domain-containing receptor is termed DR6, (Pan et al., *FEBS Letters*, 431:351-356 (1998)).

Upon ligand binding, both DR4 and DR5 can trigger apoptosis independently by recruiting and activating the apoptosis initiator, caspase-8, through the death-domain-containing adaptor molecule referred to as FADD/Mortl (Kischkel et 1

*Immunity*, 12:611-620 (2000); Sprick et al., *Immunity*, 12:599-609 (2000); Bodmer *Nature Cell Biol.*, 2:241-243 (2000)).

Apo2L/TRAIL has been reported to also bind those receptors referred to as DcR1, DcR2 and OPG, which believed to function as inhibitors, rather than transducers of signaling (see., e.g., DCR1 (also referred as TRID, LIT or TRAIL-R3) (Pan et al., *Science*, 276:111-113 (1997); Sheridan et al., *Science*, 277:818-821 (1997); McFarlane et al., *J. Biol. Chem.*, 272:25417-25420 (1997); Schneider et al., *FEES Letters*, 416:329-334 (1997); Degli-Esposti et al., *J. Exp. Med.*, 186:1165-1170 (1997); and Mongkolsapaya et al., *J. Immunol.*, 160:3-6 (1998); DCR2 (also called TRUNDD or TRAIL-R4) (Marsters et al., *Curr. Biol.*, 7:1003-1006 (1997); Pan et al., *FEES Letters*, 424:41-45 (1998); Degli-Esposti et al., *Immunity*, 7:813-820 (1997)), and OPG (Simonet et al., supra). In contrast to DR4 and DR5, the DcR1 and DcR2 receptors do not signal apoptosis.

Certain antibodies which bind to the DR4, DR5 and/or Fas receptors have been reported in the literature. For example, anti-DR4 antibodies directed to the DR4 receptor and having agonistic or apoptotic activity in certain mammalian cells are described in, e.g., WO 99/37684 published Jul. 29, 1999; WO 00/73349 published Jul. 12, 2000; WO 03/066661 published Aug. 14, 2003. See, also, e.g., Griffith et al., *J. Immunol.*, 162:2597-2605 (1999); Chuntharapai et al., *J. Immunol.*, 166: 4891-4898 (2001); WO 02/097033 published Dec. 2, 2002; WO 03/042367 published May 22, 2003; WO 03/038043 published May 8, 2003; WO 03/037913 published May 8, 2003; US 2003/0073187 published Apr. 17, 2003; US 2003/0108516 published Jun. 12, 2003. Certain anti-DR5 antibodies have likewise been described, see, e.g., WO 98/51793 published Nov. 8, 1998; Griffith et al., *J. Immunol.*, 162:2597-2605 (1999); Ichikawa et al., *Nature . . . Med.*, 7:954-960 (2001); Hylander et al., "An Antibody to DR5 (TRAIL-Receptor 2) Suppresses the Growth of Patient Derived Gastrointestinal Tumors Grown in SCID mice", Abstract, 2d International Congress on Monoclonal Antibodies in Cancers, Aug. 29-Sep. 1, 2002, Banff, Alberta, Canada; WO 03/038043 published May 8, 2003; WO 03/037913 published May 8, 2003; US 2003/0180296 published Sep. 25, 2003. In addition, certain antibodies having cross-reactivity to both DR4 and DR5 receptors have been described (see, e.g., U.S. Pat. No. 6,252,050 issued Jun. 26, 2001). Agonist anti-Fas antibodies which induce apoptosis of target cells expressing Fas, include, but are not limited to, MAbs M2 and M3 (IgG; Alderson et al., 1995, J. Exp. Med. 181:71-77); anti-Fas MAb (IgM; Yonehara et al., 1989, J. Exp. Med. 169:1747-1756); MAb CH11 (IgM; Alderson et al., 1994, Int. Immunol. 6:1799-806); and anti-APO-1 (IgG; Dhein et al., 1992, J. Immunol., 149:3166-3173).

Apoptosis plays crucial roles in the development and homeostasis of multicellular organisms (see, e.g., Danial, N. N. et. al., *Cell* 116, 205-19 (2004)). Two major signaling mechanisms, the cell-intrinsic and -extrinsic pathways, control apoptosis induction (see, e.g., Strasser, A., et. al., *Annu Rev Biochem* 69, 217-45 (2000)). These pathways activate cysteine proteases, called caspases, which cleave various cellular proteins that are essential for cell integrity. Caspases recognize specific tetrapeptide sequences containing aspartate and cleave the adjacent peptide bond (see, e.g., Thornberry, N. A. et. al., *Science* 281, 1312-6 (1998)). Activation of the cell-extrinsic pathway occurs in response to ligands such as Fas ligand (FasL) and Apo2 ligand/TNF-related apoptosis-inducing ligand (Apo2L/TRAIL), through their respective cell surface 'death receptors' Fas (Apo1/CD95) and DR4 or DR5 (see, e.g., Nagata, S. *Cell* 88, 355-65 (1997) and LeBlanc, H. N. et. al., *Cell Death Differ* 10, 66-75 (2003)). Ligand binding triggers recruitment of the adaptor FADD (Fas-associated 'death' domain) to a death domain within the receptor's cytoplasmic tail. FADD recruits the initiator protease caspase-8 to form the 'death-inducing signaling complex' (DISC) (see, e.g., Kischkel, F. C. et al. *Embo J* 14, 5579-88 (1995)). Proximity of caspase-8 molecules in the DISC stimulates enzymatic activity, resulting in self-processing (see, e.g., Boatright, K. M. et al. *Mol Cell* 11, 529-41 (2003)). Cleaved caspase-8 then releases from the DISC to the cytoplasm and proteolytically activates effector caspases such as caspase-3 and -7. In certain cell types DR stimulation generates strong caspase-8 activity, which robustly activates effector caspases and commits the cell to apoptosis (see, e.g., Scaffidi, C., et. al., *J Biol Chem* 274, 1541-8 (1999)). Other cell types require signal amplification by the intrinsic pathway: caspase-8 cleaves the Bcl-2 homology domain 3 (BH3)-only protein Bid, which engages the intrinsic pathway through the multi-BH domain proteins Bax and Bak, enhancing effector-caspase activation and apoptosis (see, e.g., Danial, N. N. et. al., *Cell* 116, 205-19 (2004) and Strasser, A., et. al., *Annu Rev Biochem* 69, 217-45 (2000)).

Apoptosis is commonly characterized by condensation and margination of nuclear chromatin, and fragmentation of nuclear structure into so-called apoptotic bodies. This apoptotic morphology can be observed using conventional stains, dyes which selectively accumulate in nuclei such as propidium iodide or Hoechst 33258, or by electron microscopy. Internucleosomal fragmentation of DNA which is often linked to, but is not diagnostic for, cell death by apoptosis is also used to identify and quantify apoptosis.

SUMMARY OF THE INVENTION

Applicants have identified protein fragments generated in cells undergoing apoptosis which can be used as biomarkers of apoptotic cell death. Embodiments of the invention provide methods and materials for observing these protein fragments in order to, for example, observe apoptotic cell death in mammalian cells exposed to one or more apoptosis inducing agents. In an illustrative embodiment of the invention, these biomarkers of apoptosis are observed in human cancer cells order to examine the efficacy of a therapy comprising the administration of an apoptosis inducing agent such as Apo2L/TRAIL, FasL or an Apo2L/TRAIL or FasL agonist.

Applicants invention has a number of embodiments. One embodiment of the invention is a method of detecting apoptosis in a mammalian cell by contacting components of the cell with an antibody that binds to a protein fragment generated during apoptosis, wherein the antibody binds to a protein fragment of AP2-α (SEQ ID NO: 1), clathrin heavy chain (SEQ ID NO: 2), AP1/2β (SEQ ID NO: 3) or dynamin (SEQ ID NO: 4); determining the amount of the antibody which binds to the protein fragment generated during apoptosis; and comparing the amount of antibody bound in this step with the amount of antibody which binds to the protein fragment in a mammalian cell free of apoptosis, wherein if this amount is greater than the amount in the cell free of apoptosis, then apoptosis is detected. Optionally, the mammalian cell examined by this method is a human colon, colorectal, lung, breast, prostate, bladder, kidney, ovarian, brain, melanoma, leukemia or myeloma cancer cell.

As described in detail below, the methods of the invention can be used to observe apoptosis initiated by a number of different cellular receptors. In some embodiments of this method, apoptosis in the cell is initiated through Death Receptor 4 (SEQ ID NO: 5) or Death Receptor 5 (SEQ ID NO: 6), for example by contacting the cell with APO2L/ TRAIL (SEQ ID NO: 7) or an antibody which binds Death Receptor 4 (SEQ ID NO: 5) or Death Receptor 5 (SEQ ID NO: 6). In other embodiments of the invention, apoptosis in the cell is initiated through Fas (SEQ ID NO: 8), for example by contacting the cell with FasL (SEQ ID NO: 9) or an antibody which bind Fas.

The methods of the invention can further be adapted for use in a number of contexts. For example, these methods of observing apoptosis can be used to assess the sensitivity of a cell to Apo2L/TRAIL (SEQ ID NO: 7) or an antibody which binds Death Receptor 4 (SEQ ID NO: 5) or Death Receptor 5 (SEQ ID NO: 6). In a specific illustrative embodiment of the invention, these methods can be used to assess the efficacy of a therapy comprising the administration of Apo2L/TRAIL (SEQ ID NO: 7) or an antibody which binds Death Receptor 4 (SEQ ID NO: 5) or Death Receptor 5 (SEQ ID NO: 6). Similarly, other embodiments of the invention can be used to examine the sensitivity of the cell to FasL (SEQ ID NO: 9) or an antibody which binds Fas, for example to assess the efficacy of a therapy comprising the administration of FasL (SEQ ID NO: 9) or an antibody which binds Fas.

As discussed in detail below, the methods of the invention can observe the apoptotic fragmentation of a number of different proteins within a cell using any one of a variety of techniques known in the art such as immunoassays using antibodies directed to one or more of these apoptotic fragments. For example, certain embodiments of the invention antibody binds to a protein fragment of AP2-α (SEQ ID NO: 1), for example a fragment of about 64 kDa or 33 kDa. In some embodiments of the invention, the protein fragment of AP2α bound by the antibody comprises DVFD residues 684 to 687 of SEQ ID NO: 1 or GPAA residues 688 to 691 of SEQ ID NO: 1. Other embodiments of the invention can use an antibody that binds to a protein fragment of clathrin heavy chain (SEQ ID NO: 2). Other embodiments of the invention can use an antibody that binds to a protein fragment of AP1/2β (SEQ ID NO: 3). Other embodiments of the invention can use an antibody that binds a protein fragment of dynamin (SEQ ID NO: 4).

Certain embodiments of the invention are tailored to examine a specific type of apoptotic activity and/or apoptosis in a specific physiological context. For example, embodiments of the invention can be used to observe apoptosis in a mammalian cell mediated by Death Receptor 4 (SEQ ID NO: 5), Death Receptor 5 (SEQ ID NO: 6) or Fas (SEQ ID NO: 8). Typically such methods include exposing the cell to a Death Receptor 4, Death Receptor 5 or Fas ligand; examining the cell exposed to the ligand for the presence of a protein fragment of AP2-α (SEQ ID NO: 1), clathrin heavy chain (SEQ ID NO: 2), AP1/2β (SEQ ID NO: 3) or dynamin (SEQ ID NO: 4); comparing the amount of protein fragment in the cell with the amount of protein fragment in a control cell not exposed to the ligand; wherein apoptosis is observed when the amount of protein fragment present in the cell exposed to the ligand is greater than the amount of protein fragment in the control cell not exposed to the ligand. Typically in such methods, the Death Receptor 4, Death Receptor 5 or Fas ligand is Apo2L/ TRAIL (SEQ ID NO: 7), an antibody which binds Death Receptor 4 or Death Receptor 5, FasL (SEQ ID NO: 9) or an antibody which bind Fas.

Other embodiments of the invention include observing the sensitivity of a mammalian cell to Apo2L/TRAIL (SEQ ID NO: 7) or FasL (SEQ ID NO: 8) induced apoptosis by exposing the mammalian cell to Apo2L/TRAIL or FasL; examining the cell exposed to Apo2L/TRAIL or FasL for the presence of a protein fragment of AP2-α (SEQ ID NO: 1), clathrin heavy chain (SEQ ID NO: 2), AP1/2β (SEQ ID NO: 3) or dynamin (SEQ ID NO: 4); comparing the amount of protein fragment in the mammalian cell with the amount of protein fragment in a control mammalian cell not exposed to Apo2L/TRAIL or FasL; wherein the mammalian cell is observed to be sensitive to Apo2L/TRAIL or FasL mediated apoptosis if the amount of protein fragment present in the mammalian cell exposed to Apo2L/TRAIL or FasL is greater than the amount of protein fragment in the control mammalian cell not exposed to Apo2L/TRAIL or FasL.

Embodiments of the invention also provide articles of manufacture and kits which include antibodies which bind a protein fragment of AP2-α (SEQ ID NO: 1), clathrin heavy chain (SEQ ID NO: 2), AP1/2β (SEQ ID NO: 3) or dynamin (SEQ ID NO: 4). An illustrative embodiment is a kit for characterizing a mammalian cell, the kit comprising: a first antibody that binds a protein fragment of AP2-α (SEQ ID NO: 1), clathrin heavy chain (SEQ ID NO: 2), AP1/2β (SEQ ID NO: 3) or dynamin (SEQ ID NO: 4), a second antibody that binds a protein fragment of AP2-α (SEQ ID NO: 1), clathrin heavy chain (SEQ ID NO: 2), AP1/2β (SEQ ID NO: 3) or dynamin (SEQ ID NO: 4); wherein the first and second antibodies do not bind the same epitope (and optionally do not bind the same protein); a container for (a) and (b); and instructions for using the kit.

BRIEF DESCRIPTION OF THE DRAWINGS

FIG. 2 shows the involvement of different caspases in cleavage of AP2α and CHC. (a) BJAB cells were treated with the pan-caspase inhibitor zVAD-fmk (20 μM, 30 min) followed by crosslinked Apo2L/TRAIL (1 μg/mL) and analyzed by immunoblot for processing of caspase-8, caspase-3, AP2α and CHC. Open arrows indicate cleavage products and solid arrows indicate full-length proteins. (b-d) $Bax^{-/-}$ or $Bax^{+/-}$ HCT116 cells or caspase-3-deficient MCF-7 cells were treated with Apo2L/TRAIL and analyzed as in a.

DETAILED DESCRIPTION OF THE INVENTION

The techniques and procedures described or referenced herein are generally well understood and commonly employed using conventional methodology by those skilled in the art. As appropriate, procedures involving the use of commercially available kits and reagents are generally carried out in accordance with manufacturer defined protocols and/or parameters unless otherwise noted. Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. In addition, certain abbreviations are used herein including: 488—: Alexa-488 conjugated; 647—: Alexa-647 conjugated; Apo2L/TRAIL: Apo2 ligand/TNF-related apoptosis-inducing ligand; BSA: bovine serum albumin; DR: death receptor; PBS: phosphate buffered saline; Tf: transferrin; and zVAD-fmk: N-benzyloxycarbonyl-Val-Ala-Asp-fluoromethylketone.

I. Definitions

The terms "apoptosis" and "apoptotic activity" are used in a broad sense and refer to the orderly or controlled form of cell death in mammals that is typically accompanied by one or more characteristic cell changes, including condensation of cytoplasm, loss of plasma membrane microvilli, segmentation of the nucleus, degradation of chromosomal DNA or loss of mitochondrial function. This activity can be determined and measured using a number of techniques known in the art, for instance, by cell viability assays, FACS analysis or DNA electrophoresis, and more specifically by binding of annexin V, fragmentation of DNA, cell shrinkage, dilation of endoplasmatic reticulum, cell fragmentation, and/or formation of membrane vesicles (called apoptotic bodies).

Figure 1:
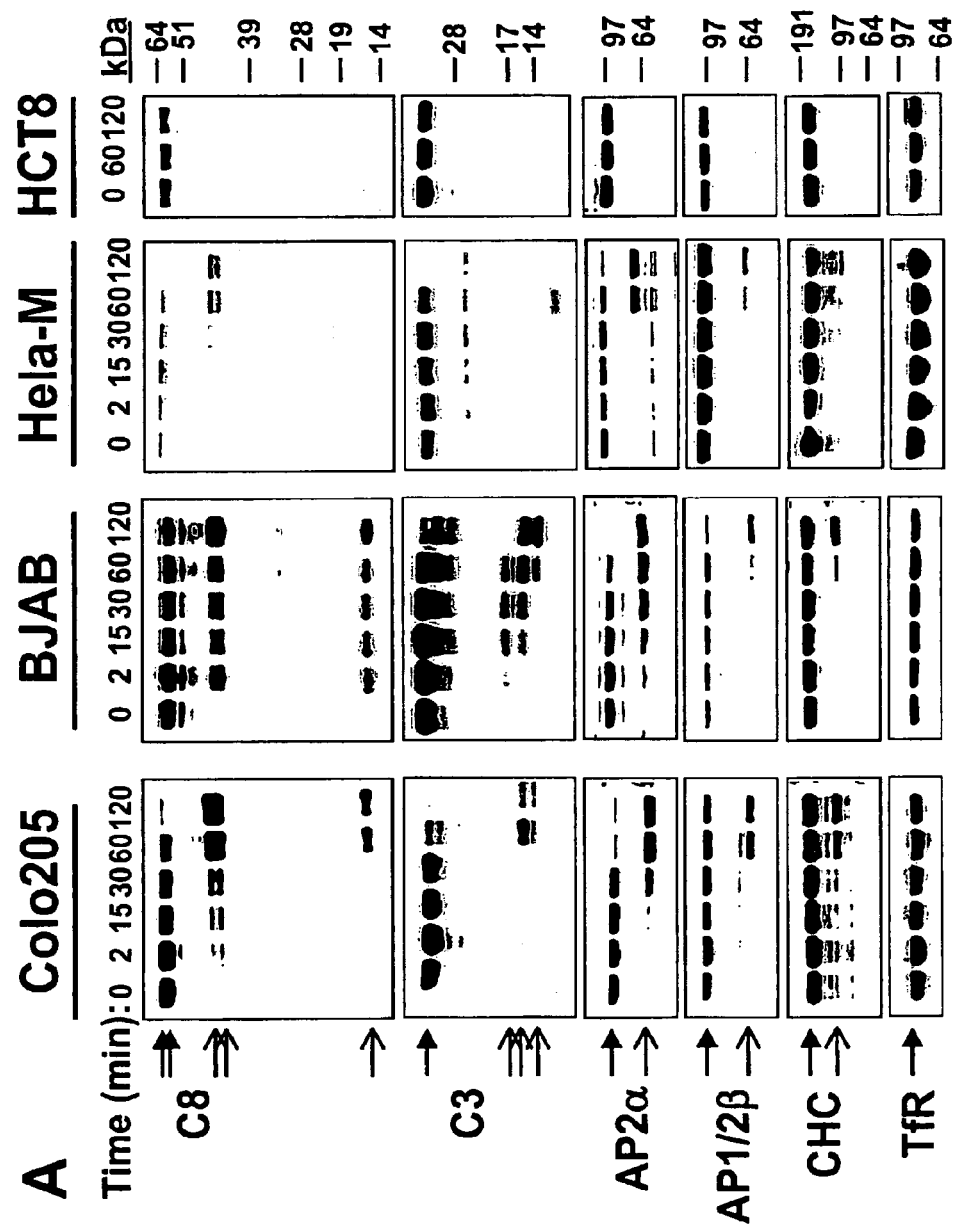
FIG. 1 shows that Apo2L/TRAIL induces selective cleavage of the clathrin-dependent endocytosis machinery. (a) Cells were treated at 37° C. with either trimeric Apo2L/ TRAIL (Colo205, HCT8) or antibody-crosslinked, tagged Apo2L/TRAIL (BJAB, HeLa-M) and cell lysates were analyzed by immunoblot for cleavage of caspase-8 (C8), caspase-3 (C3), adaptin (AP)2α, AP1/2β (antibody does not distinguish the AP1 and 2 isoforms) clathrin heavy chain (CHC), or Tf receptor (TfR). (b) Colo205 cells were treated as in (a) and analyzed by immunoblot for processing of specific components of various types of clathrin-associated endocytic trafficking.
Figure 1:
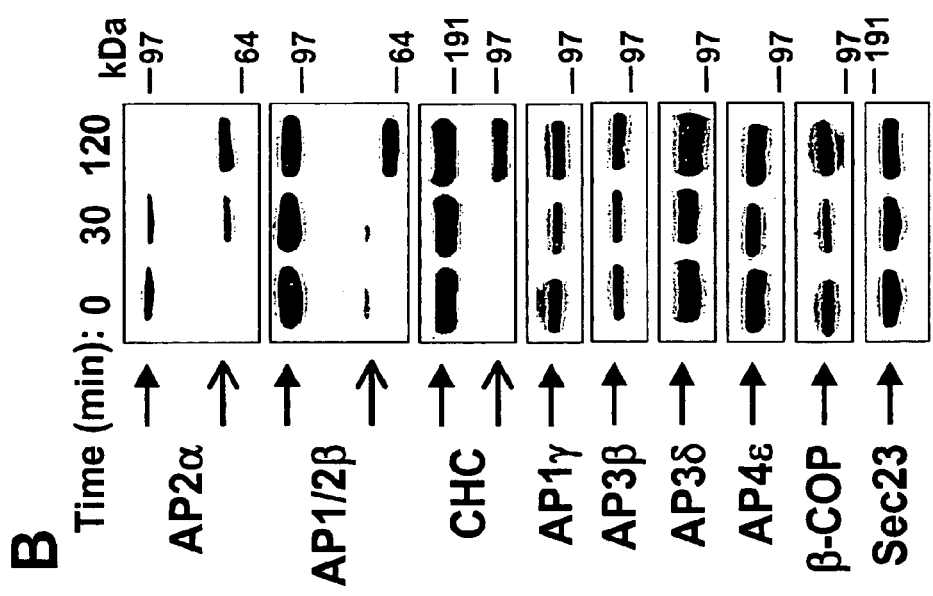

The terms "Apo-2 ligand", "Apo-2L", or "TRAIL" are used herein to refer to a polypeptide which includes amino acid residues 95-281, inclusive, 114-281, inclusive, residues 91-281, inclusive, residues 92-281, inclusive, residues 41-281, inclusive, residues 15-281, inclusive, or residues 1-281, inclusive, of the amino acid sequence shown in FIG. 1A of Pitti et al., *J. Biol. Chem.*, 271:12687-12690 (1996), as well as biologically active fragments, deletional, insertional, or substitutional variants of the above sequences. In one embodiment, the polypeptide sequence comprises residues 114-281. Optionally, the polypeptide sequence has at least residues 91-281 or residues 92-281. In another preferred embodiment, the biologically active fragments or variants have at least about 80% amino acid sequence identity, more preferably at least about 90% amino acid sequence identity, and even more preferably, at least about 95%, 96%, 97%, 98%, or 99% amino acid sequence identity with any one of the above sequences. The definition encompasses substitutional variants of the Apo-2 ligand comprising amino acids 91-281 of FIG. 1A of Pitti et al., *J. Biol. Chem.*, 271:12687-12690 (1996) in which at least one of the amino acids at positions 203, 218 or 269 (using the numbering of the sequence provided in Pitti et al., supra) are substituted by an alanine residue. The definition encompasses Apo-2 ligand isolated from an Apo-2 ligand source, such as from human tissue types, or from another source, or prepared by recombinant or synthetic methods. The term Apo-2 ligand also refers to the polypeptides described in WO 97/25428, supra, and WO97/01633, supra.

"Apo-2 ligand receptor" includes the receptors referred to in the art as "DR4" and "DR5". Pan et al. have described the TNF receptor family member referred to as "DR4" (Pan et al., *Science*, 276:111-113 (1997); see also WO98/32856 published Jul. 30, 1998). The DR4 receptor was reported to contain a cytoplasmic death domain capable of engaging the cell suicide apparatus. Pan et al. disclose that DR4 is believed to be a receptor for the ligand known as Apo2L/TRAIL. Sheridan et al., *Science*, 277:818-821 (1997) and Pan et al., *Science*, 277:815-818 (1997) described another receptor for Apo2L/TRAIL (see also, WO98/51793 published Nov. 19, 1998; WO98/41629 published Sep. 24, 1998). This receptor is referred to as DR5 (the receptor has also been alternatively referred to as Apo-2; TRAIL-R, TR6, Tango-63, hAPO8, TRICK2 or KILLER; Screaton et al., *Curr. Biol.*, 7:693-696 (1997); Walczak et al., *EMBO J.*, 16:5386-5387 (1997); Wu et al., *Nature Genetics*, 17:141-143 (1997); WO98/35986 published Aug. 20, 1998; EP870,827 published Oct. 14, 1998; WO98/46643 published Oct. 22, 1998; WO99/02653 published Jan. 21, 1999; WO99/09165 published Feb. 25, 1999; WO99/11791 published Mar. 11, 1999). Like DR4, DR5 is reported to contain a cytoplasmic death domain and be capable of signaling apoptosis. As described above, other receptors for Apo-2L include DcR1, DcR2, and OPG (see, Sheridan et al., supra; Marsters et al., supra; and Simonet et al., supra). The term "Apo-2L receptor" when used herein encompasses native sequence receptor and receptor variants. These terms encompass Apo-2L receptor expressed in a variety of mammals, including humans. Apo-2L receptor may be endogenously expressed as occurs naturally in a variety of human tissue lineages, or may be expressed by recombinant or synthetic methods. A "native sequence Apo-2L receptor" comprises a polypeptide having the same amino acid sequence as an Apo-2L receptor derived from nature. Thus, a native sequence Apo-2L receptor can have the amino acid sequence of naturally-occurring Apo-2L receptor from any mammal. Such native sequence Apo-2L receptor can be isolated from nature or can be produced by recombinant or synthetic means. The term "native sequence Apo-2L receptor" specifically encompasses naturally-occurring truncated or secreted forms of the receptor (e.g., a soluble form containing, for instance, an extracellular domain sequence), naturally-occurring variant forms (e.g., alternatively spliced forms) and naturally-occurring allelic variants. Receptor variants may include fragments or deletion mutants of the native sequence Apo-2L receptor.

The term "Fas" is used herein to refer to a polypeptide which includes amino acid residues 1-319 as shown in NCBI Accession No. AAA63174 and described in Itoh et al., Cell 66 (2), 233-243 (1991), as well as biologically active fragments, deletional, insertional, or substitutional variants of the above sequences. This polypeptide is designated "Apo-1" and "CD95" in certain art references. The term "Fas Ligand" or "FasL" is used herein to refer to a polypeptide which includes amino acid residues 1-281 as shown in NCBI Accession No. NP_000630 and described in Suda et al., Cell 75 (6), 1169-1178 (1993) as well as biologically active fragments, deletional, insertional, or substitutional variants of the above sequences. Binding of FasL to Fas, or cross-linking of Fas with agonistic antibodies, induces apoptosis that results in cell death (see, e.g. Nagata, S. Ann. Rev. Genet. 33:29, 1999; and Labroille et al., Cytometry 39(3): 195-202 (2000)). The binding of FasL to Fas activates a cascade of caspases via a FADD adaptor (Fas-associated protein with death domain), which leads to the cleavage of various cellular substrates and to DNA fragmentation.

"Percent (%) amino acid sequence identity" with respect to the polypeptide sequences identified herein is defined as the percentage of amino acid residues in a candidate sequence that are identical with the amino acid residues in a polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. Optionally, % amino acid sequence identity values are obtained by using the sequence comparison computer program ALIGN-2. The ALIGN-2 sequence comparison computer program was authored by Genentech, Inc. and the source code has been filed with user documentation in the U.S. Copyright Office, Washington, D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary. However, % amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

The term "antibody" is used in the broadest sense and specifically covers intact monoclonal antibodies, polyclonal antibodies, multispecific antibodies (e.g. bispecific antibodies) formed from at least two intact antibodies, and antibody fragments. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature,* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example. An antibody "which binds" an antigen of interest is one capable of binding that antigen with sufficient affinity and/or avidity such that the antibody is useful as a diagnostic or therapeutic agent for targeting a cell expressing the antigen.

"Death receptor antibody" is used herein to refer generally to antibody or antibodies directed to a receptor in the tumor necrosis factor receptor superfamily and containing a death domain capable of signalling apoptosis, and such antibodies include DR5 antibody, DR4 antibody and Fas antibody.

"DR5 receptor antibody", "DR5 antibody", or "anti-DR5 antibody" is used in a broad sense to refer to antibodies that bind to at least one form of DR5 receptor. Optionally the DR5 antibody is fused or linked to a heterologous sequence or molecule. Preferably the heterologous sequence allows or assists the antibody to form higher order or oligomeric complexes. Optionally, the DR5 antibody binds to DR5 receptor but does not bind or cross-react with any additional Apo-2L receptor (e.g. DR4, DcR1, or DcR2). Optionally the antibody is an agonist of DR5 signalling activity (see, e.g. United States Patent Application Nos. 20040005314 and 20060188498).

"DR4 receptor antibody", "DR4 antibody", or "anti-DR4 antibody" is used in a broad sense to refer to antibodies that bind to at least one form of a DR4 receptor or extracellular domain thereof. Optionally the DR4 antibody is fused or linked to heterologous sequence or molecule. Preferably the heterologous sequence allows or assists the antibody to form higher order or oligomeric complexes. Optionally, the DR4 antibody binds DR4 receptor but does not bind or cross-react with any additional Apo-2L receptor (e.g. DR5, Dc R1 or DcR2). Optionally the antibody is an agonist of DR4 signalling activity (see, e.g. United States Patent Application Nos. 20040005314 and 20060188498).

"Fas antibody", or "anti-Fas antibody" is used in a broad sense to refer to antibodies that bind to at least one form of Fas or extracellular domain thereof. Optionally the Fas antibody is fused or linked to heterologous sequence or molecule. Preferably the heterologous sequence allows or assists the antibody to form higher order or oligomeric complexes. Optionally, the Fas antibody binds Fas receptor but does not bind or cross-react with any additional FasL receptor. Optionally the antibody is an agonist of Fas signalling activity (see, e.g. Nagata, S. Ann. Rev. Genet. 33:29, 1999; and Labroille et al., Cytometry 39(3): 195-202 (2000)).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature*, 321:522-525 (1986); Reichmann et al., *Nature*, 332:323-329 (1988); and Presta, *Curr. Op. Struct. Biol.*, 2:593-596 (1992). The humanized antibody includes a PRIMATIZED™ antibody wherein the antigen-binding region of the antibody is derived from an antibody produced by immunizing macaque monkeys with the antigen of interest.

Antibodies are typically proteins or polypeptides which exhibit binding specificity to a specific antigen. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Chothia et al., *J. Mol. Biol.*, 186:651-663 (1985); Novotny and Haber, *Proc. Natl. Acad. Sci. USA*, 82:4592-4596 (1985)). The light chains of antibodies from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively.

"Antibody fragments" comprise a portion of an intact antibody, generally the antigen binding or variable region of the intact antibody. Examples of antibody fragments include Fab, Fab', F(ab')$_2$, and Fv fragments, diabodies, single chain antibody molecules, and multispecific antibodies formed from antibody fragments.

The term "variable" is used herein to describe certain portions of the variable domains which differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat, E. A. et al., *Sequences of Proteins of Immunological Interest*, National Institutes of Health, Bethesda, Md. (1987)). The constant domains are not involved directly in binding an antibody to an antigen, but exhibit various effector functions, such as participation of the antibody in antibody-dependent cellular toxicity.

The monoclonal antibodies herein include chimeric, hybrid and recombinant antibodies produced by splicing a variable (including hypervariable) domain of an anti-Apo-2L receptor antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity or properties. See, e.g. U.S. Pat. No. 4,816,567 and Mage et al., in *Monoclonal Antibody Production Techniques and Applications*, pp. 79-97 (Marcel Dekker, Inc.: New York, 1987).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al. *Nature Biotechnology*, 14:309-314 (1996): Sheets et al. *PNAS*, (USA) 95:6157-6162 (1998)); Hoogenboom and Winter, *J. Mol. Biol.*, 227:381 (1991); Marks et al., *J. Mol. Biol.*, 222:581 (1991)). Human antibodies can also be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology*, 10: 779-783 (1992); Lonberg et al., *Nature*, 368: 856-859 (1994); Morrison, *Nature*, 368:812-13 (1994); Fishwild et al., *Nature Biotechnology*, 14: 845-51 (1996); Neuberger, *Nature Biotechnology*, 14:826 (1996); Lonberg and Huszar, *Intern. Rev. Immunol.*, 13:65-93 (1995). Alternatively, the human antibody may be prepared via immortalization of human B lymphocytes producing an antibody directed against a target antigen (such B lymphocytes may be recovered from an individual or may have been immunized in vitro). See, e.g., Cole et al., *Monoclonal Antibodies and Cancer Therapy*, Alan R. Liss, p. 77 (1985); Boerner et al., *J. Immunol.*, 147 (1):86-95 (1991); and U.S. Pat. No. 5,750,373.

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region (using herein the numbering system according to Kabat et al., supra). The Fc region of an immunoglobulin generally comprises two constant domains, a CH2 domain and a CH3 domain, and optionally comprises a CH4 domain.

By "Fc region chain" herein is meant one of the two polypeptide chains of an Fc region.

The "CH2 domain" of a human IgG Fc region (also referred to as "Cγ2" domain) usually extends from an amino acid residue at about position 231 to an amino acid residue at about position 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec. Immuno.* 22:161-206 (1985). The CH2 domain herein may be a native sequence CH2 domain or variant CH2 domain.

The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" in one chain thereof and a corresponding introduced "cavity" in the other chain thereof; see U.S. Pat. No. 5,821,333).

"Hinge region" is generally defined as stretching from about Glu216, or about Cys226, to about Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions. The hinge region herein may be a native sequence hinge region or a variant hinge region. The two polypeptide chains of a variant hinge region generally retain at least one cysteine residue per polypeptide chain, so that the two polypeptide chains of the variant hinge region can form a disulfide bond between the two chains. The preferred hinge region herein is a native sequence human hinge region, e.g. a native sequence human IgG1 hinge region.

A "functional Fc region" possesses at least one "effector function" of a native sequence Fc region. Exemplary "effector functions" include Clq binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

The terms "Fc receptor" and "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daëron, *Annu. Rev. Immunol.*, 15:203-234 (1997)). FcRs are reviewed in Ravetch and Kinet, *Annu. Rev. Immunol.*, 9:457-92 (1991); Capel et al., *Immunomethods*, 4:25-34 (1994); and de Haas et al., *J. Lab. Clin. Med.*, 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.*, 117:587 (1976); and Kim et al., *J. Immunol.*, 24:249 (1994)).

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology*, 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene*, 169:147-155 (1995); Yelton et al. *J. Immunol.*, 155:1994-2004 (1995); Jackson et al., *J. Immunol.*, 154(7):3310-9 (1995); and Hawkins et al, *J. Mol. Biol.*, 226:889-896 (1992).

The word "label" when used herein refers to a compound or composition which is coupled or fused directly or indirectly to a reagent such as an antibody and facilitates detection of the reagent to which it is coupled or fused. The label may itself be detectable (e.g., radioisotope labels, fluorescent labels) or, in the case of an enzymatic label, may catalyze chemical alteration of substrate compound composition which is detectable.

The term "antagonist" is used in the broadest sense, and includes any molecule that partially or fully blocks, inhibits, or neutralizes one or more biological activities of Apo2L/TRAIL, DR4 or DR5, FasL or Fas in vitro, in situ, or in vivo. Examples of such biological activities of Apo2L/TRAIL, DR4 or DR5 include binding of Apo2L/TRAIL to DR4 or DR5, induction of apoptosis as well as those further reported in the literature. Examples of such biological activities of FasL and Fas include binding of FasL to Fas, induction of apoptosis as well as those further reported in the literature. An antagonist may function in a direct or indirect manner. For instance, the antagonist may function to partially or fully block, inhibit or neutralize one or more biological activities of Apo2L/TRAIL, in vitro, in situ, or in vivo as a result of its direct binding to DR4 or DR5. The antagonist may also function indirectly to partially or fully block, inhibit or neutralize one or more biological activities of Apo2L/TRAIL, DR4 or DR5, in vitro, in situ, or in vivo as a result of, e.g., blocking or inhibiting another effector molecule. The antagonist molecule may comprise a "dual" antagonist activity wherein the molecule is capable of partially or fully blocking, inhibiting or neutralizing a biological activity of Apo2L/TRAIL, DR4 or DR5, Fas or FasL.

The term "agonist" is used in the broadest sense, and includes any molecule that partially or fully enhances, stimulates or activates one or more biological activities of Apo2L/TRAIL, DR4 or DR5, FasL or Fas in vitro, in situ, or in vivo. Examples of such biological activities binding of Apo2L/TRAIL to DR4 or DR5, apoptosis as well as those further reported in the literature. Examples of such biological activities of FasL and Fas include binding of FasL to Fas, induction of apoptosis as well as those further reported in the literature. An agonist may function in a direct or indirect manner. For instance, the agonist may function to partially or fully enhance, stimulate or activate one or more biological activities of DR4 or DR5, in vitro, in situ, or in vivo as a result of its direct binding to DR4 or DR5, which causes receptor activation or signal transduction. The agonist may also function indirectly to partially or fully enhance, stimulate or activate one or more biological activities of DR4 or DR5, in vitro, in situ, or in vivo as a result of, e.g., stimulating another effector molecule which then causes DR4 or DR5 activation or signal transduction. It is contemplated that an agonist may act as an enhancer molecule which functions indirectly to enhance or increase DR4 or DR5 activation or activity. For instance, the agonist may enhance activity of endogenous Apo-2L in a mammal. This could be accomplished, for example, by pre-complexing DR4 or DR5 or by stabilizing complexes of the respective ligand with the DR4 or DR5 receptor (such as stabilizing native complex formed between Apo-2L and DR4 or DR5).

"Isolated," when used to describe the various proteins disclosed herein, means protein that has been identified and separated and/or recovered from a component of its natural environment. Contaminant components of its natural environment are materials that would typically interfere with diagnostic or therapeutic uses for the protein, and may include enzymes, hormones, and other proteinaceous or non-proteinaceous solutes. In preferred embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated protein includes protein in situ within recombinant cells, since at least one component of the protein natural environment will not be present. Ordinarily, however, isolated protein will be prepared by at least one purification step.

"Biologically active" or "biological activity" for the purposes herein means (a) having the ability to induce or stimulate apoptosis in at least one type of mammalian cancer cell or virally-infected cell in vivo or ex vivo; (b) capable of raising an antibody, i.e., immunogenic; or (c) retaining the activity of a native or naturally-occurring Apo-2 ligand polypeptide.

A "growth inhibitory agent" when used herein refers to a compound or composition which inhibits growth of a cell in vitro and/or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

The term "prodrug" as used in this application refers to a precursor or derivative form of a pharmaceutically active substance that is less cytotoxic to cancer cells compared to the parent drug and is capable of being enzymatically activated or converted into the more active parent form. See, e.g., Wilman, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described below.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $p^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of conditions like cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin ($_1^I$ and calicheamicin $2^I_1$, see, e.g., Agnew *Chem. Intl. Ed. Engl.* 33:183-186 (1994); dynemicin, including dynemicin A; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

"Treatment" or "therapy" refer to both therapeutic treatment and prophylactic or preventative measures.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing tumor burden or volume, the time to disease progression (TTP) and/or determining the response rates (RR).

"Mammal" for purposes of treatment or therapy refers to any animal classified as a mammal, including humans, domestic and farm animals, and zoo, sports, or pet animals, such as dogs, horses, cats, cows, etc. Preferably, the mammal is human.

By "subject" or "patient" is meant any single subject for which therapy is desired, including humans. Also intended to be included as a subject are any subjects involved in clinical research trials not showing any clinical sign of disease, or subjects involved in epidemiological studies, or subjects used as controls.

The terms "cancer", "cancerous", or "maligant" refer to or describe the physiological condition in mammals that is typically characterized by unregulated cell growth. Examples of cancer include but are not limited to, carcinoma, lymphoma, blastoma, sarcoma, and leukemia. More particular examples of such cancers include colon cancer, colorectal cancer, rectal cancer, squamous cell cancer, small-cell lung cancer, non-small cell lung cancer, Hodgkin's and non-Hodgkin's lymphoma, testicular cancer, esophageal cancer, gastrointestinal cancer, renal cancer, pancreatic cancer, glioblastoma, cervical cancer, ovarian cancer, glioma, liver cancer, bladder cancer, hepatoma, breast cancer, endometrial carcinoma, salivary gland carcinoma, kidney cancer, liver cancer, prostate cancer, vulval cancer, thyroid cancer, hepatic carcinoma and various types of head and neck cancer.

Figure 2:
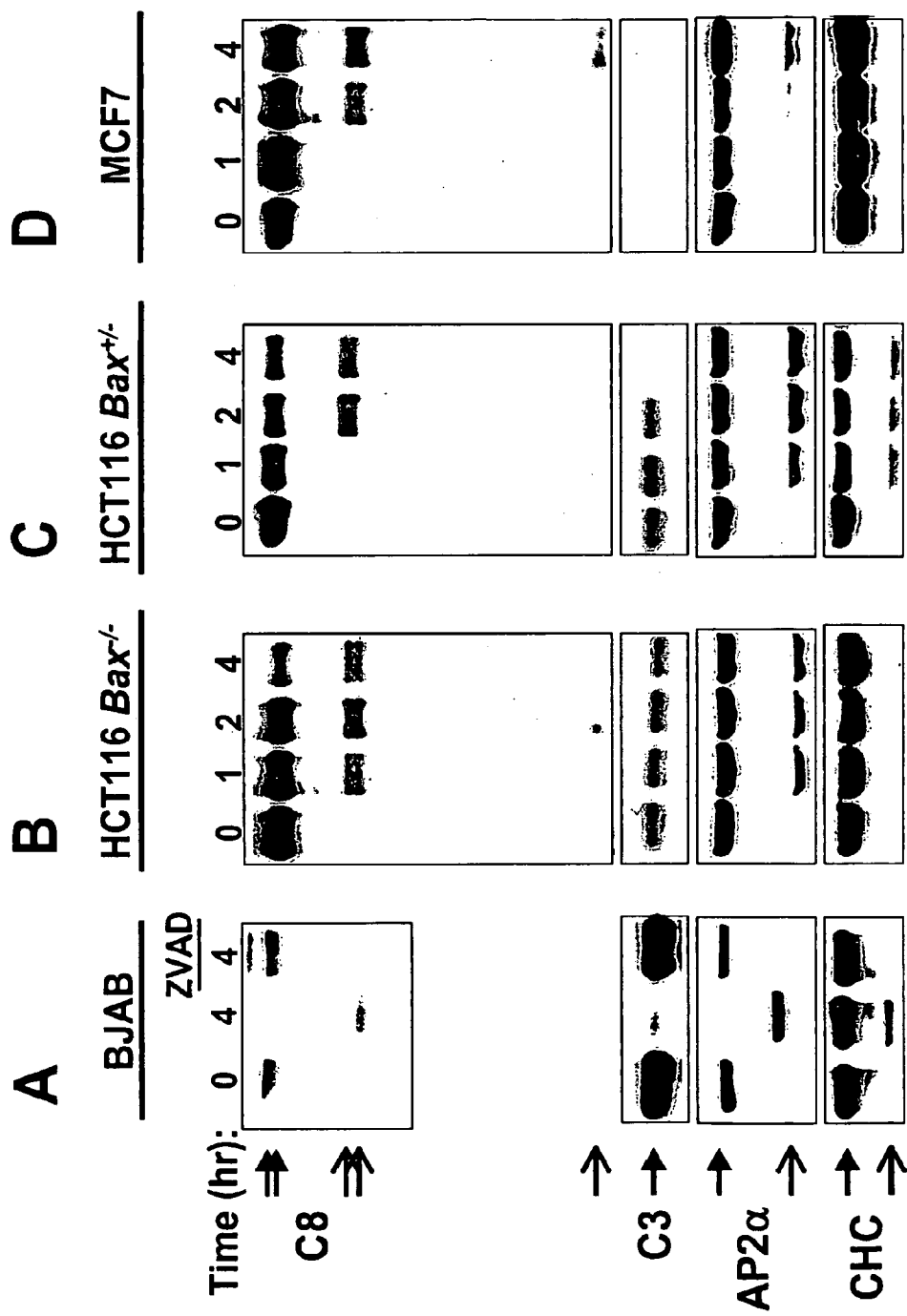

The term "biomarker" as used in the present application refers generally to a molecule, including a gene, protein or protein fragment, carbohydrate structure, or glycolipid, the expression of which in or on a mammalian tissue or cell can be detected by standard methods (methods disclosed herein) and is predictive for a mammalian cell's or tissue's sensitivity to an apoptosis inducing agent such as Apo2L/TRAIL or death receptor antibody. Such biomarkers contemplated by the present invention include but are not limited to a protein fragment of AP2-α (SEQ ID NO: 1), clathrin heavy chain (SEQ ID NO: 2), AP1/2β (SEQ ID NO: 3) or dynamin (SEQ ID NO: 4) as disclosed herein (see, e.g. FIGS. 1 and 2).

By "tissue or cell sample" is meant a collection of similar cells obtained from a tissue of subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from primary or metastatic tumor. The tissue sample may contain compounds which are not naturally intermixed with the tissue in nature such as preservatives, anticoagulants, buffers, fixatives, nutrients, antibiotics, or the like.

For the purposes herein a "section" of a tissue sample is meant a single part or piece of a tissue sample, e.g. a thin slice of tissue or cells cut from a tissue sample. It is understood that multiple sections tissue samples may be taken and subjected to analysis according to the present invention.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of first analysis or protocol to determine whether a second analysis or protocol should be performed. With respect to various embodiments disclosed herein; one may use the results of an analytical assay such as one that identifies fragments of AP2-α (SEQ ID NO: 1), clathrin heavy chain (SEQ ID NO: 2), AP1/2β (SEQ ID NO: 3) or dynamin (SEQ ID NO: 4) generated during apoptosis to determine whether a specific therapeutic regimen using and apoptosis inducing agent such as Apo2L/TRAIL, FasL, death receptor antibody or the like should be performed.

II. Methods And Materials
A. Methods

Generally, the methods and materials of the invention are used to detect and/or monitor apoptosis in a mammalian cell, for example by contacting the cell with an antibody that binds to a protein fragment generated during apoptosis, wherein the antibody binds to a protein fragment of AP2-α (SEQ ID NO: 1), clathrin heavy chain (SEQ ID NO: 2), AP1/2β (SEQ ID NO: 3) or dynamin (SEQ ID NO: 4); determining the amount of the antibody which binds to the protein fragment generated during apoptosis; and then comparing the amount of antibody bound in the mammalian cell with the amount of antibody which binds to the protein fragment in a mammalian cell free of apoptosis, wherein if the amount in the cell being examined is greater than the amount in the cell free of apoptosis, then apoptosis is detected. As illustrated in the examples provided herein, contacting the cell with an antibody that binds to a protein fragment generated during apoptosis includes methods which contact the cellular components of the cells. Typically, the cell is pretreated for example by extraction (e.g. as in the Western blot procedures noted herein) to facilitate the antibody's contact of components of the cell.

The methods and assays disclosed herein can be used in a number of contexts. For example, there are some populations of diseased human cell types (such as certain populations of cancer cells) which are resistant to the cell death inducing effects of Apo2L/TRAIL or death receptor antibodies. It is therefore believed that the disclosed methods and assays can provide for convenient, efficient and potentially cost-effective means to obtain data and information useful in assessing appropriate or effective therapies for treating patients. For example, a patient diagnosed with cancer or an immune related condition could have a biopsy performed to obtain a tissue or cell sample, and the sample examined by various in vitro assays of the invention to determine whether a patient's cells are sensitive to a therapeutic agent such as Apo2/TRAIL or death receptor antibody.

For sample preparation, a tissue or cell sample from a mammal (typically a human patient) may be used. Examples of samples include, but are not limited to, cancer cells such as colon, breast, prostate, ovary, lung, stomach, pancreas, lymphoma, and leukemia cancer cells. Optionally, the samples include non-small cell lung cancer cells, pancreatic cancer cells or non-Hodgkin's lymphoma cancer cells. The sample can be obtained by a variety of procedures known in the art including, but not limited to surgical excision, aspiration or biopsy.

The invention disclosed herein has a number of embodiments. For example, certain embodiments of the invention can be used to observe cell apoptosis, and associated conditions in a subject such as a mammal, and in particular a human subject. In one illustrative embodiment, methods of the invention are used to observe the presence (or absence) of apoptosis in mammalian cells in order to examine the sensitivity of a mammalian cell to one or more apoptosis inducing agents such as Apo2/TRAIL or FasL, for example to assess the efficacy of a therapy comprising the administration of such agents. The methods of the present invention can also be used to determine the extent of activity of a candidate compound in decreasing or increasing the apoptotic activity in a mammalian cell, for example one which modulates the activity of an apoptosis inducing agent such as Apo2L/TRAIL (SEQ ID NO: 7), FasL (SEQ ID NO: 9), a Fas agonist antibody, a DR4 agonist antibody or a DR5 agonist antibody. Embodiments of the invention are also useful for identification of compounds which inhibit or stimulate apoptotic cell death by determining that the compounds inhibits or stimulates the formation of apoptosis-generated protein fragments.

A typical embodiment of the invention is a method of detecting apoptosis in a mammalian cell by contacting the cell with an antibody that binds to a protein fragment generated during apoptosis, wherein the antibody binds to a protein fragment of AP2-α (SEQ ID NO: 1), clathrin heavy chain (SEQ ID NO: 2), AP1/2β (SEQ ID NO: 3) or dynamin (SEQ ID NO: 4), determining the amount of the antibody which binds to the protein fragment generated during apoptosis; and then comparing the amount of antibody bound in the mammalian cell with the amount of antibody which binds to the protein fragment in a mammalian cell free of apoptosis, wherein if the amount in this mammalian cell is greater than the amount in the cell free of apoptosis, then apoptosis is detected. A wide variety of mammalian cells can be used in such methods. In certain embodiments of the invention, the cell is a human colon, colorectal, lung, breast, prostate, bladder, kidney, ovarian, brain, melanoma, leukemia or myeloma cancer cell.

Another embodiment of the invention is a method for identifying a human cancer cell that is likely to respond, or is responsive to a therapeutic agent that induces apoptosis in human cancer cells. This embodiment of the invention includes the steps of exposing the human cancer cell to the therapeutic agent; examining the human cancer cell exposed to the therapeutic agent for the presence of a protein fragment of AP2-α (SEQ ID NO: 1), clathrin heavy chain (SEQ ID NO: 2), AP1/2β (SEQ ID NO: 3) or dynamin (SEQ ID NO: 4); comparing the amount of protein fragment in the human cancer cell with the amount of protein fragment in a control human cancer cell not exposed to the ligand. In this embodiment, apoptosis is observed when the amount of protein fragment present in the human cancer cell exposed to the therapeutic agent is greater than the amount of protein fragment in the control human cancer cell not exposed to the therapeutic agent; and an observation of apoptosis in the human cancer cell identifies the human cancer cell as likely to respond, or responsive to the therapeutic agent. In certain embodiments of the invention, the human cancer cell is obtained from an individual diagnosed with a cancer and has been grown in an in vitro culture for less than one month and typically less than 2 weeks, or less than one week. In alternative embodiments, the human cancer cell is an immortalized cell line obtained from an in vitro culture.

In typical embodiments of the invention, the amount of antibody bound in the mammalian cell which is being observed for the presence of apoptosis, for example a mammalian cell exposed to an apoptosis inducing agent, is compared with the amount of antibody which binds to the protein fragment in a mammalian cell free of apoptosis, for example a control cell which has not been exposed to the apoptosis inducing agent. One of skill in the art understands that such control cells are those selected to be like the experimental mammalian cell which is being observed for the presence of apoptosis except for the variable being tested (e.g. exposure to an apoptosis inducing agent). In one embodiment of the invention, the control cell is a cell from the same source (e.g. a biopsy sample from the site of a primary or metastatic tumor) and/or is of the same lineage as the experimental mammalian cell which is being observed for the presence of apoptosis except that the control mammalian cell is not exposed to an agent that initiates signalling of Death Receptor 4 (SEQ ID NO: 5), Death Receptor 5 (SEQ ID NO: 6) or Fas (SEQ ID NO: 8). In certain embodiments of the invention, the pattern of fragmentation of AP2-α (SEQ ID NO: 1), clathrin heavy chain (SEQ ID NO: 2), AP1/2β (SEQ ID NO: 3) or dynamin (SEQ ID NO: 4) in such control cells has already been characterized and it is this previously characterized pattern of fragmentation in the control cell that is compared to the pattern of fragmentation of AP2-α (SEQ ID NO: 1), clathrin heavy chain (SEQ ID NO: 2), AP1/2β (SEQ ID NO: 3) or dynamin (SEQ ID NO: 4) in the mammalian cell which is being observed for the presence of apoptosis. Such embodiments are used for example in order to eliminate unnecessary and redundant characterizations of cellular controls, for example controls characterized as cells being free of apoptosis.

Embodiments of the invention can be used to examine cells undergoing apoptosis induced by any of the wide variety of factors known to initiate this programmed cell death, for example heat, radiation and chemical agents. These embodiments typically observe apoptosis in the cell that initiated through a receptor on the surface of the cell, for example Death Receptor 4 (SEQ ID NO: 5), Death Receptor 5 (SEQ ID NO: 6) or Fas (SEQ ID NO: 8). In certain embodiments of the invention, the cell is contacted with a polypeptide such as Apo2L/TRAIL (SEQ ID NO: 7), FasL (SEQ ID NO: 9), a Fas agonist antibody, a DR4 agonist antibody or a DR5 agonist antibody, and the described methods for the detection of apoptosis (which include the detection of no apoptosis) are used for example to obtain information on the efficacy of a therapy comprising the administration of such agents.

The methods of the invention can also be used to identify new apoptosis inducing agents and/or modulators of apoptosis inducing agents. Illustrative embodiments can include the step of exposing the mammalian cell to one or more test agents and then using methods of the invention to observe apoptosis, with detection of apoptosis in the mammalian cell identifying the one or more test agents as an inducer of apoptosis in the mammalian cell. Methods of the invention can also be combined with complimentary methods of cellular analysis, for example genetic profiling. One such embodiment of the invention includes the step of examining the expression of at least one mRNA in the mammalian cell in which apoptosis is observed.

Method of the invention include observations of cellular proteins that are shown herein to fragment in cells undergoing apoptosis. These protein fragment, for example fragments of AP2-α (SEQ ID NO: 1), clathrin heavy chain (SEQ ID NO: 2), AP1/2β (SEQ ID NO: 3) or dynamin (SEQ ID NO: 4) can be observed by any one of a wide variety of assays known in the art. Typically such fragments are observed using immunoblotting, an enzyme linked immunoadsorbent assay or immunohistochemistry. In addition, the methods of the invention can be used to examine a number of the protein fragments identified herein, for example a protein fragment of AP2α having a molecular weight of about 64 kDa or 33 kDa. In certain embodiments of the invention, the protein fragment bound by the antibody is identified by amino acid sequences specific to that fragment, for example AP2-α amino acid sequences DVFD residues 684 to 687 of SEQ ID NO: 1 or GPAA residues 688 to 691 of SEQ ID NO: 1.

As noted above, embodiments of the present invention include methods of determining if a human patient diagnosed with cancer is likely to respond to treatment with one or more apoptosis inducing agents, for example APO-2/TRAIL. These methods can be adapted to be used with a variety of other methods known in the art that facilitate the determination of whether a patient diagnosed with cancer is likely to respond to treatment with an agent(s) such as an apoptosis inducing agent, for example, those methods which examining the expression of at least one gene (e.g. the presence or level of the mRNA or protein encoded by that mRNA) in a human patient diagnosed with cancer (e.g. in a primary tumor or a metastasis). Such genetic profiling methods are well known in the art and described for example in U.S. Patent Application No. 20060015952).

One such embodiment of the methods of the invention can include the step of observing fragments generated during apoptosis including protein fragments of AP2-α (SEQ ID NO: 1), clathrin heavy chain (SEQ ID NO: 2), AP1/2β (SEQ ID NO: 3) or dynamin (SEQ ID NO: 4) in cancer cells obtained from the patient; in combination with the step of obtaining a gene expression profile of multiple genes and comparing it with a gene expression profile of a noncancerous cell of the same lineage and/or cancer cells obtained from an animal model that are know to be responsive (or alternatively unresponsive) to treatment with one or more apoptosis inducing agents. Typically such methods can include the step of further identifying the patient as likely to benefit from treatment with one or more apoptosis inducing agents, for example if the cancer cells obtained from the patient have a gene expression profile similar to the gene expression profile of cancer cells obtained from patients (or an animal model of the cancer) that are known to benefit from treatment with the one or more apoptosis inducing agents.

For purposes herein, "similar" means that the expression profiles resemble or track each other in one or more ways, by showing patterns of expression that are within about 80% to 100% identical in quantity or other measurable expression parameter depending on the assay or technique used to measure the gene expression profile, as described further below in detail, more preferably within about 90 to 100%, and more preferably within about 95 to 100% identical. The gene expression profiles of the cancer cells from the patient and from the animal model are generally obtained by the same technique or assay to facilitate comparison thereof.

Methods of gene expression profiling are well known in the art and are typically based either on hybridization analysis of polynucleotides or sequencing of polynucleotides. The most commonly used methods known in the art for the quantification of mRNA expression in a sample include northern blotting and in situ hybridization (Parker and Barnes, Methods in Molecular Biology, 106:247-283 (1999)); RNAse protection assays (Hod, Biotechniques, 13:852-854 (1992)); and reverse transcription polymerase chain reaction (RT-PCR) (Weis et al., Trends in Genetics, 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). Any of these methods, or other methods known in the art, can be used to determine the gene expression profile of a tumor cell obtained from a patient, such as a human patient, and an animal serving as a model of a cancer responsive to a TGF-β antagonist, such as a mouse model. In the case of human patients, the source of tumor cells can be a fresh, frozen or fixed and paraffin-embedded tissue sample, from which mRNA can be extracted and subjected to gene expression analysis.

Alternatively, proteomics techniques can also be used to compare the expression profile of a human and reference (e.g. mouse) proteins in a cancer cell. A proteomic profile is a representation of the expression pattern of a plurality of proteins in a biological sample, e.g. a cancer tissue. The expression profile can, for example, be represented as a mass spectrum, but other representations based on any physicochemical or biochemical properties of the proteins are also included. Thus the expression profile may, for example, be based on differences in the electrophoretic properties of proteins, as determined by two-dimensional gel electrophoresis, e.g. by 2-D PAGE, and can be represented, e.g. as a plurality of spots in a two-dimensional electrophoresis gel. Proteomics techniques are well known in the art, and are described, for example, in the following textbooks: Proteome Research: New Frontiers in Functional Genomics (Principles and Practice), M. R. Wilkins et al., eds., Springer Verlag, 1007; 2-D Proteome Analysis Protocols, Andrew L Link, editor, Humana Press, 1999; Proteome Research: Two-Dimensional Gel Electrophoresis and Identification Methods (Principles and Practice), T. Rabilloud editor, Springer Verlag, 2000; Proteome Research: Mass Spectrometry (Principles and Practice), P. James editor, Springer Verlag, 2001; Introduction to Proteomics, D. C. Liebler editor, Humana Press, 2002; Proteomics in Practice: A Laboratory Manual of Proteome Analysis, R. Westermeier et al., eds., John Wiley & Sons, 2002.

Protein fragments generated during apoptosis including protein fragments of AP2-α (SEQ ID NO: 1), clathrin heavy chain (SEQ ID NO: 2), AP1/2β (SEQ ID NO: 3) or dynamin (SEQ ID NO: 4); in a sample can be analyzed by a number of means well known in the art. Typical protocols for evaluating such protein fragments are found, for example in Ausubel et al. eds., 1995, Current Protocols In Molecular Biology, Unit 15 (Immunoblotting). Immunoassays which can be used in certain embodiments of the present invention include, but are not limited to: Western blots, immunoprecipitation, slot or dot blot assays, immunostaining, RIA, scintillation proximity assays, fluorescent immunoassays using antibody conjugates or antigen conjugates of fluorescent substances such as fluorescein or rhodamine, Ouchterlony double diffusion analysis, ELISA, cell-based ELISA, filter-binding ELISA, inhibition ELISA, and immunoassays employing an avidin-biotin or a streptavidin-biotin detection system.

In some embodiments of the invention, an antibody used in the immunoassay binds to both the intact protein and a protein fragment and the protein fragment is recognized by its characteristically smaller size, for example in a Western blot procedure. For example, the antibody used in an embodiment of the invention can be one of the exemplary antibodies disclosed herein or an antibody which binds to an epitope bound by one of the exemplary antibodies disclosed herein. In other embodiments of the invention, antibodies which specifically recognize apoptosis-generated protein fragments, but not intact proteins can be used. Such antibodies can be prepared by standard immunization methods using the fragment as the immunogen and then identifying those antibodies generated that bind apoptosis-generated protein fragments, but not intact protein.

In typical embodiments of the present invention, analysis is performed on proteins obtained from lysed cells which have been separated by means of SDS-polyacrylamide gel electrophoresis ("PAGE"). The proteins are contacted with an antibody and analysis is performed, preferably by immunoassay, to determine the presence of protein fragments which bind to the antibody. Comparison may be made to a control consisting of proteins from similar lysed cells (e.g. cells from the same source and/or lineage) known to be free of apoptosis. Any of the immunoassays described above can be used to analyze a tissue sample from a live subject. Possible biological samples for this analysis include blood cells or biopsied cell or tissue samples which can be obtained by standard methods. The levels of apoptosis-generated peptide fragments in the above-described biological samples can be determined in any of the immunoassays described above employing antibodies that bind specifically to protein fragments of AP2-α (SEQ ID NO: 1), clathrin heavy chain (SEQ ID NO: 2), AP1/2β (SEQ ID NO: 3) or dynamin (SEQ ID NO: 4). The level of apoptosis-generated peptide fragments determined in the biological sample from the subject being analyzed is compared to the level found in an unaffected patient cell, or in a known standard. An exemplary standard can be for example, the presence and/or concentration of one or more protein fragments typically observed in cells not undergoing apoptosis (e.g. in control cells not exposed to an apoptosis inducing agent). Such embodiments can be used for example to diagnose conditions characterized by abnormal apoptosis. In certain embodiments of the invention, a level of apoptosis is observed within the cell, with, for example, an increase in apoptosis-generated peptide fragments of at least 10, 20, 30, 40 or percent, 100 or 150 percent, compared to a control sample, considered indicative of a pathological condition. In other embodiments of the invention, a level of apoptosis is observed within the cell, with, for example, an increase in apoptosis-generated peptide fragments of at least 10 fold, 100 fold or 1000 fold, compared to a control sample, considered indicative of a pathological condition.

Embodiments of the invention can be adapted for use in immunological assays useful for the detection and quantification of protein fragments of AP2-α (SEQ ID NO: 1), clathrin heavy chain (SEQ ID NO: 2), AP1/2β (SEQ ID NO: 3) or dynamin (SEQ ID NO: 4). Such assays can comprise one or more antibodies capable of recognizing and binding a protein fragment, as appropriate. These assays are performed within various immunological assay formats well known in the art, including but not limited to various types of Western blot assays, radioimmunoassays, enzyme-linked immunosorbent assays (ELISA), enzyme-linked immunofluorescent assays (ELIFA), and the like.

In illustrative methods, the sample may be contacted with an antibody specific for a biomarker such as a protein fragment of AP2-α (SEQ ID NO: 1), clathrin heavy chain (SEQ ID NO: 2), AP1/2β (SEQ ID NO: 3) or dynamin (SEQ ID NO: 4); under conditions sufficient for an antibody-biomarker complex to form, and then detecting said complex. Detecting the presence of a protein fragment biomarker may be accomplished in a number of ways, such as by Western blotting (with or without an immunoprecipitation step) and ELISA procedures for assaying wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of labelled antibody to a target biomarker.

Sandwich assays are among the most useful and commonly used assays. A number of variations of the sandwich assay technique exist, and all are intended to be encompassed by the present invention. Briefly, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labelled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding physically adsorbing, the polymer-antibody complex is washed in preparation for the test sample. An aliquot of the sample to tested is then added to the solid phase complex and incubated for a period of time sufficient (e.g. 2-40 minutes or overnight if more convenient) and under suitable conditions (e.g. from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

An alternative method involves immobilizing a target biomarker in the sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule. By "reporter molecule", as used in the present specification, is meant a molecule which, by its chemical nature, provides an analytically identifiable signal which allows the detection of antigen-bound antibody. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In typical cases, the enzyme-labelled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample. Alternately, fluorescent compounds, such as fluorescein and rhodamine, may be chemically coupled to antibodies without altering their binding capacity. When activated by illumination with light of particular wavelength, the fluorochrome-labelled antibody adsorbs the light energy, inducing a state to excitability in the molecule followed by emission of the light at characteristic color visually detectable with a light microscope. As in the EIA, the fluorescent labelled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art. However, other reporter molecules, such as radioisotope, chemiluminescent or bioluminescent molecules, may also be employed.

As noted above, embodiments of the invention can use antibodies that bind to a protein fragment of AP2-α (SEQ ID NO: 1), clathrin heavy chain (SEQ ID NO: 2), AP1/2β (SEQ ID NO: 3) or dynamin (SEQ ID NO: 4); but not the complete protein (e.g. antibodies that bind to epitope produced by the cleavage of the full length protein). Such embodiments can be used to examine protein fragments in a cell by immunohistochemical staining techniques. In such techniques, a tissue sample may be fixed (i.e. preserved) by conventional methodology (See e.g., "Manual of Histological Staining Method of the Armed Forces Institute of Pathology," $3^{rd}$ edition (1960) Lee G. Luna, H T (ASCP) Editor, The Blakston Division McGraw-Hill Book Company, New York; *The Armed Forces Institute of Pathology Advanced Laboratory Methods in Histology and Pathology* (1994) Ulreka V. Mikel, Editor, Armed Forces Institute of Pathology, American Registry of Pathology, Washington, D.C.). One of skill in the art will appreciate that the choice of a fixative is determined by the purpose for which the tissue is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a tissue sample. Subsequent to tissue preparation, a tissue section may be subjected to one of the variety of immunohistochemical techniques known in the art.

B. Materials

A variety of materials can be used in the practice of the invention including any one of a wide variety of apoptosis inducing agents as well as antibodies that bind the protein fragments disclosed herein that are generated during apoptotic cell death. Exemplary apoptosis inducing agents include Apo2L, anti-DR4 or DR5 agonist antibodies, FasL and anti-Fas agonist antibodies. The Apo-2L which can be employed in the methods includes the Apo-2L polypeptides described in Pitti et al., supra, WO 97/25428, supra, and WO97/01633, supra (the polypeptides referred to as TRAIL). It is contemplated that various forms of Apo-2L may be used, such as the full length polypeptide as well as soluble forms of Apo-2L which comprise an extracellular domain (ECD) sequence. Examples of such soluble ECD sequences include polypeptides comprising amino acids 114-281, 95-281, 91-281 or 92-281 of the Apo-2L sequence shown in FIG. 1A of Pitti et al., *J. Biol. Chem.*, 271:12687-12690 (1996). It is presently believed that the polypeptide comprising amino acids 92-281 is a naturally cleaved form of Apo-2L. Applicants have expressed human Apo-2L in CHO cells and found that the 92-281 polypeptide is the expressed form of Apo-2L. Modified forms of Apo-2L, such as the covalently modified forms described in WO 97/25428 are included. In particular, Apo-2L linked to a non-proteinaceous polymer such as polyethylene glycol is included for use in the present methods. The Apo-2L polypeptide can be made according to any of the methods described in WO 97/25428.

Variants of Apo-2 ligand having apoptotic activity which can be used in the methods include, for example, those identified by alanine scanning techniques. Particular substitutional variants comprise amino acids 91-281 of FIG. 1A of Pitti et al., *J. Biol. Chem.*, 271:12687-12690 (1996) in which at least one of the amino acids at positions 203, 218 or 269 are substituted by an alanine residue. Optionally, the Apo-2 ligand variants may include one or more of these three different site substitutions.

It is contemplated that a molecule which mimics the apoptotic activity of Apo-2L and/or FasL may alternatively be employed in the presently disclosed methods. Examples of such molecules include agonistic antibodies which can induce apoptosis in at least a comparable or like manner to Apo-2L. In particular, these agonist antibodies would comprise antibodies to one or more of the receptors for Apo-2L. Preferably, the agonist antibody is directed to an Apo-2L receptor which includes a cytoplasmic death domain such as DR4 or DR5. Even more preferably, the agonist antibody binds to such a receptor and binding can be determined, e.g., using FACS analysis or ELISA. Agonist antibodies directed to the receptor called DR5 (or Apo-2) have been prepared using fusion techniques such as described below. One of the DR5 or Apo-2 receptor agonist antibodies is referred to as 3F11.39.7 and has been deposited with ATCC as deposit no. HB-12456 on Jan. 13, 1998. Agonist activity of the Apo-2L receptor antibodies can be determined using various methods for assaying for apoptotic activity, and optionally, apoptotic activity of such antibody can be determined by assaying the antibody, alone or in a cross-linked form using Fc immunoglobulin or complement.

Additionally, agonist antibodies directed to another Apo-2L receptor called DR4 have also been prepared. An exemplary DR4 agonist antibodies is referred to as 4H6.17.8 and was deposited with ATCC as deposit no. HB-12455 on Jan. 13, 1998. Agonist activity of the Apo-2L receptor antibodies can be determined using various methods for assaying for apoptotic activity, and optionally, apoptotic activity of such antibody can be determined by assaying the antibody, alone or in a cross-linked form using Fc immunoglobulin or complement.

Agonist antibodies contemplated by the invention include antibodies which bind a single Apo-2L receptor or more than one Apo-2L receptor. An antibody which binds more than one Apo-2L receptor can be characterized as an antibody that "cross-reacts" with two or more different antigens and capable of binding to each of the different antigens, e.g. as determined by ELISA or FACS as in the examples below. Optionally, an antibody which "specifically cross-reacts" with two or more different antigens is one which binds to a first antigen and further binds to a second different antigen, wherein the binding ability of the antibody for the second antigen at an antibody concentration of about 10 µg/mL is from about 50% to about 100% (preferably from about 75% to about 100%) of the binding ability of the first antigen as determined in a capture ELISA (such as in the examples below). For example, the antibody may bind specifically to DR5 (the "first antigen") and specifically cross-react with another Apo-2L receptor such as DR4 (the "second antigen"), wherein the extent of binding of about 10:g/mL of the antibody to DR4 is about 50% to about 100% of the binding ability of the antibody for DR5 in the capture ELISA herein. Various cross-reactive antibodies to Apo-2L receptors are described in further detail in International Patent application number PCT/US99/13197.

As described below, exemplary forms of antibodies useful in the practice of embodiments of the invention include polyclonal, monoclonal, humanized, bispecific, and heteroconjugate antibodies.

1. Polyclonal Antibodies

The antibodies used in the practice of the invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include for example a complete or partial AP2-α (SEQ ID NO: 1), clathrin heavy chain (SEQ ID NO: 2), AP1/2β (SEQ ID NO: 3) or dynamin (SEQ ID NO: 4) polypeptide, or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for antibody titer. If desired, the mammal can be boosted until the antibody titer increases or plateaus.

2. Monoclonal Antibodies

The antibodies used in the practice of the invention may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. An example of such a murine myeloma cell line is P3X63AgU.1. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, Marcel Dekker, Inc., New York, (1987) pp. 51-63).

The culture medium in which the hybridoma cells are cultured can then be assayed for the presence of monoclonal antibodies directed against the desired immunogen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods (Goding, supra). Suitable culture media for this purpose include, for example, Dulbecco's Modified Eagle's Medium or RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies used in the practice of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody. Optionally, chimeric antibodies can be constructed which include at least one variable or hypervariable domain of an antibody such as one of the antibodies disclosed herein.

Optionally, the antibodies of the present invention will bind to the same epitope(s) as any of the antibodies disclosed herein. This can be determined by conducting various assays, such as described herein. For instance, to determine whether a monoclonal antibody has the same specificity as the antibodies specifically referred to herein, one can compare its activity in apoptosis assays.

The antibodies used in the practice of the invention include "cross-linked" antibodies. The term "cross-linked" as used herein refers to binding of at least two IgG molecules together to form one (or single) molecule. The antibodies may be cross-linked using various linker molecules. Optionally the antibodies are cross-linked using an anti-IgG molecule, complement, chemical modification or molecular engineering. It is appreciated by those skilled in the art that complement has a relatively high affinity to antibody molecules once the antibodies bind to cell surface membrane. Accordingly, it is believed that complement may be used as a cross-linking molecule to link two or more antibodies bound to cell surface membrane. Among the various murine Ig isotypes, IgM, IgG2a and IgG2b are known to fix complement.

The antibodies used in the practice of the invention may optionally comprise dimeric antibodies, as well as multivalent forms of antibodies. Those skilled in the art may construct such dimers or multivalent forms by techniques known in the art and using the anti-Apo-2L receptor antibodies herein.

The antibodies used in the practice of the invention may also comprise monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields an $F(ab')_2$ fragment that has two antigen combining sites and is still capable of cross-linking antigen.

The Fab fragments produced in the antibody digestion also contain the constant domains of the light chain and the first constant domain ($CH_1$) of the heavy chain. Fab' fragments differ from Fab fragments by the addition of a few residues at the carboxy terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

Single chain Fv fragments may also be produced, such as described in Iliades et al., *FEBS Letters*, 409:437-441 (1997). Coupling of such single chain fragments using various linkers is described in Kortt et al., *Protein Engineering*, 10:423-433 (1997).

In addition to the antibodies described above, it is contemplated that chimeric or hybrid antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

Antibodies used in the practice of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., *Nature*, 321:522-525 (1986); Riechmann et al., *Nature*, 332:323-329 (1988); and Presta, *Curr. Op. Struct. Biol.*, 2:593-596 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., *J. Immunol.*, 151:2296-2308 (1993); Chothia and Lesk, *J. Mol. Biol.*, 196:901-917 (1987)). Another method uses a particular framework derived from the consensus sequence of all human antibodies of a particular subgroup of light or heavy chains. The same framework may be used for several different humanized antibodies (Carter et al., *Proc. Natl. Acad. Sci. USA*, 89:4285-4289 (1992); Presta et al., *J. Immunol.*, 151:2623-2632 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679 published 3 Mar. 1994).

Human monoclonal antibodies may be made via an adaptation of the hybridoma method first described by Kohler and Milstein by using human B lymphocytes as the fusion partner. Human B lymphocytes producing an antibody of interest may, for example, be isolated from a human individual, after obtaining informed consent. For instance, the individual may be producing antibodies against an autoantigen as occurs with certain disorders such as systemic lupus erythematosus (Shoenfeld et al. *J. Clin. Invest.*, 70:205 (1982)), immune-mediated thrombocytopenic purpura (ITP) (Nugent et al. *Blood*, 70(1):16-22 (1987)), or cancer. Alternatively, or additionally, lymphocytes may be immunized in vitro. For instance, one may expose isolated human peripheral blood lymphocytes in vitro to a lysomotrophic agent (e.g. L-leucine-O-methyl ester, L-glutamic acid dimethly ester or L-leucyl-L-leucine-O-methyl ester) (U.S. Pat. No. 5,567,610, Borrebaeck et al.); and/or T-cell depleted human peripheral blood lymphocytes may be treated in vitro with adjuvants such as 8-mercaptoguanosine and cytokines (U.S. Pat. No. 5,229,275, Goroff et al.).

The B lymphocytes recovered from the subject or immunized in vitro, are then generally immortalized in order to generate a human monoclonal antibody. Techniques for immortalizing the B lymphocyte include, but are not limited to: (a) fusion of the human B lymphocyte with human, murine myelomas or mouse-human heteromyeloma cells; (b) viral transformation (e.g. with an Epstein-Barr virus; see Nugent et al., supra, for example); (c) fusion with a lymphoblastoid cell line; or (d) fusion with lymphoma cells.

Lymphocytes may be fused with myeloma cells using a suitable fusing agent, such as polyethylene glycol, to form a hybridoma cell (Goding, *Monoclonal Antibodies: Principles and Practice*, pp. 59-103 (Academic Press, 1986)). The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Suitable human myeloma and mouse-human heteromyeloma cell lines have been described (Kozbor, *J. Immunol.*, 133:3001 (1984); Brodeur et al., *Monoclonal Antibody Production Techniques and Applications*, pp. 51-63 (Marcel Dekker, Inc., New York, 1987)). Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. The monoclonal antibodies secreted by the subclones are suitably separated from the culture medium, ascites fluid, or serum by conventional immunoglobulin purification procedures such as, for example, protein A chromatography, gel electrophoresis, dialysis, or affinity chromatography.

Human antibodies may also be generated using a non-human host, such as a mouse, which is capable of producing human antibodies. As noted above, transgenic mice are now available that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); U.S. Pat. Nos. 5,591,669; 5,589,369; and 5,545,807. Human antibodies may also be prepared using SCID-hu mice (Duchosal et al. *Nature* 355:258-262 (1992)).

In another embodiment, the human antibody may be selected from a human antibody phage display library. The preparation of libraries of antibodies or fragments thereof is well known in the art and any of the known methods may be used to construct a family of transformation vectors which may be introduced into host cells. Libraries of antibody light and heavy chains in phage (Huse et al., *Science*, 246:1275 (1989)) or of fusion proteins in phage or phagemid can be prepared according to known procedures. See, for example, Vaughan et al., *Nature Biotechnology* 14:309-314 (1996); Barbas et al., *Proc. Natl. Acad. Sci., USA*, 88:7978-7982 (1991); Marks et al., *J. Mol. Biol.*, 222:581-597 (1991); Hoogenboom and Winter, *J. Mol. Biol.*, 227:381-388 (1992); Barbas et al., *Proc. Natl. Acad. Sci., USA*, 89:4457-4461 (1992); Griffiths et al., *EMBO Journal*, 13:3245-3260 (1994); de Kruif et al., *J. Mol. Biol.*, 248:97-105 (1995); WO 98/05344; WO 98/15833; WO 97/47314; WO 97/44491; WO 97/35196; WO 95/34648; U.S. Pat. Nos. 5,712,089; 5,702,892; 5,427,908; 5,403,484; 5,432,018; 5,270,170; WO 92/06176; WO 99/06587; U.S. Pat. No. 5,514,548; WO97/08320; and U.S. Pat. No. 5,702,892. The antigen of interest is panned against the phage library using procedures known in the field for selecting phage-antibodies which bind to the target antigen.

The antibodies as described herein, will optionally possess one or more desired biological activities or properties. Such antibodies may include but are not limited to chimeric, humanized, human, and affinity matured antibodies. As described above, the antibodies may be constructed or engineered using various techniques to achieve these desired activities or properties. In one embodiment, the antibody will have a binding affinity of at least $10^5$ $M^{-1}$, preferably at least in the range of $10^6$ $M^{-1}$ to $10^7$ $M^{-1}$, more preferably, at least in the range of $10^8$ $M^{-1}$ to $10^{12}$ $M^{-1}$ and even more preferably, at least in the range of $10^9$ $M^{-1}$ to $10^{12}$ $M^{-1}$. The binding affinity of the antibody can be determined without undue experimentation by testing the antibody in accordance with techniques known in the art, including Scatchard analysis (see Munson et al., supra).

In another embodiment, the antibody of the invention may bind the same epitope to which the antibodies disclosed herein bind, or bind an epitope which coincides or overlaps with the epitope to which the antibodies disclosed herein bind. The epitope binding property of the antibody of the present invention may be determined using techniques known in the art. For instance, the antibody may be tested in an in vitro assay, such as a competitive inhibition assay, to determine the ability of the antibody to block or inhibit a known binding interaction.

3. Bispecific Antibodies

Bispecific antibodies are monoclonal, preferably human or humanized, antibodies that have binding specificities for at least two different antigens. Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature*, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.,* 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology,* 121:210 (1986).

4. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

5. Triabodies

Triabodies are also within the scope of the invention. Such antibodies are described for instance in Iliades et al., supra and Kortt et al., supra.

6. Other Modifications

Other modifications of antibodies are contemplated herein. Certain antibodies useful in methods of the present invention may be modified by conjugating the antibody to a cytotoxic agent (like a toxin molecule) or a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278. This technology is also referred to as "Antibody Dependent Enzyme Mediated Prodrug Therapy" (ADEPT).

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; caspases such as caspase-3; D-alanylcarboxypeptidases, useful for converting prodrugs that contain D-amino acid substituents; carbohydrate-cleaving enzymes such as beta-galactosidase and neuraminidase useful for converting glycosylated prodrugs into free drugs; beta-lactamase useful for converting drugs derivatized with beta-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The enzymes can be covalently bound to the antibodies by techniques well known in the art such as the use of heterobifunctional crosslinking reagents. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature,* 312: 604-608 (1984).

As is known in the art, antibodies such as those used in immunoassays to detect a protein fragment of AP2-α (SEQ ID NO: 1), clathrin heavy chain (SEQ ID NO: 2), AP1/2β (SEQ ID NO: 3) or dynamin (SEQ ID NO: 4); can be conjugated to a variety of imaging agents. Conjugation may be accomplished directly between the antibody and the imaging agent or linking, or intermediate molecular groups may be provided between the antibody and the active agent. Crosslinkers often used facilitate conjugation by providing attachment sites for each moiety. Crosslinkers may include additional molecular groups which serve as spacers to separate the moieties from each other to prevent either from interfering with the activity of the other.

Imaging can be performed by many procedures well-known to those having ordinary skill in the art and the appropriate imaging agent useful in such procedures may be conjugated to an antibody by well-known means. Imaging can be performed, for example, by visualizing the results of a Western procedure, by radioscintigraphy, nuclear magnetic resonance imaging (MRI) or computed tomography (CT scan). Commonly employed radionuclide imaging agents include radioactive iodine and indium. Imaging by CT scan may employ a heavy metal such as iron chelates. MRI scanning may employ chelates of gadolinium or manganese. Additionally, positron emission tomography (PET) is possible using positron emitters of oxygen, nitrogen, iron, carbon, or gallium. Examples of radionuclides useful in imaging procedures include: $^{43}$K, $^{52}$Fe, $^{57}$Co, $^{67}$Cu, $^{67}$Ga, $^{68}$Ga, $^{77}$Br, $^{81}$Rb, $^{111}$In, $^{113}$In, $^{123}$I, $^{125}$I, $^{127}$Cs, $^{129}$Cs, $^{131}$I, $^{132}$I, $^{197}$Hg, $^{203}$Pb and $^{206}$Bi.

Magerstadt, M. (1991) Antibody Conjugates And Malignant Disease, CRC Press, Boca Raton, Fla., and Barchel, S. W. and Rhodes, B. H., (1983) Radioimaging and Radiotherapy, Elsevier, NY, N.Y., each of which is incorporated herein by reference, teach the conjugation of various therapeutic and diagnostic radionuclides to amino acids of antibodies. Such reactions may be applied to conjugate radionuclides to antibodies with an appropriate linker. Suitable labels include, for example, radionuclides, enzymes (e.g. horse radish peroxidase), substrates, cofactors, inhibitors, fluorescers, chemiluminescers, and/or magnetic particles. See, for examples of patents teaching the use of such labels, U.S. Pat. Nos. 3,817,837; 3,850,752; 3,939,350; 3,996,345; 4,277,437; 4,275,149; and 4,366,241, all of which are incorporated by reference.

Further antibody modifications are also contemplated. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* 16th edition, Oslo, A., Ed., (1980). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

7. Recombinant Methods

The invention also provides isolated nucleic acids encoding a polypeptide of interest, for example the proteins, protein fragments (e.g. protein fragment of AP2-α (SEQ ID NO: 1), clathrin heavy chain (SEQ ID NO: 2), AP1/2β (SEQ ID NO: 3) or dynamin (SEQ ID NO: 4)) and/or antibodies as disclosed herein, vectors and host cells comprising the nucleic acid, and recombinant techniques for the production of a polypeptide of interest.

For recombinant production of the polypeptide of interest, the nucleic acid encoding it is isolated and inserted into a replicable vector for further cloning (amplification of the DNA) or for expression. DNA encoding the polypeptide of interest is readily isolated and sequenced using conventional procedures (e.g., by using oligonucleotide probes that are capable of binding specifically to genes encoding the polypeptide of interest). Many vectors are available. The vector components generally include, but are not limited to, one or more of the following: a signal sequence, an origin of replication, one or more marker genes, an enhancer element, a promoter, and a transcription termination sequence.

The methods herein include methods for the production of chimeric or recombinant antibodies which bind a protein fragment of AP2-α (SEQ ID NO: 1), clathrin heavy chain (SEQ ID NO: 2), AP1/2β (SEQ ID NO: 3) or dynamin (SEQ ID NO: 4) and which comprise the steps of providing a vector comprising a DNA sequence encoding the antibody light chain or heavy chain (or both a light chain and a heavy chain), transfecting or transforming a host cell with the vector, and culturing the host cell(s) under conditions sufficient to produce the recombinant product.

(i) Signal Sequence Component

An polypeptide of interest may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, α factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the polypeptide of interest.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding the polypeptide of interest, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

(iv) Promoter Component

Expression and cloning vectors usually contain a promoter that is recognized by the host organism and is operably linked to the nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the polypeptide of interest.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the Rous sarcoma virus long terminal repeat can be used as the promoter.

(v) Enhancer Element Component

Transcription of a DNA encoding a polypeptide of interest by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the coding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding a multivalent antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 April 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida*; *Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of polypeptides of interest are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; a human hepatoma line (Hep G2); and myeloma or lymphoma cells (e.g. Y0, J558L, P3 and NS0 cells) (see U.S. Pat. No. 5,807,715).

Host cells are transformed with the above-described expression or cloning vectors for production of the polypeptide of interest and cultured in conventional nutrient media modified as appropriate for inducing promoters, selecting transformants, or amplifying the genes encoding the desired sequences.

(viii) Culturing the Host Cells

The host cells used to produce the polypeptide of interest may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification

When using recombinant techniques, the polypeptide of interest can be produced intracellularly, in the periplasmic space, or directly secreted into the medium. If the polypeptide of interest is produced intracellularly, as a first step, the particulate debris, either host cells or lysed fragments, is removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the polypeptide of interest is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc region that is present in antibodies. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the polypeptide of interest to be recovered.

III. Articles of Manufacture

In another embodiment of the invention, an article of manufacture containing materials useful for the practice of embodiments of the methods described above are provided. The article of manufacture comprises a container and a label. Suitable containers include, for example, bottles, vials, syringes, and test tubes. The containers may be formed from a variety of materials such as glass or plastic. The container holds a composition which is effective for observing apoptosis and may have a sterile access port (for example the container may be an intravenous solution bag or a vial having a stopper pierceable by a hypodermic injection needle). Typical agents in the composition include one or more antibodies that bind a protein fragment of AP2-α (SEQ ID NO: 1), clathrin heavy chain (SEQ ID NO: 2), AP1/2β (SEQ ID NO: 3) or dynamin (SEQ ID NO: 4). The label on, or associated with, the container indicates that the composition is used for observing apoptosis and/or assessing the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

In one such embodiment, the present invention provides kits which may be used in the detection of cell apoptosis and in the diagnosis of diseases associated therewith. One such kit comprises: (1) a primary antibody capable of binding to a protein fragment generated during apoptosis, (2) a secondary antibody conjugated to a signal-producing label, the secondary antibody being one which binds to the primary antibody; and (3) a signal-producing tertiary reagent capable of recognizing a tagged secondary antibody. Another kit that is useful for detection of apoptosis-generated protein fragments according to the present invention includes (1) a first antibody capable of binding to protein fragments generated during apoptosis; and (2) a second antibody conjugated to a signal-producing label, the second antibody also being reactive with an apoptosis-generated protein fragment, but one that binds to a site different from that to which the first antibody binds.

In embodiments of kits of the present invention, the signal-producing label linked to the secondary antibody may be, for example, an enzyme, such as horseradish peroxidase or alkaline phosphatase. Preferably, both the enzyme and the substrate are provided in the kit. The kit may also include an uncoated support onto which a sample to be assayed, or the first antibody, can be immobilized.

IV. USING METHODS AND MATERIALS OF THE INVENTION TO EXAMINE CELLULAR PROCESSES ASSOCIATED WITH APOPTOSIS

The methods and materials of the invention can be used to examine a wide variety of cellular processes such as endocytosis. Certain embodiments of the invention for example observe changes in the rate of cellular endocytosis as an indicator of apoptosis, with an inhibition in endocytosis providing evidence of apoptosis. Endocytosis is crucial for various aspects of cell homeostasis. Endocytosis internalizes plasma membrane (PM)-associated proteins through membrane-bound vesicles, supporting various cellular functions including nutrient uptake, growth-factor signaling, and membrane homeostasis (see, e.g., Conner, S. D. et. al., *Nature* 422, 37-44 (2003)). One of the best-characterized endocytosis pathways relies on the protein clathrin (see, e.g., Bonifacino, J. S. et. al., *Annu Rev Biochem* 72, 395-447 (2003)). Clathrin adaptors, such as adaptor protein 2 (AP2), link clathrin to cytoplasmic determinants of endocytic cargo during the formation of PM invaginations known as clathrin-coated pits. Adaptors also perform scaffolding functions in endocytosis by recruiting accessory or regulatory proteins (see, e.g., Owen, D. J., et. al, P. R. *Annu Rev Cell Dev Biol* 20, 153-91 (2004)). GTP hydrolysis by dynamin drives the scission of deeply invaginated coated pits to release endocytic transport vesicles from the PM. After uncoating, the vesicles dock and fuse with early endosomes, where cargo sorts to different fates, e.g., tubulo-vesicular endosomal membranes for recycling to the PM, or internal membranes of multivesicular late-endosomes for lysosomal degradation.

Using methods and materials of the invention it is shown that pro-apoptotic death receptors (DRs) trigger selective destruction of the clathrin-dependent endocytosis machinery. DR stimulation induced rapid, caspase-mediated cleavage of key clathrin-pathway components, halting cellular uptake of the classic cargo protein transferrin. DR-proximal initiator caspases cleaved the clathrin adaptor subunit AP2α between functionally distinct domains, while effector caspases processed clathrin's heavy-chain. DR5 is shown to undergo ligand-induced clathrin-mediated endocytosis, providing evidence that internalization of DR signaling complexes facilitates clathrin-pathway targeting by caspases. An endocytosis-blocking, temperature-sensitive dynamin-1 mutant attenuated DR internalization, enhanced caspase stimulation downstream of DRs and increased apoptosis. Thus, DR-triggered caspase activity disrupts clathrin-dependent endocytosis, leading to amplification of programmed cell death.

Further illustrative applications of the methods and materials of the invention are described below.

Figure 7:
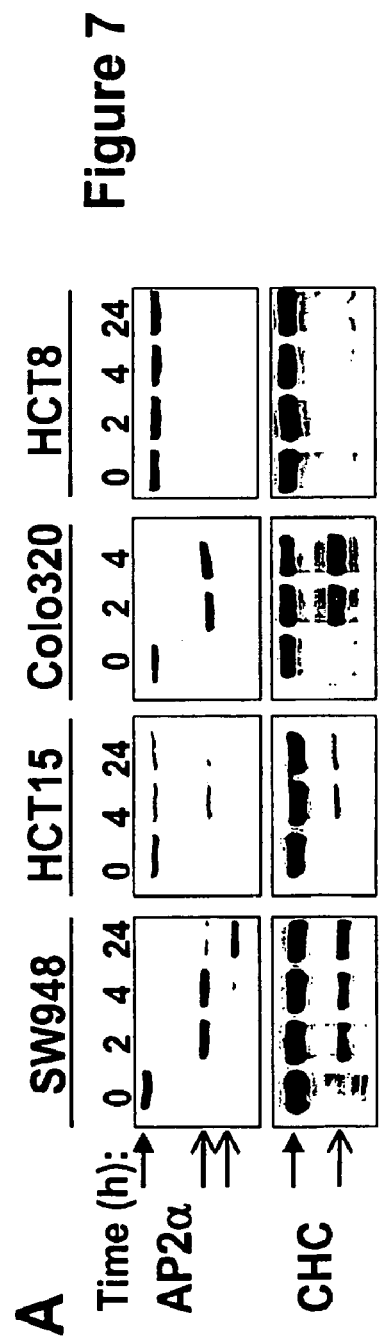
FIG. 7 shows the processing of clathrin-pathway components in cancer cell lines. (a) The indicated cell lines were treated with Apo2L/TRAIL and cleavage of AP2α or CHC was analyzed by immunoblot. (b) BJAB cells were treated with crosslinked Apo2L/TRAIL or FasL and processing of AP2α or CHC was analyzed by immunoblot. (c) BJAB cells were treated with crosslinked Apo2L/TRAIL and processing of dynamin was determined by immunoblot.
Figure 7:
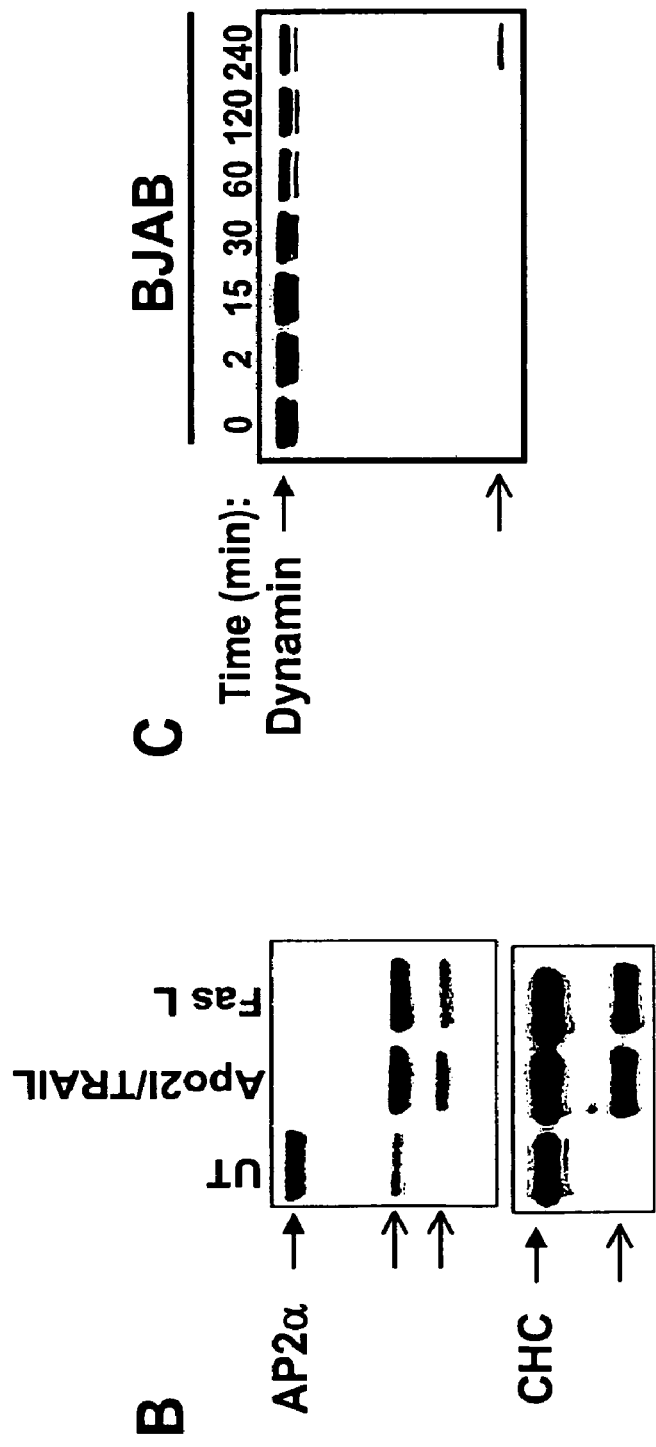

DR Activation Induces Caspase-Mediated Cleavage of the Clathrin-Dependent Endocytosis Machinery In studies on DR5 endocytosis, it was observed that the DR5 ligand Apo2L/TRAIL triggered proteolytic cleavage of the α subunit of AP2 (AP2α). Analysis of several cancer cell lines showed that Apo2L/TRAIL promoted not only the expected processing of caspase-8 and -3, but also cleavage of AP2α, AP1/2β, and clathrin heavy-chain (CHC) (FIG. 1a). These events occurred within 2 hr, and were restricted to cell lines susceptible to Apo2L/TRAIL-induced apoptosis, such as Colo205, BJAB, and HeLa-M, compared to resistant cell lines, such as HCT8 (FIG. 1a). Additional cell lines confirmed this observation (FIG. 7a). FasL stimulated cleavage of AP2α and CHC in BJAB cells comparably to Apo2L/TRAIL (FIG. 7b). Apo2L/TRAIL also induced cleavage of dynamin, leading to depletion of the full-length protein that started within 1 hr of stimulation (FIG. 7c). In a similar timeframe, Apo2L/TRAIL did not induce proteolysis of structurally analogous adaptors that mediate other types of clathrin-dependent vesicular transport events (FIG. 1b). These included AP1α, AP3β and δ, and AP4ε, which support transport between the trans-Golgi network and endosomes, and the COP-I subunit β-COP or the COP-II subunit Sec23, which mediate transport between endoplasmic reticulum and Golgi (see, e.g., Bonifacino, J. S. et. al., *Annu Rev Biochem* 72, 395-447 (2003) and McMahon, H. T. et. al., *Curr Opin Cell Biol* 16, 379-91 (2004)). Hence, DR activation promotes rapid and specific cleavage of proteins involved in clathrin-dependent endocytosis.

Figure 8:
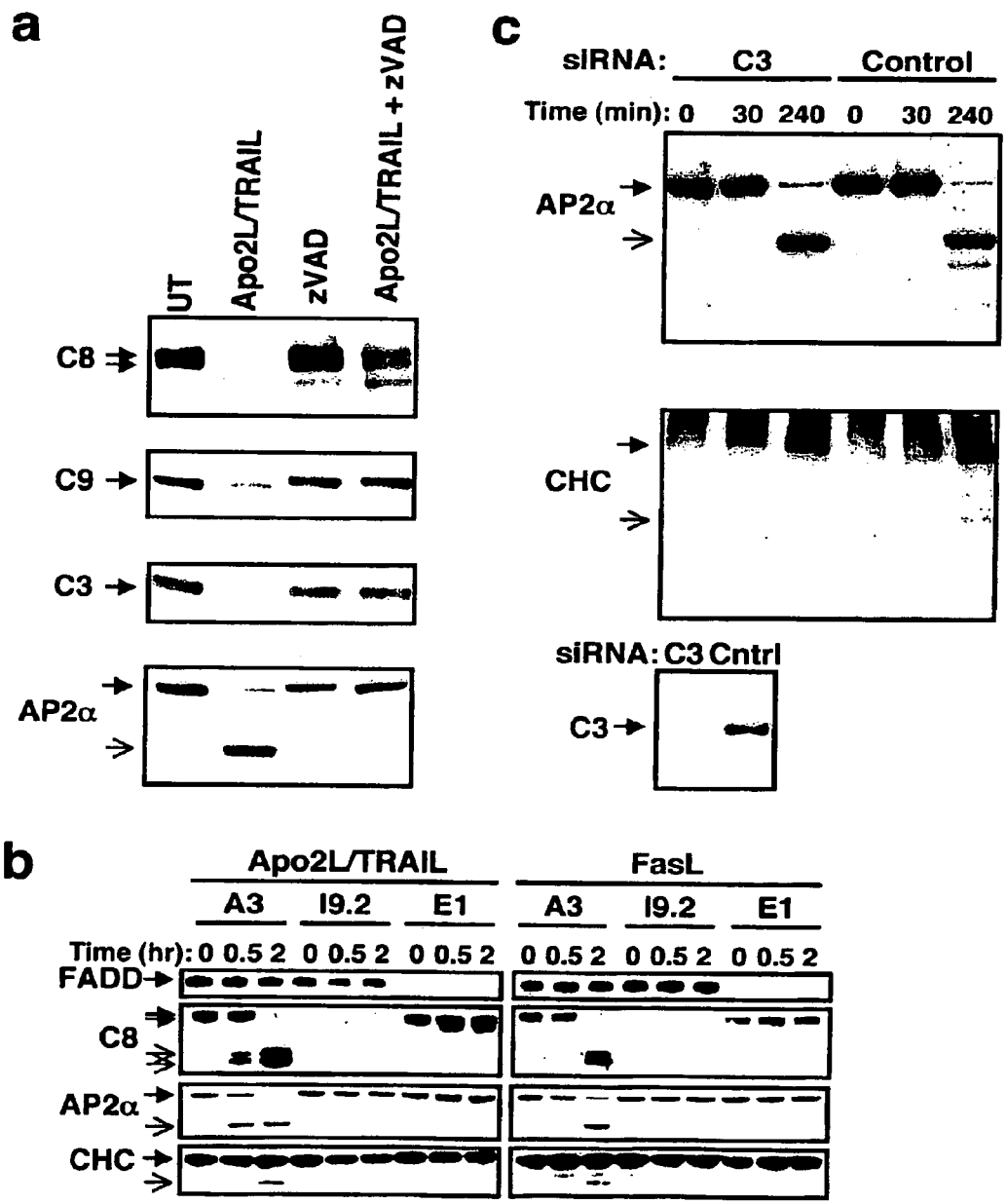
FIG. 8 shows the Caspase requirement for AP2α and CHC cleavage. (a) BJAB cells were preincubated with or without zVAD-fmk (20 uM, 30 min) and treated with crosslinked Apo2L/TRAIL (1 μg/mL) as indicated for 24 h. The cells were analyzed by immunoblot for processing of caspase-8, caspase-9, caspase-3, and AP2α. (b) The following Jurkat T cell lines: A3 (wt), I9.2, (caspase-8-deficient) and E1 (FADD-deficient) were treated with crosslinked Apo2L/TRAIL or FasL for the indicated time and analyzed for processing of components of the clathrin-mediated endocytosis pathway as in FIG. 1. (c) HT1080 fibrosarcoma cells were transfected with caspase-3-specific siRNA (C3) or control siRNA, treated with Apo2L/TRAIL for the indicated time, and analyzed by immunoblot for cleavage of AP2α or CHC or for siRNA depletion of caspase-3.

Pretreatment with the pan-caspase inhibitor N-benzyloxycarbonyl-Val-Ala-Asp-fluoromethylketone (zVAD-fmk) at a dose that inhibited ligand-induced processing of caspase-8 and -3 prevented cleavage of AP2α and CHC (FIG. 2a), as well as of AP2α in BJAB cells (FIG. 8a), indicating a requirement for caspase activity. Furthermore, while Apo2L/TRAIL and FasL induced cleavage of AP2α and CHC in wt Jurkat T cells, neither ligand stimulated processing of these targets in caspase-8-deficient or FADD-deficient mutant Jurkat cell lines (FIG. 8b). AP2α cleavage was fast and correlated in time with caspase-8 processing while it preceded caspase-3 processing (FIG. 1a). By contrast, CHC cleavage was relatively slower and correlated better in timing with caspase-3 processing. In HCT116 cells, caspase-3 activation and apoptosis induction by Apo2L/TRAIL require Bax, while caspase-8 stimulation does not (see, e.g., LeBlanc, H. N. et. al., *Cell Death Differ* 10, 66-75 (2003). As expected, Apo2L/TRAIL stimulated processing of both caspase-8 and -3 in Bax$^{+/-}$ HCT116 cells, but only of caspase-8 in Bax$^{-/-}$ HCT116 cells (FIGS. 2b, c). AP2α cleavage was independent of Bax, whereas CHC cleavage required Bax (FIGS. 2b, c). In MCF7 cells, which are deficient in caspase-3, Apo2L/TRAIL induced relatively weak and slow processing of caspase-8 and AP2α, but did not stimulate CHC cleavage (FIG. 2d) (see, e.g., Kischkel, F. C. et al., *Immunity* 12, 611-20 (2000)). Furthermore, siRNA knockdown of caspase-3 in HT1080 cells blocked ligand-induced processing of CHC but not of AP2α (FIG. 8c). These findings provide evidence that initiator caspases in the DR pathway cleave AP2α, while effector caspases process CHC.

Figure 9:
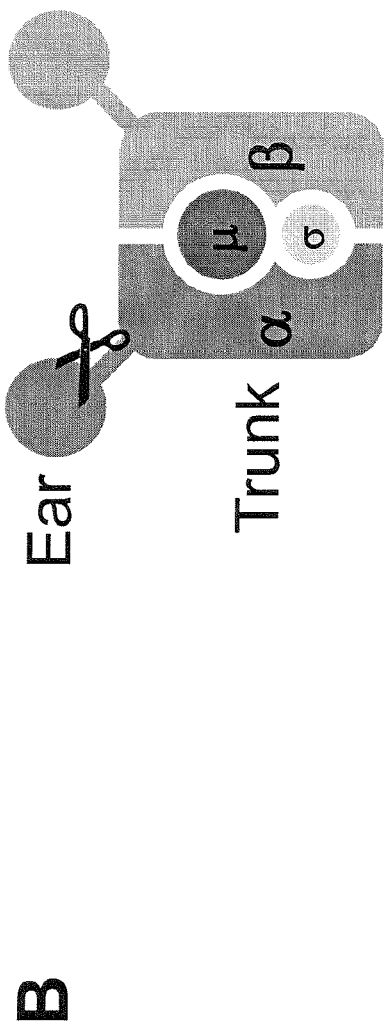
FIG. 9 Determination of the AP2α cleavage site. (a) The C-terminal fragment of cleaved AP2α was immunoprecipitated from Apo2L/TRAIL-stimulated BJAB cells and either digested with trypsin and analyzed by mass spectrometry to verify its identity or isolated by gel electrophoresis and Western transfer and subjected to N-terminal sequencing. Tryptic peptides identified by tandem mass spectrometry align with the AP2α C-terminal sequence. N-terminal sequencing identifies the cleavage site as a DXXD caspase recognition motif (underlined). (b) The cleavage site maps to the 'hinge' region of AP2α, which couples the functionally distinct 'ear' and 'trunk' domains.

AP2α contains two major functional parts, linked by a 'hinge' region: the C-terminal 'ear' and N-terminal 'trunk' domains (see, e.g., Owen, D. J., et. al, P. R. *Annu Rev Cell Dev Biol* 20, 153-91 (2004)). To define the primary site of AP2α cleavage, the C-terminal 33 kDa cleavage product was immunopurified from BJAB cells and the identity of its tryptic peptides by mass spectrometry was confirmed (FIG. 9a). N-terminal sequencing revealed GPAAQPSLGPTPEEAFLS residues 688 to 705 of SEQ ID NO: 1, a sequence immediately upstream from DVFD residues 684 to 687 of SEQ ID NO: 1 (FIG. 9a), a tetrapeptide sequence that resembles well-characterized caspase recognition sites (see, e.g., Stennicke, H. R., et. al, *Biochem J* 350 Pt 2, 563-8 (2000)). The cleavage site has Asp and Gly at respective P1 and P1' positions flanking the scissile bond, and an Asp at the P4 position, which caspase-8 tolerates well (see, e.g., Blanchard, H. et al. *J Mol Biol* 302, 9-16 (2000)). While this tetrapeptide cleavage site sequence is present in isoform A of AP2α, it is absent in isoform C. Consistent with this difference, Apo2L/TRAIL did not induce cleavage of isoform C, which was much less abundant than isoform A, in BJAB, Colo205, LS1034 and SW948 cells. This AP2α cleavage site resides within the hinge (FIG. 9b), providing evidence that its hydrolysis may disrupt AP2 function. Longer ligand stimulation of certain cell lines led to further processing of AP2α at a secondary site, which appeared to be within the initial 33 kDa fragment (FIGS. 7a and b).

Figure 3:
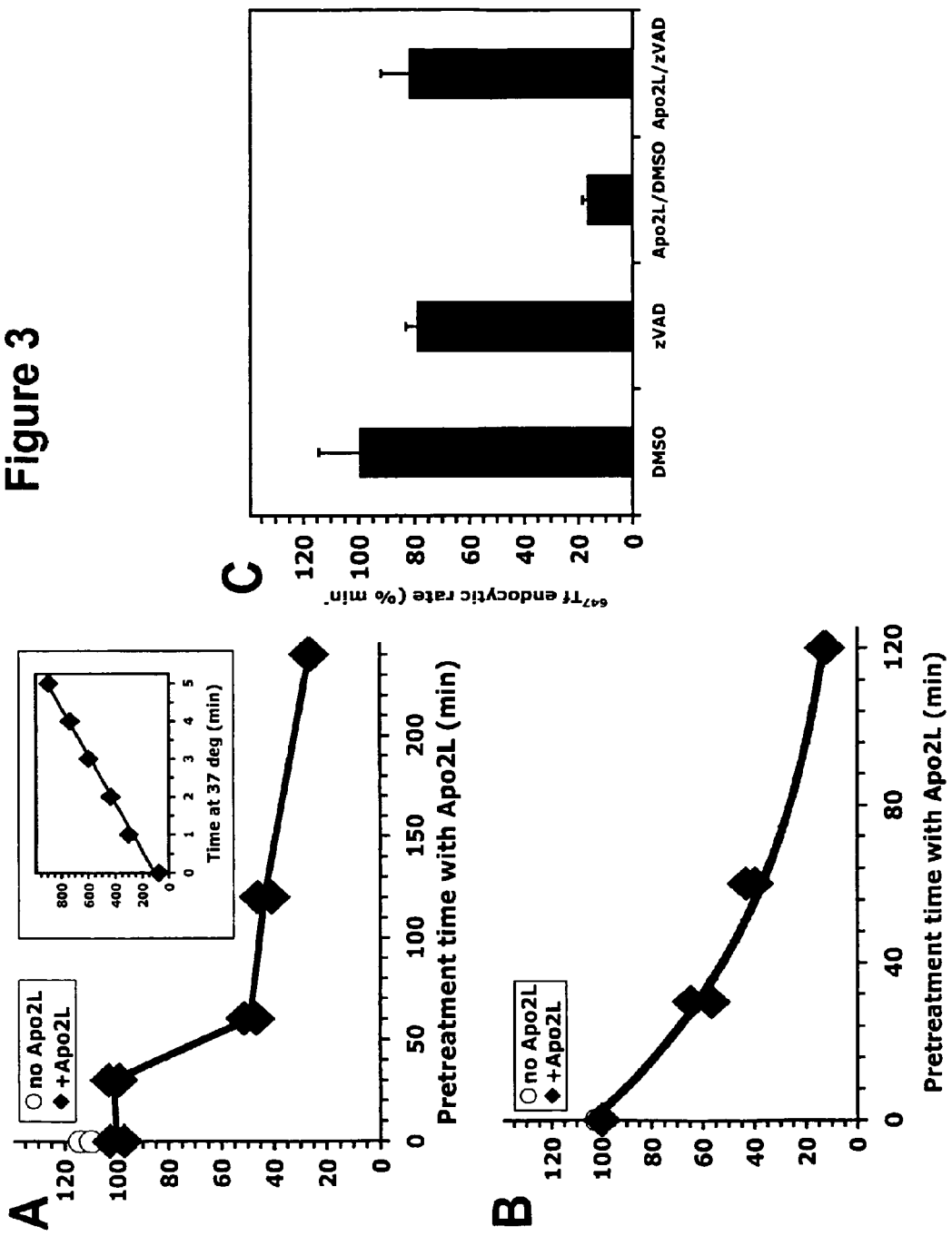
FIG. 3 shows that Apo2L/TRAIL pretreatment inhibits Tf endocytosis. (a, b) BJAB (a) or Colo205 (b) cells were pretreated at 37° C. with or without crosslinked (a) or non-crosslinked (b) Apo2L/TRAIL for the indicated times and chilled on ice. The cells were then equilibrated on ice for 30 min with Alexa-647-conjugated Tf ($^{647}$TF) and uptake at 37° C. was measured by flow cytometry. Each endocytosis rate was derived from the slope of the initial linear phase of a 4 min uptake kinetics plot (a, inset). Rates were normalized to that observed in the absence of Apo2L/TRAIL (white circles), which was comparable to that observed when ligand was excluded from the pre-incubation step but present during the Tf incubation phase of the assay (black diamonds, 0 min). (c) BJAB cells were pre-exposed to DMSO vehicle or zVAD-fmk for 30 min, then treated for 4 hr with crosslinked Apo2L/ TRAIL, chilled on ice, and analyzed for $^{647}$Tf endocytosis rates as in a and b. Rates were normalized to the DMSO treated sample (±SEM).

To assess the functional consequence of these caspase-mediated cleavage events, the uptake of transferrin (Tf) was studied. Internalization of receptor-bound Tf occurs via clathrin-coated pits and strictly requires AP2 (see, e.g., Bonifacino, J. S. et. al., *Annu Rev Biochem* 72, 395-447 (2003)). To determine the endocytosis rate of fluorescent-labeled Tf, the measurements were confined to the initial, linear phase of uptake, before internalized protein undergoes endocytic recycling to the PM (FIG. 3a, inset). Apo2L/TRAIL inhibited the rate of Tf endocytosis in BJAB and Colo205 cells by 75-85% (FIG. 3a, b); pretreatment with zVAD-fmk substantially reversed this inhibition (FIG. 3c). Hence, DR activation leads to caspase-dependent disruption of clathrin-mediated endocytosis.

Apo2L/TRAIL Induces Clathrin-Mediated DR5 Endocytosis

Figure 4:
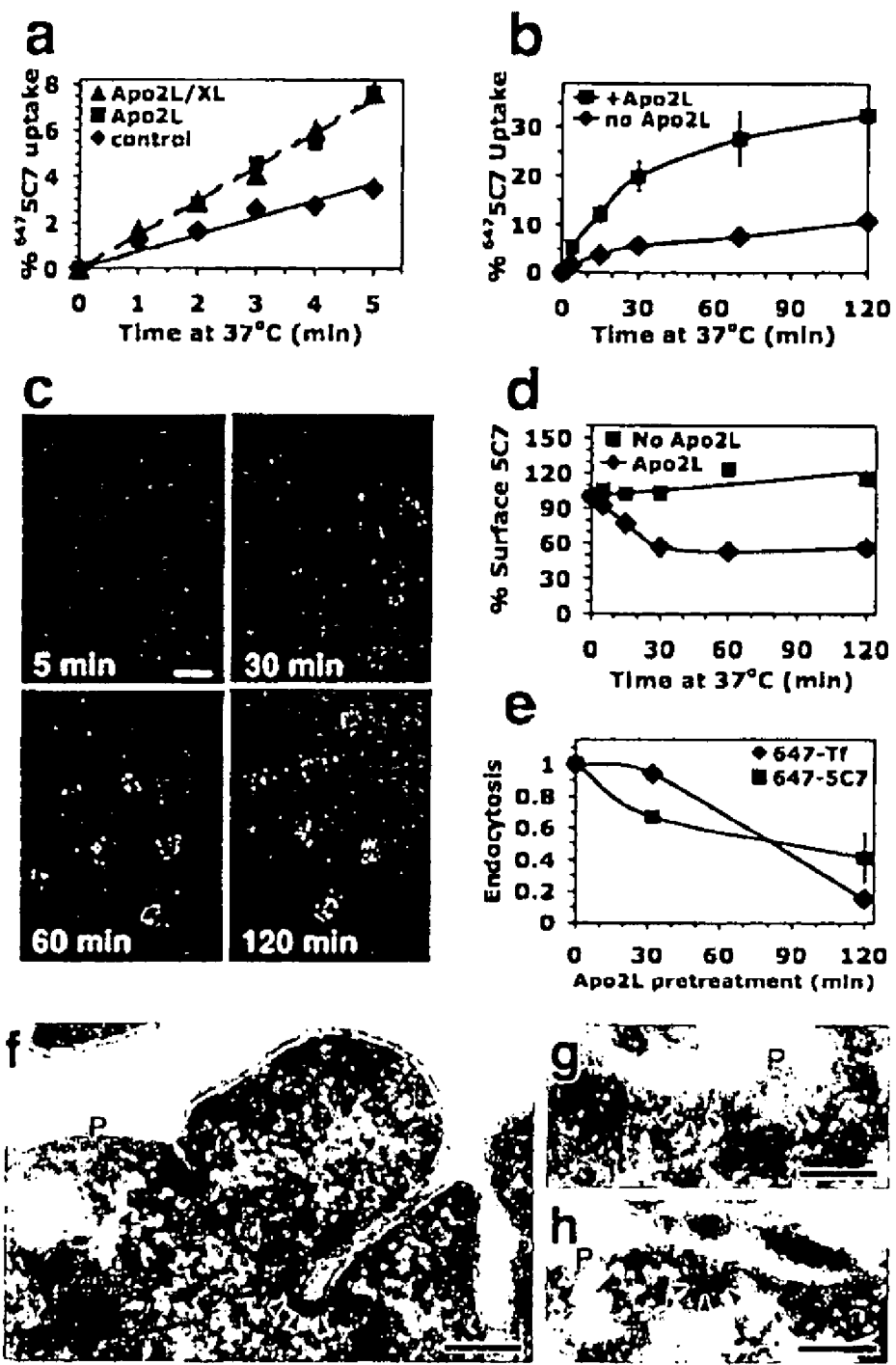
FIG. 4 provides a characterization of DR5 endocytosis. (a, b) Colo205 cells with surface-bound $^{647}$5C7 mAb were incubated on ice 30 min in the absence (diamonds) or presence of 10 ug/ml trimeric (squares) or crosslinked (triangles) Apo2L/TRAIL, then shifted to 37° C. for the indicated time and rapidly chilled on ice. Surface fluorescence was removed by acid stripping and DR5 uptake quantified by flow cytometry. Mean values were plotted (±SEM in b). (c) Hela-m cells were incubated at 37° C. with 5 μg/ml $^{647}$5C7 and 5 μg/ml crosslinked Apo2L/TRAIL, then processed for immunofluorescence microscopy (Bar: 20 μm). (d) Colo205 cells were pre-equilibrated at 37° C. with unlabeled mAb 5C7 for 30 min to bind surface and recycling DR5 pools. Incubations were continued with or without 10 μg/ml Apo2L/TRAIL and then cells were rapidly chilled on ice. Cell surface exposed mAb 5C7 was probed with CY5-anti-mouse IgG, quantified by flow cytometry, and means plotted (±SEM). (e) Colo205 cells were pretreated at 37° C. with 10 ug/ml Apo2L/TRAIL, then rapidly chilled on ice and assayed for endocytosis as in a ($^{647}$5C7) and FIG. 3b ($^{647}$Tf). Endocytosis rates were normalized to the value without Apo2L/TRAIL pretreatment (±SEM). Similar results were observed when cells were prepared as in c and endocytosis assayed with surface-bound CY5-anti-mouse Fab. (f-h) Colo205 cells with surface-bound mAb 5C7 were incubated on ice with Apo2L/TRAIL, shifted to 37° C. for 5 min and fixed. Ultrathin cryosections were labeled with rabbit anti-mouse IgG antibodies and Protein A gold (10 nm). The typical electron-dense clathrin coat is indicated by arrowheads. P, plasma membrane. Scale bars, 200 nm.

The rapid and selective cleavage of clathrin-pathway components provided evidence that physical proximity of DRs to clathrin coat proteins might facilitate the proteolytic events. Therefore, it was asked whether DR5 undergoes clathrin-mediated endocytosis upon ligand stimulation. A monoclonal antibody (mAb 5C7) was used that recognizes the receptor's extracellular domain without competing for ligand binding (see, e.g., Kischkel, F. C. et al., *Immunity* 12, 611-20 (2000)). Incubation with saturating amounts of 5C7 at 37° C. did not affect surface DR5 levels as detected by another, non-overlapping mAb, verifying that 5C7 itself does not alter DR5 endocytosis. A fluorescent conjugate of mAb 5C7 ($^{647}$5C7) was prepared, bound to Colo205 cells at 0° C., and followed to measure the kinetics of DR5 endocytosis at 37° C. (FIG. 4a). Exposure to trimeric or multimeric (antibody-crosslinked) forms of Apo2L/TRAIL similarly accelerated the rate of DR5 endocytosis by ~2-fold (FIG. 4a), leading to ~⅓ of the receptor internalizing over 2 hr, mostly within the initial 30 min (FIG. 4b). Correspondingly, cell-surface DR5 declined during the first 30 min of stimulation, after which this DR5 pool stabilized (FIG. 4c). Similar results were observed in BJAB cells. In contrast to data obtained upon brief exposure to ligand at 37° C. (FIG. 4a), extended exposure for 2 hr inhibited DR5 endocytosis concomitantly with that of Tf, reducing the rate by 2.5- or 5-fold, respectively (FIG. 4d). These results provide evidence that the clathrin pathway supports the endocytosis of DR5. Indeed in Colo205 cells briefly treated with Apo2L/TRAIL, a small fraction of the cell-surface 5C7 localized to clathrin-coated pits by electron microscopy (EM), with no detectable localization to non-coated surface invaginations or caveolae (FIG. 4f-h).

Figure 5:
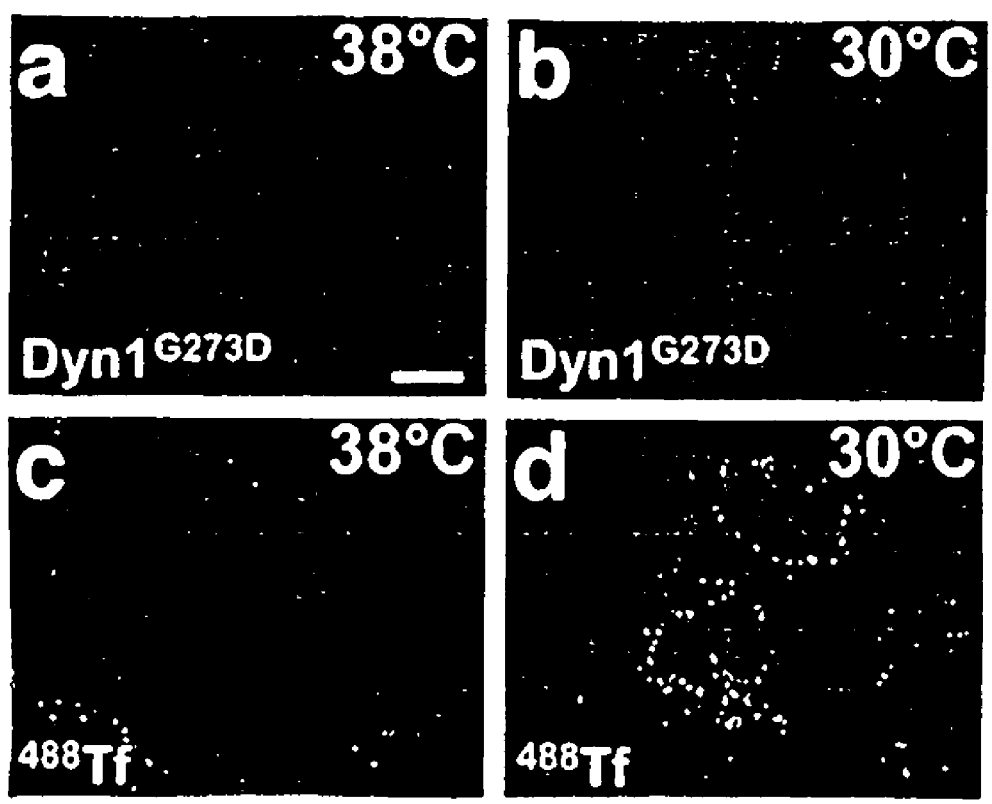
FIG. 5 shows that Dynamin inactivation inhibits DR5 endocytosis. (a-d) Dyn$^{G273D}$-transduced HeLa-M cells were puromycin-selected, doxycycline-induced, pre-incubated for 20 min at the indicated temperature, then incubated another 20 min in the presence of Alexa-488 conjugated Tf ($^{488}$Tf). Cells were then processed for immunofluorescence microscopy using a dynamin-1 specific antibody. (e, f) Nontransduced (parental) or clonal Dyn1$^{G273D}$-transduced BJAB cells with (+dox) or without (no dox) doxycycline induction were assayed for $^{488}$Tf or $^{647}$5C7 uptake over a 20 min period at 30° C. (white bars) or 38° C. (black bars) by flow cytometry and means plotted (±SD).
Figure 10:
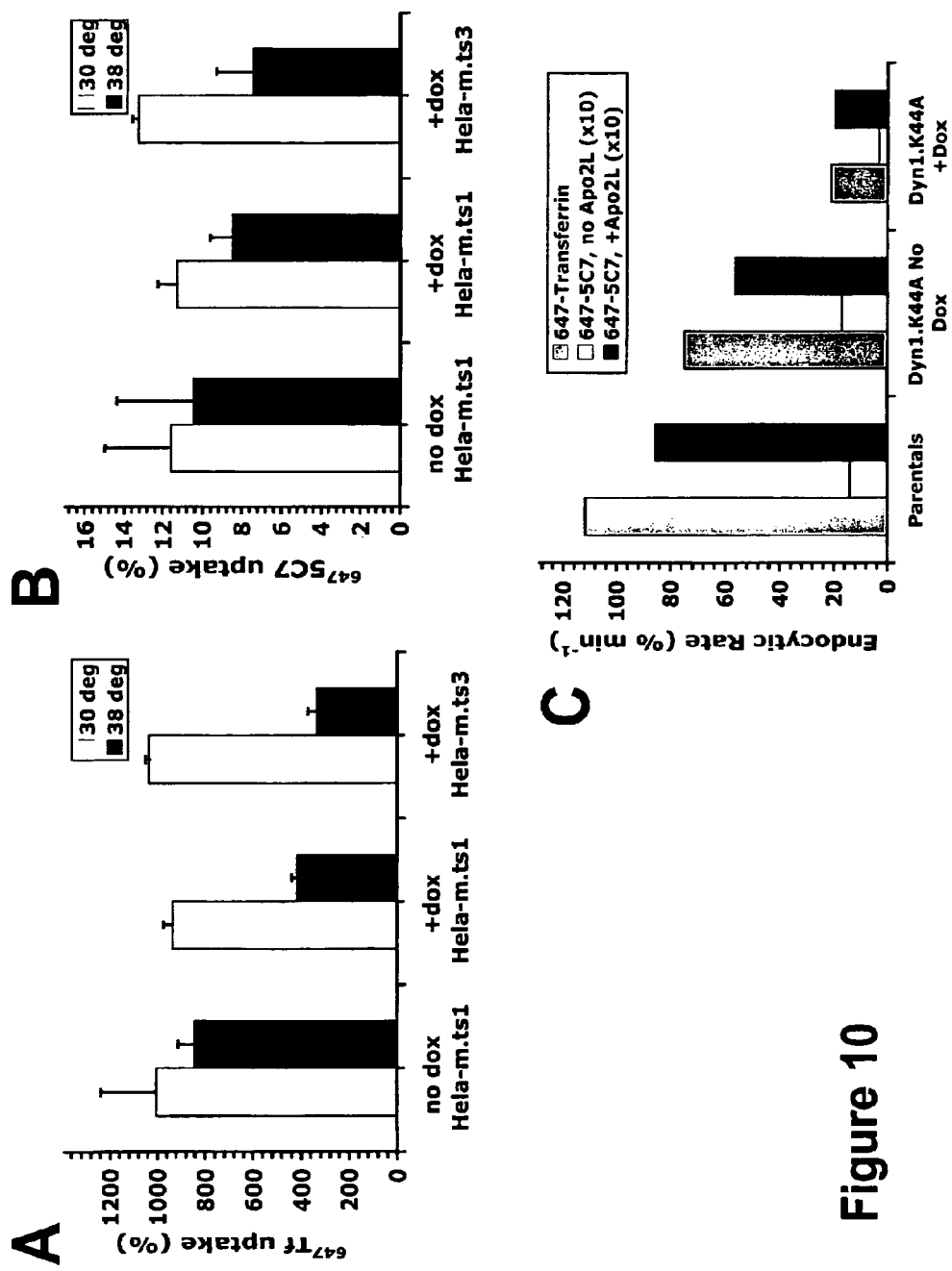
FIG. 10 Temperature sensitive Dyn1$^{G273D}$ and dominant-negative Dyn1$^{K44A}$ mutants inhibit endocytosis of Tf and DR5 in HeLa-M cells. (a, b) Two clonal lines derived from the retrovirally transduced HeLa-M cell population in FIG. 6, ts3 and ts1, with (+dox) or without (no dox) doxycycline induction were assayed for $^{488}$Tf (A) or $^{647}$5C7 (b) uptake over a 20 min period at 30° C. (white bars) or 38° C. (black bars) by flow cytometry as described in Experimental Procedures and means plotted (±SD). (c) Dyn$^{K44A}$-transduced and nontransduced (parental) HeLa-M cells with or without doxycyline induction were assayed for $^{488}$Tf and $^{647}$5C7 endocytosis rates (±SD) as described in FIG. 5d without normalization.

Next, an established intervention strategy was used that was based on doxycycline-regulated expression of a temperature-sensitive mutant of the GTPase dynamin-1 (dyn$^{G273D}$) in retrovirus-infected cells. This mutant rapidly and reversibly inhibits clathrin-dependent endocytosis upon shifting from a permissive (30° C.) to a nonpermissive (38° C.) temperature (see, e.g., Damke, H., et al., *J Cell Biol* 131, 69-80 (1995)). Initial experiments in HeLa-M cells confirmed that doxycyline induction blocked Tf uptake at 38° C. in cells with dyn$^{G273D}$ expression but not in neighboring, non-expressing cells, nor at 30° C. (FIG. 5a-d, and FIG. 10a). While inducible expression of dyn$^{G273D}$ in HeLa-M or Colo205 cells was not sufficiently stable, it was stable in a transduced BJAB cell line, with a strong block in Tf uptake at 38° C. (FIG. 5e). Doxycyclin-stimulated expression of dyn$^{G273D}$ also decreased ligand-induced DR5 uptake from ~25% at 30° C. to ~10% at 38° C. By contrast, endocytosis was similar at both temperatures in absence of doxycylin (FIG. 5f). In HeLa-M cells dyn$^{G273D}$ induction followed by a shift to 38° C. also attenuated ligand-induced DR5 uptake; this effect was weaker than in BJAB cells, probably because of diminished dyn$^{G273D}$ expression (FIG. 10b). To exclude the unlikely possibility that decreased DR5 uptake in these 20 min uptake experiments was attributed to increased endocytic recycling rather than reduced endocytosis rates best measured over a 4 min uptake interval, a dominant-negative dynamin mutant (dynamin-1$^{K44A}$) that unconditionally blocks clathrin-dependent endocytosis was used (see, e.g., Damke, H., et al., *J Cell Biol* 127, 915-34 (1994)). Dynamin-1$^{K44A}$ inhibited both Tf and ligand-induced DR5 endocytosis in HeLa-M cells (FIG. 10c).

Figure 11:
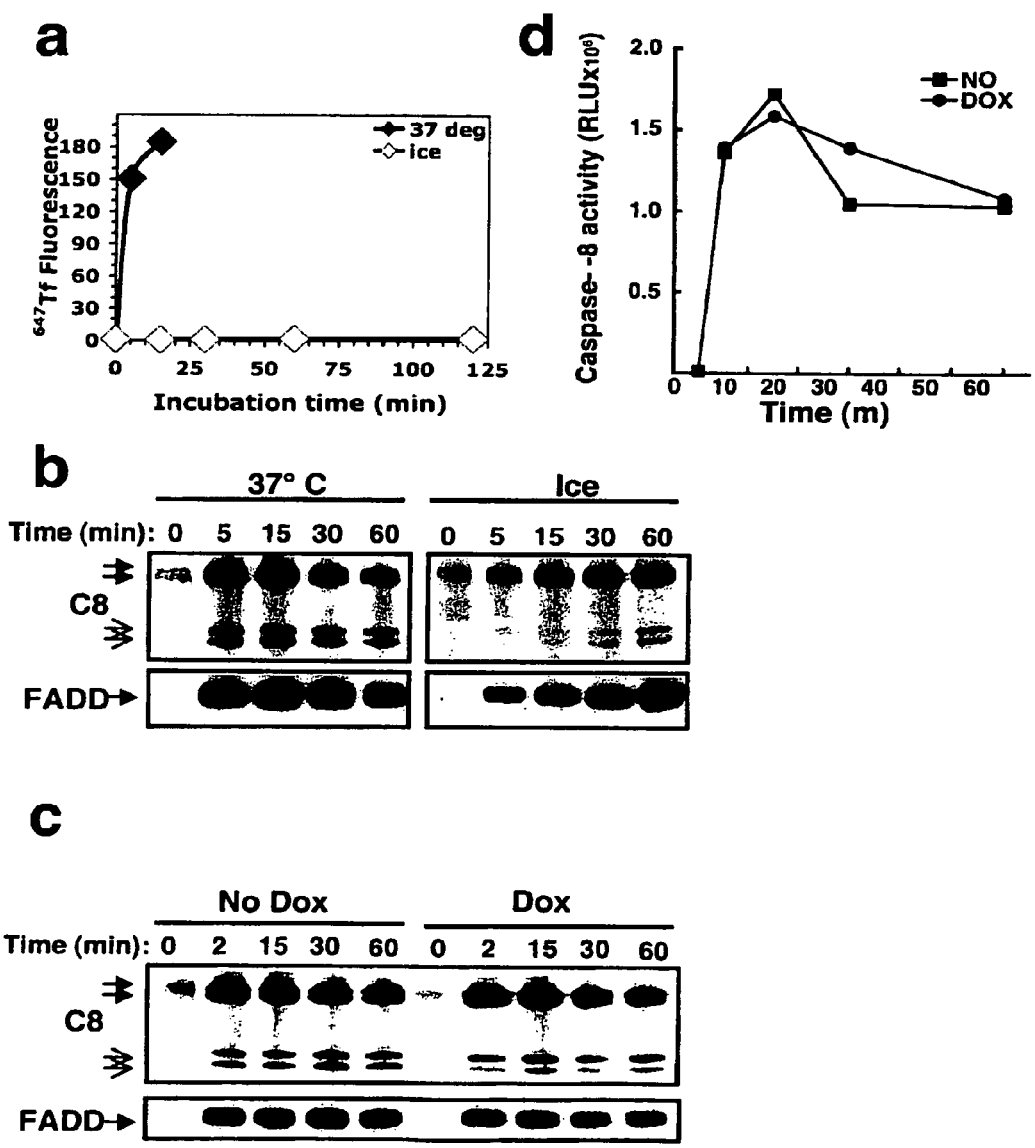
FIG. 11 shows DISC assembly in the absence of endocytosis. (a) BJAB cells were equilibrated with $^{647}$Tf on ice, incubated for the indicated uptake interval at 37° C. or on ice, then fluorescence quantified by flow cytometry. (b) BJAB cells were treated with crosslinked Apo2L/TRAIL (1 μg/mL) at 37° C. or on ice for the indicated amounts of time and the DISC was immunoprecipitated through the ligand as described in Materials and Methods. DISC-associated FADD and caspase-8 were visualized by immunoblot. (c, d) Dyn$^{G273D}$-transduced BJAB cells were treated with buffer (No Dox) or doxycyline (Dox) and shifted to 38° C. for 20 min to inactivate dynamin. The cells were treated with crosslinked Apo2L/TRAIL for the indicated amounts of time and the DISC was immunoprecipitated. DISC-associated FADD and caspase-8 were visualized by immunoblot (c) or DISC-associated caspase-8 activity was measured as described previously (Sharp et al. *J Biol Chem* 280, 19401-409, 2005).

Together with the EM data, these results indicate that Apo2L/TRAIL-induced DR5 uptake occurs primarily through clathrin-dependent endocytosis. Thus, physical proximity of the DISC within coated pits to clathrin-coat components may facilitate their cleavage. If true, DISC assembly and initiator-caspase activation should not require actual internalization of the coated pits. To test this, BJAB cells were chilled on ice to block Tf endocytosis (FIG. 11a). Despite the block, Apo2L/TRAIL and FasL still recruited FADD and caspase-8 to their respective receptors and processed caspase-8 (FIG. 11b). Furthermore, Apo2L/TRAIL induced comparable DISC formation, caspase-8 processing, and caspase-8 activity in the DISC at 38° C. despite endocytosis inhibition by dyn$^{G273D}$ (FIGS. 11c and d).

Figure 6:
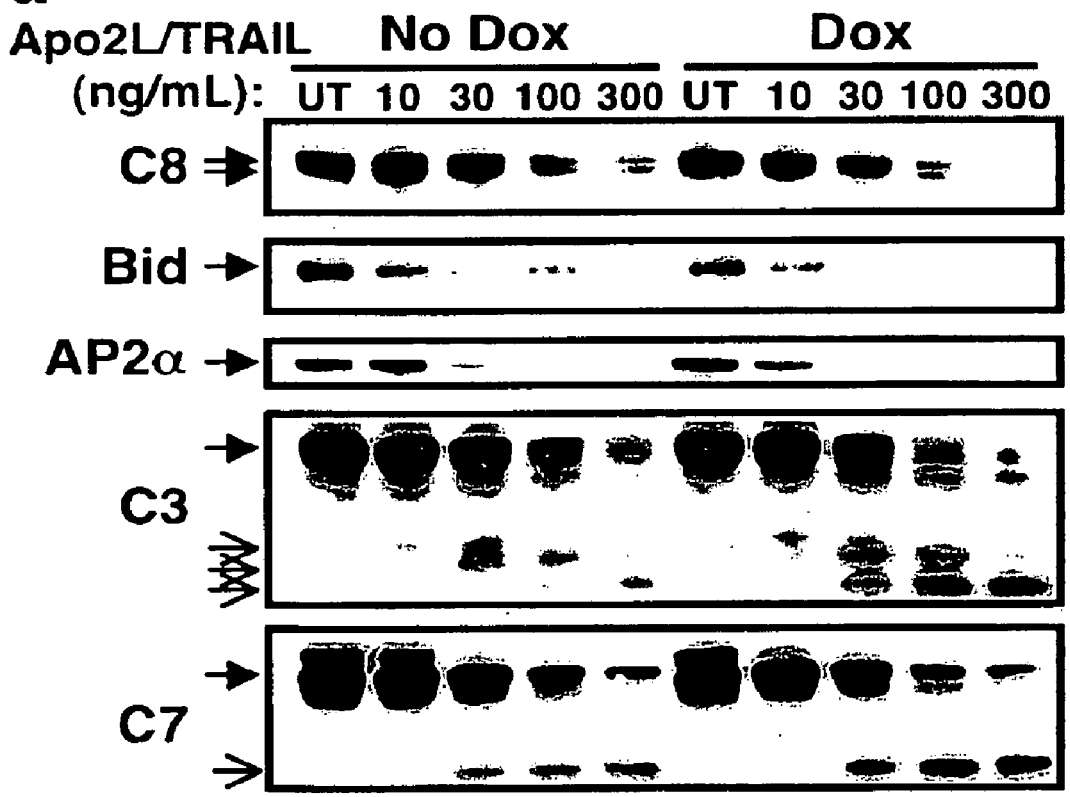
FIG. 6 shows that Dynamin inactivation augments DR-mediated caspase activation and apoptosis. (a) Dyn$^{G273D}$-transduced BJAB cells with or without doxycyline induction were incubated at 38° C. for 20 min to inactivate dynamin as in FIG. 5, then incubated an additional 4 hr with or without crosslinked Apo2L/TRAIL and analyzed by immunoblot for processing of the indicated proteins. (b) Dyn$^{G273D}$-transduced BJAB cells with or without doxycyline induction were incubated at 30° C. or 38° C. for 20 min, then incubated an additional 2 hr with or without crosslinked Apo2L/TRAIL and assayed for caspase-3/7 activity. (c) Dyn$^{G273D}$-transduced BJAB cells with or without doxycyline induction were pre-incubated at 38° C. for 20 min, then incubated an additional 4 hr with or without crosslinked Apo2L/TRAIL or a DR5-selective Apo2L/TRAIL mutant (D5-sel.) and DNA fragmentation assayed (±SEM).
Figure 6:
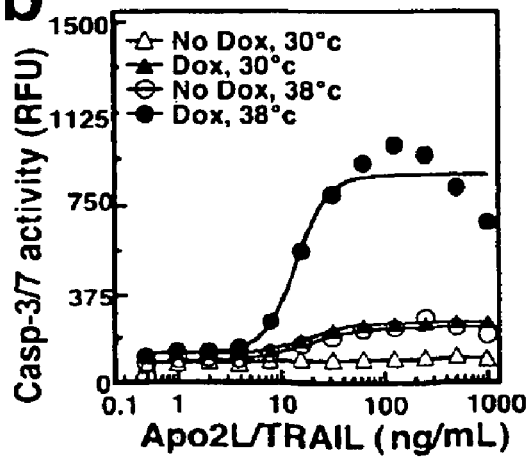
Figure 6:
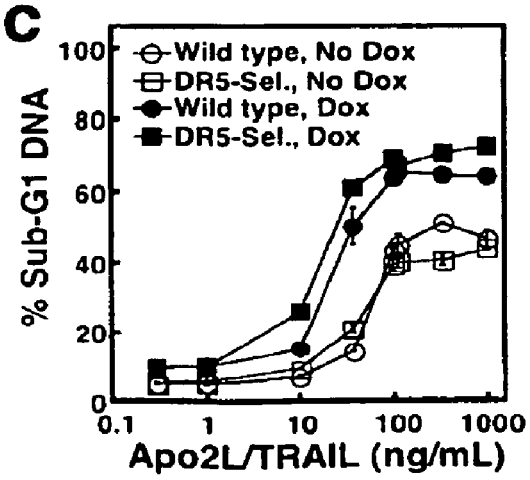

Inhibition of Clathrin-Mediated Endocytosis Augments DR-Induced Caspase Activation and Apoptosis The rapid cleavage of clathrin-pathway proteins provides evidence that disruption of endocytosis might promote ligand-induced caspase activation and apoptosis. Indeed, $dyn^{G273D}$-mediated blockade of endocytosis markedly augmented ligand-induced processing of the total cellular caspase-8 pool, Bid, AP2α and effector caspases-3 and -7 from whole-cell lysates (FIG. 6a), without significantly altering formation or activation of the DISC itself (FIGS. 11c and d). Quantitative analysis showed a substantial increase in ligand-stimulated caspase-3/7 enzymatic activity after induction of $dyn^{G273D}$ and temperature-shift to 38° C. as compared to 30° C. (FIG. 6b). Moreover, this condition also resulted in augmented apoptosis (FIG. 6c), an effect observed after stimulation with either the wt ligand or a DR5-selective variant (see, e.g., Kelley, R. F. et al., *J Biol Chem* 280, 2205-12 (2005)). Sensitization was evident not only by a left-shift of the dosage-response curve, but also by greater maximal percentage of cells with fragmented DNA (FIG. 6c). These results indicate that caspase-mediated disruption of clathrin-dependent endocytosis amplifies caspase activation downstream of the DISC, leading to stronger apoptosis stimulation.

As described above, using methods and materials of the invention, an unexpected interaction between the cell-extrinsic apoptosis pathway and the clathrin-dependent endocytosis machinery was uncovered. Within minutes of pro-apoptotic DR engagement, activated caspases begin to cleave proteins that mediate clathrin-dependent endocytosis. The relatively rapid kinetics of AP2α cleavage, the requirement of this event for FADD and caspase-8, and the independence from Bax and caspase-3 provide evidence that DR-proximal caspases, most likely caspase-8 and/or caspase-10, carry out the initial processing of AP2α. Indeed, the caspase cleavage site in the AP2α hinge fits with sequences that caspase-8 is capable of recognizing (see, e.g., Nicholson, D. W., *Cell Death Differ* 6, 1028-42 (1999)).

The inhibition of clathrin-dependent endocytosis by DR activation occurred in the same timeframe as caspase stimulation and was reversed by zVAD-fmk, demonstrating its dependence on caspase activity. The primary AP2α processing site mapped to the hinge region. The hinge links the ear domain, which supports accessory protein recruitment, to the trunk domain, which mediates PM association and cargo binding in conjunction with other AP2 subunits (see, e.g., Owen, D. J., et. al, P. R. *Annu Rev Cell Dev Biol* 20, 153- (2004)). Overexpression of the AP2α ear domain in COST cells inhibits clathrin-dependent endocytosis, an effect abrogated by mutations that prevent accessory-protein binding (see, e.g., Owen, D. J. et al., *Cell* 97, 805-15 (1999)). Conversely, studies in Drosophila in which some cells express only earless AP2α provide evidence that the ear domain is not required in general endocytosis (see, e.g., Berdnik, D., et al., *Dev Cell* 3, 221-31 (2002)). Thus, it is unclear whether caspase cleavage of AP2α alone is sufficient to perturb endocytosis, or whether the processing of other clathrin-pathway components also contributes. Regardless, DR-mediated caspase activation rapidly disrupts clathrin-dependent endocytosis.

In considering how activated caspases access clathrin-coat substrates, the data provides evidence that after Apo2L/TRAIL stimulation, a substantial portion of surface DR5 moves into the cell through clathrin-dependent endocytosis. Preliminary EM studies confirm that DR5 associates with clathrin-coated pits. Recent work indicates that RNAi-mediated knockdown of clathrin and AP2 inhibits apoptotic signaling through Fas, a result interpreted as revealing an endocytosis requirement for receptor signaling (see, e.g., Lee, K. H. et al., *Embo J* 25, 1009-23 (2006)). In light of observations that Apo2L/TRAIL DISC assembly, activation, and apoptosis can still occur when endocytosis is inhibited by incubation on ice or through dynamin inactivation, it is surmised that DR5 can bind FADD and caspase-8 while still at the cell surface, possibly within clathrin-coated pita. Indeed, blocking endocytosis with incubation on ice or temperature-sensitive dynamin does not interfere with coated-pit formation and cargo recruitment (see, e.g., Damke, H., et al., *J Cell Biol* 131, 69-80 (1995)). DR activation caused nearly complete destruction of AP2α. In contrast, CHC and AP1/2β processing involved only a fraction of the total cellular proteins, perhaps the fraction that participated directly in DR endocytosis. Thus, caspase activation in the vicinity of the internalizing DR-associated DISC may lead to local destruction of specific clathrin-pathway components.

Figure 12:
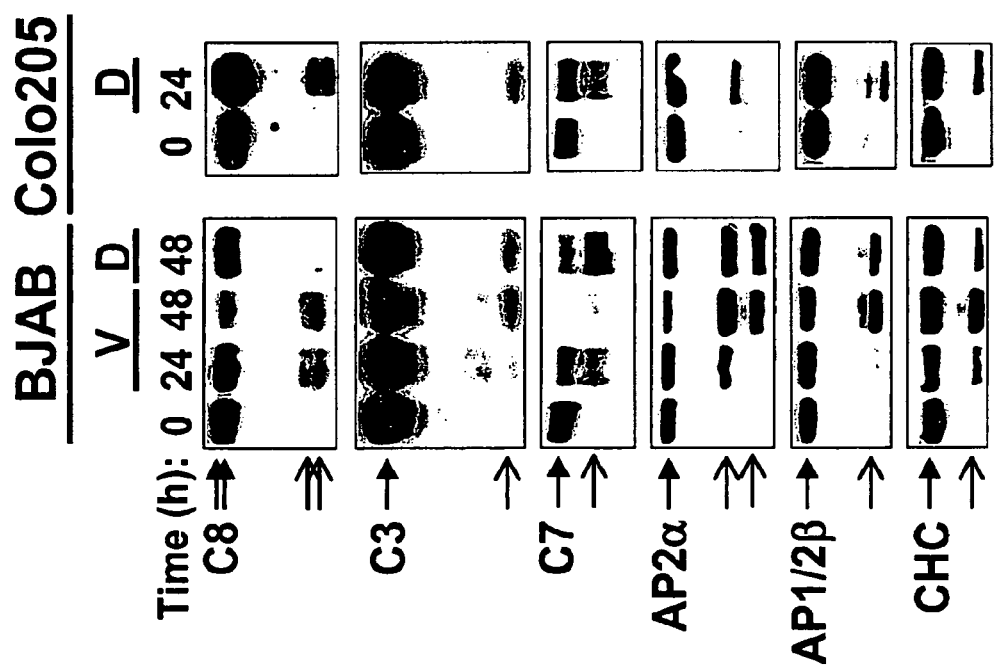
FIG. 12 shows that DNA-damaging agents induce cleavage of clathrin-pathway components. BJAB or Colo205 cells were treated with vinblastine, or adriamycin for the indicated time and analyzed by immunoblot as in FIG. 1.

One straightforward implication of the finding that caspases disrupt clathrin-mediated endocytosis is that the elimination of this mechanism may represent a previously unrecognized part of the apoptotic program; a cell that is committed to apoptosis no longer needs to take up nutrients, respond to growth factors, or maintain membrane homeostasis. It is unlikely however, that these cleavages on their own trigger apoptosis, as both clathrin and AP2 have been efficiently knocked down using siRNAs by a number of different labs, with none reporting an increase in apoptosis. Notably, the cytotoxic, DNA-damaging drugs vinblastine and adriamycin also induced cleavage of components of the clathrin machinery, albeit with much slower kinetics than DR ligands (FIG. 12). On the other hand, caspase-mediated processing of clathrin adaptors may play a role also in non-apoptotic cell modulation: In immature dendritic cells, basal caspase activity leads to cleavage of several adaptin subunits, while zVAD-inhibition of this effect promotes dendritic cell maturation (see, e.g., Santambrogio, L. et al., *Nat Immunol* 6, 1020-8 (2005)).

A second, perhaps more surprising, implication of the interplay between DRs and the clathrin endocytic machinery is that this interaction provides a positive feedback-loop that reinforces caspase activation through the extrinsic pathway. According to this model, endocytosis of activated DRs opposes apoptotic signaling to preserve cell survival if the clathrin machinery remains intact, for instance in response to sub-threshold ligand levels. However, if DR stimulation generates enough caspase activity to disrupt endocytosis, then the signal persists, amplifying further caspase activation and promoting apoptosis. Conceivably, DR endocytosis could oppose DR signaling through lysosomal degradation, some other form of signal termination, or induction of competing anti-apoptotic signals. Endocytosis did not regulate caspase activation at the level of initial DISC association. Nonetheless, dynamin inactivation enhanced the processing of total cellular caspase-8, and progressively, of caspase-3 and -7, and led to stronger apoptosis activation, providing evidence that endocytosis regulates further caspase activation downstream of the initial DISC.

In summary, a bidirectional relationship between DR-induced apoptosis and clathrin-dependent endocytosis is disclosed herein: DR activation leads to caspase-mediated destruction of important components of the clathrin endocytic machinery, thereby halting this process. Disruption of clathrin-dependent endocytosis augments caspase activation downstream of DRs and increases apoptosis, providing evidence of a positive feedback-loop that amplifies caspase activation and apoptosis execution.

The following examples are offered by way of illustration and not by way of limitation. The disclosures of all citations in the specification are expressly incorporated herein by reference.

EXAMPLES

Example 1

Illustrative Materials and Methods

Identification of the AP2α Caspase Cleavage Site

BJAB cells ($5 \times 10^8$) were stimulated with Apo2L/TRAIL for 30 min and then lysed, immunoprecipitated using C-terminal specific anti-AP2α (AP6, #MA1-064 from ABR) and collected on protein A/G agarose (Pierce). The C-terminal fragment was resolved by SDS-PAGE and either eluted for tryptic cleavage and analysis by liquid-chromatography-electrospray ionization-ion trap tandem mass spectrometry or, in a separate IP, transferred to a PVD membrane for N-terminal sequencing.

Endocytosis, Uptake, and Surface Downregulation Assays

For routine Tf measurements, $10^6$ suspended cells were pretreated for indicated times at 37° C. with 1-10 µg/ml Apo2L/TRAIL. In some studies, cells were pretreated with 0.25% DMSO+/−50 mM zVADfmk for 30 min at 37° C. before adding Apo2L/TRAIL. After Apo2L/TRAIL stimulation, cells were equilibrated 30 min on ice with 5 µg/ml fluorescent Tf in binding medium (serum-free DME, 3% BSA, 20 mM Hepes, pH 7.2), shifted to 37° C. for 0-5 min as indicated, then rapidly chilled on ice to halt endocytosis. Sedimented cells were resuspended in cold 2% paraformaldehyde/PBS and mean fluorescence intensity of 10,000 cells quantified with a Coulter Epics Elite-ESP flow cytometer (Hialeah, Fla.). Endocytic rates were determined from linear slopes of steady-state internal/surface plots (see, e.g., Wiley, H. S. et. al, *J Biol Chem* 257, 4222-9 (1982)). For temperature-shift experiments, ice binding incubations were avoided. Instead, cells were preconditioned for 20 min and maintained at 30° C. or 38° C. in binding medium, incubated an additional 0 (control) or 20 min with $^{647}$Tf, chilled on ice for 30 min, and processed for flow cytometry to determine internal/surface $^{647}$Tf ratios.

For routine DR5 measurements, cells were saturated on ice with 5 µg/ml $^{647}$5C7 in binding medium, washed 3 times with cold binding medium, then incubated 30 min on ice with or without 10 µg/ml Apo2L/TRAIL. Cells were then shifted to 37° C. for the indicated time, rapidly chilled, and either acid stripped or not three times with cold 2M urea, 50 mM glycine, 150 mM NaCl, pH 2.4. Cells were processed for flow cytometry and internalization calculated similarly to the method described previously with the equation: % uptake=$100 \times [(S_t - S_0)/(N - S_0)]$, where $S_t$ and $S_0$ are the values of acid stripped samples incubated for time=t and time=0, respectively, and N is nonstripped fluorescence, which remained essentially unchanged during the course of the 37° C. incubation (see, e.g., Austin, C. D. et al., *Mol Biol Cell* 15, 5268-82 (2004)).

For temperature shift, cells were preconditioned for 20 min and maintained at 30° C. or 38° C., pre-equilibrated with 5 µg/ml $^{647}$5C7 for 3 min, treated with 10 µg/ml Apo2L/TRAIL for 0 (control) or 20 min, then chilled on ice 30 min. Cells were acid stripped or not and quantified by flow cytometry.

For surface DR5 down-modulation assays, suspended cells were pre-equilibrated at 37° C. with unlabeled 5C7 for 30 min to bind surface and recycling DR5 pools, treated for the indicated time with or without 10 ug/ml Apo2L/TRAIL, and chilled on ice. Surface 5C7 was probed with CY5-anti-mouse IgG and quantified by flow cytometry. This technique was employed to avoid reduced surface probing efficiency attributable to Apo2L/TRAIL-induced receptor clustering, as seen upon direct probing with $^{647}$5C7.

Caspase Activity Assays

The caspase-3/7 assay was performed using Apo-One Homogenous Caspase-3/7 Assay (Promega). Cells were harvested, counted, aliquoted at equal numbers for each treatment and treated with Apo2L/TRAIL at varying doses for 4 hours at 30° C. or 38° C. and then lysed in Homogeneous Caspase-3/7 Reagent (containing the caspase-3/7 substrate Z-DEVD-R110). Lysates were incubated at room temperature for 1 hour before reading in a fluorometer at 485/530 nM.

Apoptosis Assays

Cells were stained with propidium iodide after ethanol fixation and RNase treatment and the amount of sub-diploid DNA was analyzed by flow cytometry as previously described, using Expo32 software with an Epics XL.MCL cytometer (Coulter Beckman), (see, e.g., Nicholson, D. W., *Cell Death Differ* 6, 1028-42 (1999)).

DISC Immunoprecipitation

BJAB cells ($1 \times 10^7$ per time point) were treated with Flag-Apo2L/TRAIL cross-linked by anti-FLAG M2 Abs, collected, lysed, immunoprecipitated and the DISC was analyzed as described (see, e.g., Kischkel, F. C. et al., *Immunity* 12, 611-20 (2000)).

Cell Lines and Reagents

Human colorectal adenocarcinoma Colo205 cells human B cell lymphoma BJAB cells and human T cell carcinoma Jurkat wild type cells (A3 clone), FADD-deficient (E1) and caspase-8-deficient (I9.3) were cultured in RPMI 1640+10% fetal bovine serum (FBS)+2 mM glutamine+1000 U/ml Penicillin-Streptomycin (Life Technologies). Human cervical carcinoma HeLa-M cells human breast adenocarcinoma MCF7 and human colorectal adenocarcinomas HCT15, HCT8, SW948, Colo320, human fibrosarcoma HT180 (ATCC), HCT116 Bax(−/−), HCT116 Bax(+/−) were grown in 50:50 Dulbecco's modified Eagle's and FK12 medium+10% FBS+1000 U/ml Penicillin-Streptomycin. cDNA clones encoding temperature-sensitive dynamins were the G273D mutant and dominant negative K44A mutant dynamin-1 ($\text{Dyn}^{G273D}$ and $\text{Dyn}^{K44A}$, respectively). $\text{Dyn}^{G273D}$ was expressed from pHUSH-ProEx, a single retroviral plasmid tetracycline-inducible expression system constructed at Genentech. The cDNA was first cloned into a shuttle plasmid containing a CMV enhancer-promoter sequence with two copies of the tetracycline operator TetO$_2$, then transferred via in vitro phage lamda-based recombination, or Gateway® technology (Invitrogen, Carlsbad), to a Moloney murine leukemia virus backbone vector in which the wild type Tet repressor is driven by a separate β-actin promoter and followed by an internal ribosomal entry sequence and puromycin selection cassette. $\text{Dyn}^{K44A}$ was expressed from the 2-vector tetracycline-inducible retroviral expression system, pRevTet-On/pRev-Tre (Clontech), using serial infections. Retroviral vectors were transfected into Phoenix amphotropic Moloney Murine Leukemia Virus packaging cells using Lipofectamine 2000 (Stratagene). Retroviral particles were harvested and used in HeLa-M and BJAB cell infections as described previously (Simpson et al. *J Cell Biol* 137, 835-45, 1997). $\text{Dyn}^{G273}$ infected cells were puromycin selected (2-3 µg/ml) for 1-2 weeks and cloned either by manually picking individual HeLa-M colonies or by FACS sorting of resistant BJAB cells (gated for exclusion of propidium iodide) and single cell seeding in 96-well cell culture plates using an EPICS ELITE-ESP equipped with an Autoclone device (Coulter, Hialeah, Fla.). Cell clones were screened for uniformity of doxycycline inducible dynamin-1 expression by immunofluorescence microscopy. Dyn$^{K44A}$-infected cells were hygromycin B (400 µg/ml) and G418 (1 mg/ml) selected for 1-2 weeks. Induction with doxycycline (1 µg/ml) was performed at 32° C. for 72 hr as described previously (Damke et al. *J Cell Biol* 131, 69-80 1995). Vincristine sulfate (#T-117), Adriamycin.HCL (GR-319) were purchased from Biomol, tetracycline-free FBS from Hyclone, Puromycin from Clontech and Doxycyclin from Sigma. zVAD-fmk (asN-benzyloxycarbonyl-Val-Ala-Asp-fluoromethylketone) was obtained from MD Biosciences (#FK-009).

Recombinant Proteins, Antibodies, and Fluorescent Markers

Human recombinant soluble Apo2L/TRAIL in non-tagged or Flag-tagged versions and Flag-tagged FasL were prepared as described (Sharp et al. *J Biol Chem* 280, 19401-409, 2005). For immunoblot analysis the following antibodies were used: anti-Caspase-8 (1C12, #9746) and anti-Caspase-7 (C7, #9494) from Cell Signaling, anti-Caspase-8 (5F7, #IM3148) from Immunotech, anti-FADD (#610399), anti-AP2α (#610501), anti-AP1/2α 610381) anti-AP1γ (#610385), anti-AP3δ (#611328), anti-CHC (#610499), anti-AP4ε (#612018), anti-Bid (#550365) and anti-dynamin 1/2 (#610245) from BD Transduction, anti-Caspase 3 (SA-320) from Biomol, anti-Caspase 9 (Ab2, #AM47) from Oncogene, anti-Tf receptor (#13-6800) from Zymed, anti-βCop (M3A5, #G2279) from Sigma, anti-Sec23 (#GTX22913) from Gentex, anti-DR5 (3H3 and 5C7) monoclonal antibodies were generated at Genentech, Inc., and anti-AP3β as described previously (see, e.g. Simpson et al., J. Cell Biol. Volume 137, No. 4 pp 835-845 (1997)). As the secondary reagents the following horseradish peroxidase (HRP)-conjugated Abs were used: anti-mouse-IgG1 (#559626) from BD Bioscience; and anti-mouse-IgG2b (#190-05) from Southern Biotechnology Associates, anti-rabbit-IgG (#711-035-152) from Jackson ImmunoResearch. For immunoprecipitation experiments the following Abs were used: anti-Flag (M2, Sigma) and anti-AP2α (AC1-M11, #MA3-061) or (AP6, #MA1-064) from ABR. For flow cytometry and immunofluorescence microscopy, [488]Tf (T-13342), [647]TF (T-23366), [594]anti-rabbit IgG (#A-11037), and [594]anti-goat IgG (#A-11058) from Molecular Probes. Fragment anti-mouse IgG (#115-177-003) from Jackson ImmunoResearch, anti-dynamin-1 (#sc-6402) from Santa Cruz Biotechnology and anti-Alexa 647 rabbit polyclonal antibody generated at Genentech, Inc. using Alexa 647-conjugated bovine serum albumin (Molecular Probes, Inc.) as an antigen and affinity purified on an Alexa-647 sepharose column created by reacting (CNBr)-activated sepharose with Alexa Fluor 647 cadaverin (Molecular Probes, Inc.). Alexa-647 was conjugated to mAb 5C7 ([647]5C7) by reaction with Alexa-647 succinimidyl ester (Molecular Probes, Inc.) as per manufacturer's instructions.

Immunofluorescence Microscopy

Cells for [647]5C7 uptake imaging were incubated at 37° C. with [647]5C7 and crosslinked Apo2L/TRAIL for the indicated time. Cells for temperature sensitive experiments were pretreated in binding medium 20 min. at 30° C. vs 38° C., then [488]Tf added and incubations continued at the respective temperatures for the indicated time. Cells were then fixed for 20 min with 3% paraformaldehyde, permeabilized with 0.4% saponin, and stained with rabbit anti-Alexa 647 IgG followed by [594]anti-rabbit IgG ([647]5C7 uptake) or with anti-dynamin-1 antibody followed by [594]anti-goat IgG (temperature sensitive experiments). Images were acquired using a microscope (Axiovert 200; Carl Zeiss MicroImaging, Inc.) fitted with a Plan-Apochromat 1.4 NA 63× objective, a CCD camera (Axio-Cam; Carl Zeiss MicroImaging, Inc.), and a Quad pass filter set (Chroma Technology Corp.), all controlled by AxioVison 3.1 software (Carl Zeiss MicroImaging, Inc.).

Immunoelectron Microscopy

Suspended Colo205 cells were incubated 30 min on ice with 10 µg/ml 5C7 in binding medium, washed, incubated on ice 30 min with 10 mg/ml Apo2L/TRAIL in binding medium, then shifted to 37° C. for 5 min, fixed in 2% paraformaldehyde/0.2% glutaraldehyde, and processed as described previously (Austin et al. Mol Biol Cell 15, 5268-82, 2004) for immunogold labeling of ultrathin cryosections with rabbit anti-mouse IgG (Dako, Glostrup, Denmark).

The foregoing written description is considered to be sufficient to enable one skilled in the art to practice the invention. The present invention is not to be limited in scope by the example presented herein. Indeed, various modifications of the invention in addition to those shown and described herein will become apparent to those skilled in the art from the foregoing description and fall within the scope of the appended claims.

TABLES

TABLE 1

EXEMPLARY POLYPEPTIDES USEFUL IN THE PRACTICE
OF THE INVENTION

AP2-α (SEQ ID NO: 1)
NCBI ACCESSION NO.: CAB66859
MPAVSKGDGMRGLAVFISDIRNCKSKEAEIKRINKELANIRSKFKGDK
ALDGYSKKKYVCKLLFIFLLGHDIDFGHMEAVNLLSSNKYTEKQIGYL
FISVLVNSNSELIRLINNAIKNDLASRNPTFMCLALHCIANVGSREMG
EAFAADIPRILVAGDSMDSVKQSAALCLLRLYKASPDLVPMGEWTARV
VHLLNDQHMGVVTAAVSLITCLCKKNPDDFKTCVSLAVSRLSRIVSSA
STDLQDYTYYFVPAPWLSVKLLRLLQCYPPPEDAAVKGRLVECLETVL
NKAQEPPKSKKVQHSNAKNAILFETISLIIHYDSEPNLLVRACNQLGQ
FLQHRETNLRYLALESMCTLASSEFSHEAVKTHIDTVINALKTERDVS
VRQRAADLLYAMCDRSNAKQIVSEMLRYLETADYAIREEIVLKVAILA
EKYAVDYSWYVDTILNLIRIAGDYVSEEVWYRVLQIVTNRDDVQGYAA
KTVFEALQAPACHENMVKVGGYILGEFGNLIAGDPRSSPPVQFSLLHS
KFHLCSVATRALLLSTYIKFINLFPETKATIQGVLRAGSQLRNDWHL
QQRAVEYLTLSSVASTDVLATVLEEMPPFPERESSILAKLKRKKGPGA
GSALDDGRRDPSSNDINGGMEPTPSTVSTPSPSADLLGLRAAPPPAAP
PASAGAGNLLVDVFDGPAAQPSLGPTPEEAFLSPGPEDIGPPIPEADE
LLNKFVCKNNGVLFENQLLQIGVKSEFRQNLGRMYLFYGNKTSVQFQN
FSPTVVHPGDLQTQLAVQTKRVAAQVDGGAQVQQVLNIECLRDFLTPP
LLSVRFRYGGAPQALTLKLPVTINKFFQPTEMAAQDFFQRWKQLSLPQ
QEAQKIFKANHPMDAEVTKAKLLGFGSALLDNVDPNPENFVGAGIIQT
KALQVGCLLRLEPNAQAQMYRLTLRTSKEPVSRHLCELLAQQF

CLATHRIN HEAVY CHAIN (SEQ ID NO: 2)
NCBI ACCESSION NO.: NP 004850
MAQILPIRFQEHLQLQNLGINPANIGFSTLTMESDKFICIREKVGEQA
QVVIIDMNDPSNPIRRPISADSAIMNPASKVIALKAGKTLQIFNIEMK
SKMKAHTMTDDVTFWKWISLNTVALVTDNAVYHWSMEGESQPVKMFDR
HSSLAGCQIINYRTDAKQKWLLLTGISAQQNRVVGAMQLYSVDRKVSQ
PIEGHAASFAQFKMEGNAEESTLFCFAVRGQAGGKLHIIEVGTPPTGN
QPFPKKAVDVFFPPEAQNDFPVAMQISEKEDVVFLITKYGYIHLYDLE
TGTCIYMNRISGETIFVTAPHEATAGIIGVNRKGQVLSVCVEEENIIP
YITNVLQNPDLALRMAVRNNLAGAEELFARKFNALFAQGNYSEAAKVA
ANAPKGILRTPDTIRRFQSVPAQPGQTSPLLQYFGILLDQGQLNKYES
LELCRPVIQQGRKQLLEKWLKEDKLECSEELGDLVKSVDPTLALSVYL
RANVPNKVIQCFAETGQVQKIVLYAKKVGYTPDWIFLLRNVMRISPDQ
GQQFAQMLVQDEEPLADITQIVDVFMEYNLIQQCTAFLLDALKNNRPS
EGPLQTRLLEMNLMHAPQVADAILGNQMFTHYDRAHIAQLCEKAGLLQ
RALEHFTDLYDIKRAVVHTHLLNPEWLVNYFGSLSVEDSLECLRAMLS
ANIRQNLQICVQVASKYHEQLSTQSLIELFESFKSFEGLFYFLGSIVN
FSQDPDVHFKYIQAACKTGQIKEVERICRESNCYDPERVKNFLKEAKL
TDQLPLIIVCDRFDFVHDLVLYLYRNNLQKYIEIYVQKVNPSRLPVVI
GGLLDVDCSEDVIKNLILVVRGQFSTDELVAEVEKRNRLKLLLPWLEA
RIHEGCEEPATHNALAKIYIDSNNNPERFLRENPYYDSRVVGKYCEKR
DPHLACVAYERGQCDLELINVCNENSLFKSLSRYLVRRKDPELWGSVL
LESNPYRRPLIDQVVQTALSETQDPEEVSVTVKAFMTADLPNELIELL
EKIVLDNSVFSEHRNLQNLLILTAIKADRTRVMEYINRLDNYDAPDIA
NIAISNELFEEAFAIFRKFDVNTSAVQVLIEHIGNLDRAYEFAERCNE

TABLE 1-continued
EXEMPLARY POLYPEPTIDES USEFUL IN THE PRACTICE OF THE INVENTION PAVWSQLAKAQLQKGMVKEAIDSYIKADDPSSYMEVVQAANTSGNWEE
LVKYLQMARKKARESYVETELIFALAKTNRLAELEEFINGPNNAHIQQ
VGDRCYDEKMYDAAKLLYNNVSNFGRLASTLVHLGEYQAAVDGARKAN
STRTWKEVCFACVDGKEFRLAQMCGLHIVVHADELEELINYYQDRGYF
EELITMLEAALGLERAHMGMFTELAILYSKFKPQKMREHLELFWSRVN
IPKVLRAAEQAHLWAELVFLYDKYEEYDNAIITMMNHPTDAWKEGQFK
DIITKVANVELYYRAIQFYLEFKPLLLNDLLMVLSPRLDHTRAVNYFS
KVKQLPLVKPYLRSVQNHNNKSVNESLNNLFITEEDYQALRTSIDAYD
NFDNISLAQRLEKHELIEFRRIAAYLFKGNNRWKQSVELCKKDSLYKD
AMQYASESKDTELAEELLQWFLQEEKRECFGACLFTCYDLLRPDVVLE
TAWRHNIMDFAMPYFIQVMKEYLTKVDKLDASESLRKEEEQATETQPI
VYGQPQLMLTAGPSVAVPPQAPFGYGYTAPPYGQPQPGFGYSM AP1/2β (SEQ ID NO: 3)
NCBI ACCESSION NO.: P63010
MTDSKYFTTNKKGEIFELKAELNNEKKEKRKEAVKKVIAAMTVGKDVS
SLFPDVVNCMQTDNLELKKLVYLYLMNYAKSQPDMAIMAVNSFVKDCE
DPNPLIRALAVRTMGCIRVDKITEYLCEPLRKCLKDEDPYVRKTAAVC
VAKLHDINAQMVEDQGFLDSLRDLIADSNPMVVANAVAALSEISESHP
NSNLLDLNPQNINKLLTALNECTEWGQIFILDCLSNYNPKDDREAQSI
CERVTPRLSHANSAVVLSAVKVLMKFLELLPKDSDYYNMLLKKLAPPL
VTLLSGEPEVQYVALRNINLIVQKRPEILKQEIKVFFVKNDPIYVKL
EKLDIMIRLASQANIAQVLAELKEYATEVDVDFVRKAVRAIGRCAIKV
EQSAERCVSTLLDLIQTKVNYVVQEAIVVIRDIFRKYPNKYESIIATL
CENLDSLDEPDARAAMIWIVGEYAERIDNADELLESFLEGFHDESTQV
QLTLLTAIVKLFLKKPSETQELVQQVLSLATQDSDNPDLRDRGYIYWR
LLSTDPVTAKEVVLSEKPLISEETDLIEPTLLDELICHIGSLASVYHK
PPNAFVEGSHGIHRKHLPIHHGSTDAGDSPVGTTTATNLEQPQVIPSQ
GDLLGDLLNLDLGPPVNVPQVSSMQMGAVDLLGGGLDSLVGQSFIPSS
VPATFAPSPTPAVVSSGLNDLFELSTGIGMAPGGYVAPKAVWLPAVKA
KGLEISGTFTHRQGHIYMEMNFTNKALQHMTDFAIQFNKNSFGVIPST
PLAIHTPLMPNQSIDVSLPLNTLGPVMKMEPLNNLQVAVKNNIDVFYF
SCLIPLNVLFVEDGKMERQVFLATWKDIPNENELQFQIKECHLNADTV
SSKLQNNNVYTIAERNVEGQDMLYQSLKLTNGIWILAELRIQPGNPNY
TLSLKCRAPEVSQYIYQVYDSILKN DYNAMIN (SEQ ID NO: 4)
NCBI ACCESSION NO.: NP 001005336
MGNRGMEDLIPLVNRLQDAFSAIGQNADLDLPQIAVVGGQSAGKSSVL
ENFVGRDFLPRGSGIVTRRPLVLQLVNATTEYAEFLHCKGKKFTDFEE
VRLEIEAETDRVTGTNKGISPVPINLRVYSPHVLNLTLVDLPGMTKVP
VGDQPPDIEFQIRDMLMQFVTKENCLILAVSPANSDLANSDALKVAKE
VDPQGQRTIGVITKLDLMDEGTDARDVLENKLLPLRRGYIGVVNRSQK
DIDGKKDITAALAAERKFFLSHPSYRHLADRMGTPYLQKVLNQQLTNH
IRDTLPGLRNKLQSQLLSIEKEVEEYKNFRPDDPARKTKALLQMVQQF
AVDFEKRIEGSGDQIDTYELSGGARINRIFHERFPFELVKMEFDEKEL
RREISYAIKNIHGIRTGLFTPDMAFETIVKKQVKKIREPCLKCVDMVI
SELISTVRQCTKKLQQYPRLREEMERIVTTHIREREGRTKEQVMLLID
IELAYMNTNHEDFIGFANAQQRSNQMNKKKTSGNQDEILVIRKGWLTI
NNIGIMKGGSKEYWFVLTAENLSWYKDDEEKEKKYMLSVDNLKLRDVE
KGFMSSKHIFALFNTEQRNVYKDYRQLELACETQEEVDSWKASFLRAG
VYPERVGDKEKASETEENGSDSFMHSMDPQLERQVETIRNLVDSYMAI
VNKTVRDLMPKTIMHLMINNTKEFIFSELLANLYSCGDQNTLMEESAE
QAQRRDEMLRMYHALKEALSIIGDINTTTVSTPMPPPVDDSWLQVQSV PAGRRSPTSSPTPQRRAPAVPPARPGSRGPAPGPPPAGSALGGAPPVP
SRPGASPDPFGPPPQVPSRPNRAPPGVPRITISDP DEATH RECEPTOR 4 (SEQ ID NO: 5)
NCBI ACCESSION NO.: 000220
MAPPPARVHLGAFLAVTPNPGSAASGTEAAAATPSKVWGSSAGRIEPR
GGGRGALPTSMGQHGPSARARAGRAPGPRPAREASPRLVHKTFKFVV
VGVLLQVVPSSAATIKLHDQSIGTQQWEHSPLGELCPPGSHRSEHPGA
CNRCTEGVGYTNASNNLFACLPCTACKSDEEERSPCTTTRNTACQCKP
GTFRNDNSAEMCRKCSRGCPRGMVKVGDCTPWSDIECVHKESGNGHNI
WVILVVTLVVPLLLVAVLIVCCCIGSGCGGDPKCMDRVCFWRLGLLRG
PGAEDNAHNEILSNADSLSTFVSEQQMESQEPADLTGVTVQSPGEAQC
LLGPAEAEGSQRRRLLVPANGADPTETLMLFFDKFANIVPFDSWDQLM
RQLDLTKNEIDVVRAGTAGPGDALYAMLMKWVNKTGRNASIHTLLDAL
ERMEERHAKEKIQDLLVDSGKFIYLEDGTGSAVSLE DEATH RECEPTOR 5 (SEQ ID NO: 6)
NCBI ACCESSION NO.: AAB67103
MEQRGQNAPAASGARKRHGPGPREARGARPGLRVPKTLVLVVAAVLLL
VSAESALITQQDLAPQQRAAPQQKRSSPSEGLCPPGHHISEDGRDCIS
CKYGQDYSTHWNDLLFCLACTRCDSGEVELSPCTTTRNTVCQCEEGTF
REEDSPEMCRKCRTGCPRGMVKVGDCTPWSDIECVHKESGIIIGVTVA
AVVLIVAVFVCKSLLWKKVLPYLKGICSGGGGDPERVDRSSQRPGAED
NVLNEIVSILQPTQVPEQEMEVQEPAEPTGVNMLSPGESEHLLEPAEA
ERSQRRRLLVPANEGDPTETLRQCFDDFADLVPFDSWEPLMRKLGLMD
NEIKVAKAEAAGHRDTLYTMLIKWVNKTGRDASVHTLLDALETLGERL
AKQKIEDHLLSSGKFMYLEGNADSALS APO2L/TRAIL (SEQ ID NO: 7)
NCBI ACCESSION NO.: NP 003801
MAMMEVQGGPSLGQTCVLIVIFTVLLQSLCVAVTYVYFTNELKQMQDK
YSKSGIACFLKEDDSYWDPNDEESMNSPCWQVKWQLRQLVRKMILRTS
EETISTVQEKQQNISPLVRERGPQRVAAHITGTRGRSNTLSSPNSKNE
KALGRKINSWESSRSGHSFLSNLHLRNGELVIHEKGFYYIYSQTYFRF
QEEIKENTKNDKQMVQYIYKYTSYPDPILLMKSARNSCWSKDAEYGLY
SIYQGGIFELKENDRIFVSVTNEHLIDMDHEASFFGAFLVG FAS (SEQ ID NO: 8)
NCBI ACCESSION NO.: AAA63174
MLGIWTLLPLVLTSVARLSSKSVNAQVTDINSKGLELRKTVTTVETQN
LEGLHHDGQFCHKPCPPGERKARDCTVNGDEPDCVPCQEGKEYTDKAH
FSSKCRRCRLCDEGHGLEVEINCTRTQNTKCRCKPNFFCNSTVCEHCD
PCTKCEHGIIKECTLTSNTKCKEEGSRSNLGWLCLLLLPIPLIVWVKE
KEVQKTCRKHRKENQGSHESPTLNPETVAINLSDVDLSKYITTIAGVM
TLSQVKGFVRKNGVNEAKIDEIKNDNVQDTAEQKVQLLRNWHQLHGKK
EAYDTLIKDLKKANLCTLAEKIQTIILKDITSDSENSNFRNEIQSLV FAS LIGAND (SEQ ID NO: 9)
NCBI ACCESSION NO.: NP 000630
MQQPFNYPYPQIYWVDSSASSPWAPPGTVLPCPTSVPRRPGQRRPPPP
PPPPPLPPPPPPPPLPPLPLPPLKKRGNHSTGLCLLVMFPMVLVALVG
LGLGMFQLFHLQKELAELRESTSQMHTASSLEKQIGHPSPPPEKKELR
KVAHLTGKSNSRSMPLEWEDTYGIVLLSGVKYKKGGLVINETGLYFVY
SKVYFRGQSCNNLPLSHKVYMRNSKYPQDLVMMEGKMMSYCTTGQMWA
RSSYLGAVFNLTSADHLYVNVSELSLVNFEESQTFFGLYKL

---

What is claimed is:

1. A method of detecting apoptosis in a mammalian cell comprising:
   (a) contacting the cell with an antibody that binds to a protein fragment generated during apoptosis, wherein the antibody binds to a protein fragment of AP2-α (SEQ ID NO: 1)
   (b) determining the amount of the antibody which binds to the protein fragment of AP2-α generated during apoptosis; and
   (c) comparing the amount of antibody bound in step (b) with the amount of antibody which binds to the protein fragment of AP2-α in a mammalian cell free of apoptosis, wherein if the amount in step (b) is greater than the amount in the cell free of apoptosis, then apoptosis is detected.

2. The method of claim 1, wherein apoptosis in the cell is initiated by contacting the cell with Apo2L/TRAIL (SEQ ID NO: 7), FasL (SEQ ID NO: 9), a Fas agonist antibody, a DR4 agonist antibody or a DR5 agonist antibody.

3. The method of claim 2, further comprising obtaining the cell from a mammal experiencing a therapy including the administration of an apoptosis inducing agent comprising Apo2L/TRAIL (SEQ ID NO: 7), FasL (SEQ ID NO: 9), a Fas agonist antibody, a DR4 agonist antibody or a DR5 agonist antibody, and;

observing apoptosis of the cell from a mammal experiencing the therapy to obtain information on the efficacy of the therapy comprising the administration of Apo2L/TRAIL (SEQ ID NO: 7), FasL (SEQ ID NO: 9), a Fas agonist antibody, a DR4 agonist antibody or a DR5 agonist antibody.

4. The method of claim 1 wherein the protein fragment of AP2α bound by the antibody is 64 kDa or 33 kDa.

5. The method of claim 1 wherein the protein fragment bound by the antibody comprises DVFD, residues 684 to 687 of SEQ ID NO: 1 or GPAA, residues 688 to 691 of SEQ ID NO: 1.

6. The method of claim 1, wherein the cell is a human colon, colorectal, lung, breast, prostate, bladder, kidney, ovarian, brain, melanoma, leukemia or myeloma cancer cell.

7. The method of claim 1, wherein the protein fragment of AP2-α (SEQ ID NO: 1) is observed using immunoblotting, an enzyme linked immunoadsorbent assay or immunohistochemistry.

8. The method of claim 1, further comprising examining the expression of at least one mRNA in the mammalian cell.

9. The method of claim 1, further comprising exposing the mammalian cell to one or more test agents prior to contacting the cell with an antibody such that the detection of apoptosis in the mammalian cell identifies the one or more test agents as an inducer of apoptosis in the mammalian cell.

* * * * *

SEQUENCE LISTING

<160> NUMBER OF SEQ ID NOS: 9

<210> SEQ ID NO 1
<211> LENGTH: 955
<212> TYPE: PRT
<213> ORGANISM: Homo sapiens

<400> SEQUENCE: 1

Met Pro Ala Val Ser Lys Gly Asp Gly Met Arg Gly Leu Ala Val Phe
1               5                   10                  15

Ile Ser Asp Ile Arg Asn Cys Lys Ser Lys Glu Ala Glu Ile Lys Arg

-continued

```
                20                  25                  30
Ile Asn Lys Glu Leu Ala Asn Ile Arg Ser Lys Phe Lys Gly Asp Lys
             35                  40                  45

Ala Leu Asp Gly Tyr Ser Lys Lys Tyr Val Cys Lys Leu Leu Phe
 50                  55                  60

Ile Phe Leu Leu Gly His Asp Ile Asp Phe Gly His Met Glu Ala Val
 65                  70                  75                  80

Asn Leu Leu Ser Ser Asn Lys Tyr Thr Glu Lys Gln Ile Gly Tyr Leu
             85                  90                  95

Phe Ile Ser Val Leu Val Asn Ser Asn Ser Glu Leu Ile Arg Leu Ile
                100                 105                 110

Asn Asn Ala Ile Lys Asn Asp Leu Ala Ser Arg Asn Pro Thr Phe Met
             115                 120                 125

Cys Leu Ala Leu His Cys Ile Ala Asn Val Gly Ser Arg Glu Met Gly
         130                 135                 140

Glu Ala Phe Ala Ala Asp Ile Pro Arg Ile Leu Val Ala Gly Asp Ser
145                 150                 155                 160

Met Asp Ser Val Lys Gln Ser Ala Ala Leu Cys Leu Leu Arg Leu Tyr
                165                 170                 175

Lys Ala Ser Pro Asp Leu Val Pro Met Gly Glu Trp Thr Ala Arg Val
             180                 185                 190

Val His Leu Leu Asn Asp Gln His Met Gly Val Val Thr Ala Ala Val
         195                 200                 205

Ser Leu Ile Thr Cys Leu Cys Lys Lys Asn Pro Asp Asp Phe Lys Thr
     210                 215                 220

Cys Val Ser Leu Ala Val Ser Arg Leu Ser Arg Ile Val Ser Ser Ala
225                 230                 235                 240

Ser Thr Asp Leu Gln Asp Tyr Thr Tyr Tyr Phe Val Pro Ala Pro Trp
                245                 250                 255

Leu Ser Val Lys Leu Leu Arg Leu Leu Gln Cys Tyr Pro Pro Pro Glu
             260                 265                 270

Asp Ala Ala Val Lys Gly Arg Leu Val Glu Cys Leu Glu Thr Val Leu
         275                 280                 285

Asn Lys Ala Gln Glu Pro Pro Lys Ser Lys Val Gln His Ser Asn
     290                 295                 300

Ala Lys Asn Ala Ile Leu Phe Glu Thr Ile Ser Leu Ile His Tyr
305                 310                 315                 320

Asp Ser Glu Pro Asn Leu Leu Val Arg Ala Cys Asn Gln Leu Gly Gln
                325                 330                 335

Phe Leu Gln His Arg Glu Thr Asn Leu Arg Tyr Leu Ala Leu Glu Ser
             340                 345                 350

Met Cys Thr Leu Ala Ser Ser Glu Phe Ser His Glu Ala Val Lys Thr
         355                 360                 365

His Ile Asp Thr Val Ile Asn Ala Leu Lys Thr Glu Arg Asp Val Ser
     370                 375                 380

Val Arg Gln Arg Ala Ala Asp Leu Leu Tyr Ala Met Cys Asp Arg Ser
385                 390                 395                 400

Asn Ala Lys Gln Ile Val Ser Glu Met Leu Arg Tyr Leu Glu Thr Ala
                405                 410                 415

Asp Tyr Ala Ile Arg Glu Glu Ile Val Leu Lys Val Ala Ile Leu Ala
             420                 425                 430

Glu Lys Tyr Ala Val Asp Tyr Ser Trp Tyr Val Asp Thr Ile Leu Asn
         435                 440                 445
```

```
Leu Ile Arg Ile Ala Gly Asp Tyr Val Ser Glu Glu Val Trp Tyr Arg
450                 455                 460
Val Leu Gln Ile Val Thr Asn Arg Asp Asp Val Gln Gly Tyr Ala Ala
465                 470                 475                 480
Lys Thr Val Phe Glu Ala Leu Gln Ala Pro Ala Cys His Glu Asn Met
                485                 490                 495
Val Lys Val Gly Gly Tyr Ile Leu Gly Glu Phe Gly Asn Leu Ile Ala
            500                 505                 510
Gly Asp Pro Arg Ser Ser Pro Val Gln Phe Ser Leu Leu His Ser
        515                 520                 525
Lys Phe His Leu Cys Ser Val Ala Thr Arg Ala Leu Leu Leu Ser Thr
530                 535                 540
Tyr Ile Lys Phe Ile Asn Leu Phe Pro Glu Thr Lys Ala Thr Ile Gln
545                 550                 555                 560
Gly Val Leu Arg Ala Gly Ser Gln Leu Arg Asn Ala Asp Val Glu Leu
                565                 570                 575
Gln Gln Arg Ala Val Glu Tyr Leu Thr Leu Ser Ser Val Ala Ser Thr
            580                 585                 590
Asp Val Leu Ala Thr Val Leu Glu Glu Met Pro Pro Phe Pro Glu Arg
        595                 600                 605
Glu Ser Ser Ile Leu Ala Lys Leu Lys Arg Lys Lys Gly Pro Gly Ala
610                 615                 620
Gly Ser Ala Leu Asp Asp Gly Arg Arg Asp Pro Ser Ser Asn Asp Ile
625                 630                 635                 640
Asn Gly Gly Met Glu Pro Thr Pro Ser Thr Val Ser Thr Pro Ser Pro
                645                 650                 655
Ser Ala Asp Leu Leu Gly Leu Arg Ala Ala Pro Pro Ala Ala Pro
            660                 665                 670
Pro Ala Ser Ala Gly Ala Gly Asn Leu Leu Val Asp Val Phe Asp Gly
        675                 680                 685
Pro Ala Ala Gln Pro Ser Leu Gly Pro Thr Pro Glu Glu Ala Phe Leu
690                 695                 700
Ser Pro Gly Pro Glu Asp Ile Gly Pro Ile Pro Glu Ala Asp Glu
705                 710                 715                 720
Leu Leu Asn Lys Phe Val Cys Lys Asn Gly Val Leu Phe Glu Asn
                725                 730                 735
Gln Leu Leu Gln Ile Gly Val Lys Ser Glu Phe Arg Gln Asn Leu Gly
            740                 745                 750
Arg Met Tyr Leu Phe Tyr Gly Asn Lys Thr Ser Val Gln Phe Gln Asn
        755                 760                 765
Phe Ser Pro Thr Val Val His Pro Gly Asp Leu Gln Thr Gln Leu Ala
770                 775                 780
Val Gln Thr Lys Arg Val Ala Ala Gln Val Asp Gly Gly Ala Gln Val
785                 790                 795                 800
Gln Gln Val Leu Asn Ile Glu Cys Leu Arg Asp Phe Leu Thr Pro Pro
                805                 810                 815
Leu Leu Ser Val Arg Phe Arg Tyr Gly Gly Ala Pro Gln Ala Leu Thr
            820                 825                 830
Leu Lys Leu Pro Val Thr Ile Asn Lys Phe Phe Gln Pro Thr Glu Met
        835                 840                 845
Ala Ala Gln Asp Phe Phe Gln Arg Trp Lys Gln Leu Ser Leu Pro Gln
850                 855                 860
Gln Glu Ala Gln Lys Ile Phe Lys Ala Asn His Pro Met Asp Ala Glu
865                 870                 875                 880
```

```
Val Thr Lys Ala Lys Leu Leu Gly Phe Gly Ser Ala Leu Leu Asp Asn
            885                 890                 895

Val Asp Pro Asn Pro Glu Asn Phe Val Gly Ala Gly Ile Ile Gln Thr
        900                 905                 910

Lys Ala Leu Gln Val Gly Cys Leu Arg Leu Glu Pro Asn Ala Gln
    915                 920                 925

Ala Gln Met Tyr Arg Leu Thr Leu Arg Thr Ser Lys Glu Pro Val Ser
    930                 935                 940

Arg His Leu Cys Glu Leu Leu Ala Gln Gln Phe
945                 950                 955

<210> SEQ ID NO 2
<211> LENGTH: 1675
<212> TYPE: PRT
<213> ORGANISM: Homo sapiens

<400> SEQUENCE: 2

Met Ala Gln Ile Leu Pro Ile Arg Phe Gln Glu His Leu Gln Leu Gln
  1               5                  10                  15

Asn Leu Gly Ile Asn Pro Ala Asn Ile Gly Phe Ser Thr Leu Thr Met
                 20                  25                  30

Glu Ser Asp Lys Phe Ile Cys Ile Arg Glu Lys Val Gly Glu Gln Ala
            35                  40                  45

Gln Val Val Ile Ile Asp Met Asn Asp Pro Ser Asn Pro Ile Arg Arg
        50                  55                  60

Pro Ile Ser Ala Asp Ser Ala Ile Met Asn Pro Ala Ser Lys Val Ile
 65                  70                  75                  80

Ala Leu Lys Ala Gly Lys Thr Leu Gln Ile Phe Asn Ile Glu Met Lys
                 85                  90                  95

Ser Lys Met Lys Ala His Thr Met Thr Asp Asp Val Thr Phe Trp Lys
            100                 105                 110

Trp Ile Ser Leu Asn Thr Val Ala Leu Val Thr Asp Asn Ala Val Tyr
        115                 120                 125

His Trp Ser Met Glu Gly Glu Ser Gln Pro Val Lys Met Phe Asp Arg
    130                 135                 140

His Ser Ser Leu Ala Gly Cys Gln Ile Ile Asn Tyr Arg Thr Asp Ala
145                 150                 155                 160

Lys Gln Lys Trp Leu Leu Leu Thr Gly Ile Ser Ala Gln Gln Asn Arg
                165                 170                 175

Val Val Gly Ala Met Gln Leu Tyr Ser Val Asp Arg Lys Val Ser Gln
            180                 185                 190

Pro Ile Glu Gly His Ala Ala Ser Phe Ala Gln Phe Lys Met Glu Gly
        195                 200                 205

Asn Ala Glu Glu Ser Thr Leu Phe Cys Phe Ala Val Arg Gly Gln Ala
    210                 215                 220

Gly Gly Lys Leu His Ile Ile Glu Val Gly Thr Pro Pro Thr Gly Asn
225                 230                 235                 240

Gln Pro Phe Pro Lys Lys Ala Val Asp Val Phe Phe Pro Pro Glu Ala
                245                 250                 255

Gln Asn Asp Phe Pro Val Ala Met Gln Ile Ser Glu Lys His Asp Val
            260                 265                 270

Val Phe Leu Ile Thr Lys Tyr Gly Tyr Ile His Leu Tyr Asp Leu Glu
        275                 280                 285

Thr Gly Thr Cys Ile Tyr Met Asn Arg Ile Ser Gly Glu Thr Ile Phe
    290                 295                 300
```

```
Val Thr Ala Pro His Glu Ala Thr Ala Gly Ile Ile Gly Val Asn Arg
305                 310                 315                 320

Lys Gly Gln Val Leu Ser Val Cys Val Glu Glu Asn Ile Ile Pro
            325                 330                 335

Tyr Ile Thr Asn Val Leu Gln Asn Pro Asp Leu Ala Leu Arg Met Ala
            340                 345                 350

Val Arg Asn Asn Leu Ala Gly Ala Glu Glu Leu Phe Ala Arg Lys Phe
            355                 360                 365

Asn Ala Leu Phe Ala Gln Gly Asn Tyr Ser Glu Ala Ala Lys Val Ala
            370                 375                 380

Ala Asn Ala Pro Lys Gly Ile Leu Arg Thr Pro Asp Thr Ile Arg Arg
385                 390                 395                 400

Phe Gln Ser Val Pro Ala Gln Pro Gly Gln Thr Ser Pro Leu Leu Gln
            405                 410                 415

Tyr Phe Gly Ile Leu Leu Asp Gln Gly Gln Leu Asn Lys Tyr Glu Ser
            420                 425                 430

Leu Glu Leu Cys Arg Pro Val Leu Gln Gln Gly Arg Lys Gln Leu Leu
            435                 440                 445

Glu Lys Trp Leu Lys Glu Asp Lys Leu Glu Cys Ser Glu Glu Leu Gly
            450                 455                 460

Asp Leu Val Lys Ser Val Asp Pro Thr Leu Ala Leu Ser Val Tyr Leu
465                 470                 475                 480

Arg Ala Asn Val Pro Asn Lys Val Ile Gln Cys Phe Ala Glu Thr Gly
            485                 490                 495

Gln Val Gln Lys Ile Val Leu Tyr Ala Lys Lys Val Gly Tyr Thr Pro
            500                 505                 510

Asp Trp Ile Phe Leu Leu Arg Asn Val Met Arg Ile Ser Pro Asp Gln
            515                 520                 525

Gly Gln Gln Phe Ala Gln Met Leu Val Gln Asp Glu Glu Pro Leu Ala
            530                 535                 540

Asp Ile Thr Gln Ile Val Asp Val Phe Met Glu Tyr Asn Leu Ile Gln
545                 550                 555                 560

Gln Cys Thr Ala Phe Leu Leu Asp Ala Leu Lys Asn Asn Arg Pro Ser
            565                 570                 575

Glu Gly Pro Leu Gln Thr Arg Leu Leu Glu Met Asn Leu Met His Ala
            580                 585                 590

Pro Gln Val Ala Asp Ala Ile Leu Gly Asn Gln Met Phe Thr His Tyr
            595                 600                 605

Asp Arg Ala His Ile Ala Gln Leu Cys Glu Lys Ala Gly Leu Leu Gln
            610                 615                 620

Arg Ala Leu Glu His Phe Thr Asp Leu Tyr Asp Ile Lys Arg Ala Val
625                 630                 635                 640

Val His Thr His Leu Leu Asn Pro Glu Trp Leu Val Asn Tyr Phe Gly
            645                 650                 655

Ser Leu Ser Val Glu Asp Ser Leu Glu Cys Leu Arg Ala Met Leu Ser
            660                 665                 670

Ala Asn Ile Arg Gln Asn Leu Gln Ile Cys Val Gln Val Ala Ser Lys
            675                 680                 685

Tyr His Glu Gln Leu Ser Thr Gln Ser Leu Ile Glu Leu Phe Glu Ser
            690                 695                 700

Phe Lys Ser Phe Glu Gly Leu Phe Tyr Phe Leu Gly Ser Ile Val Asn
705                 710                 715                 720

Phe Ser Gln Asp Pro Asp Val His Phe Lys Tyr Ile Gln Ala Ala Cys
```

```
                        725                 730                 735
Lys Thr Gly Gln Ile Lys Glu Val Glu Arg Ile Cys Arg Glu Ser Asn
            740                 745                 750

Cys Tyr Asp Pro Glu Arg Val Lys Asn Phe Leu Lys Glu Ala Lys Leu
        755                 760                 765

Thr Asp Gln Leu Pro Leu Ile Ile Val Cys Asp Arg Phe Asp Phe Val
    770                 775                 780

His Asp Leu Val Leu Tyr Leu Tyr Arg Asn Asn Leu Gln Lys Tyr Ile
785                 790                 795                 800

Glu Ile Tyr Val Gln Lys Val Asn Pro Ser Arg Leu Pro Val Val Ile
                805                 810                 815

Gly Gly Leu Leu Asp Val Asp Cys Ser Glu Asp Val Ile Lys Asn Leu
            820                 825                 830

Ile Leu Val Val Arg Gly Gln Phe Ser Thr Asp Glu Leu Val Ala Glu
        835                 840                 845

Val Glu Lys Arg Asn Arg Leu Lys Leu Leu Pro Trp Leu Glu Ala
    850                 855                 860

Arg Ile His Glu Gly Cys Glu Pro Ala Thr His Asn Ala Leu Ala
865                 870                 875                 880

Lys Ile Tyr Ile Asp Ser Asn Asn Pro Glu Arg Phe Leu Arg Glu
                885                 890                 895

Asn Pro Tyr Tyr Asp Ser Arg Val Val Gly Lys Tyr Cys Glu Lys Arg
                900                 905                 910

Asp Pro His Leu Ala Cys Val Ala Tyr Glu Arg Gly Gln Cys Asp Leu
            915                 920                 925

Glu Leu Ile Asn Val Cys Asn Glu Asn Ser Leu Phe Lys Ser Leu Ser
    930                 935                 940

Arg Tyr Leu Val Arg Arg Lys Asp Pro Glu Leu Trp Gly Ser Val Leu
945                 950                 955                 960

Leu Glu Ser Asn Pro Tyr Arg Arg Pro Leu Ile Asp Gln Val Val Gln
                965                 970                 975

Thr Ala Leu Ser Glu Thr Gln Asp Pro Glu Glu Val Ser Val Thr Val
            980                 985                 990

Lys Ala Phe Met Thr Ala Asp Leu Pro Asn Glu Leu Ile Glu Leu Leu
        995                 1000                1005

Glu Lys Ile Val Leu Asp Asn Ser Val Phe Ser Glu His Arg Asn Leu
    1010                1015                1020

Gln Asn Leu Leu Ile Leu Thr Ala Ile Lys Ala Asp Arg Thr Arg Val
1025                1030                1035                1040

Met Glu Tyr Ile Asn Arg Leu Asp Asn Tyr Asp Ala Pro Asp Ile Ala
                1045                1050                1055

Asn Ile Ala Ile Ser Asn Glu Leu Phe Glu Glu Ala Phe Ala Ile Phe
            1060                1065                1070

Arg Lys Phe Asp Val Asn Thr Ser Ala Val Gln Val Leu Ile Glu His
        1075                1080                1085

Ile Gly Asn Leu Asp Arg Ala Tyr Glu Phe Ala Glu Arg Cys Asn Glu
    1090                1095                1100

Pro Ala Val Trp Ser Gln Leu Ala Lys Ala Gln Leu Gln Lys Gly Met
1105                1110                1115                1120

Val Lys Glu Ala Ile Asp Ser Tyr Ile Lys Ala Asp Asp Pro Ser Ser
                1125                1130                1135

Tyr Met Glu Val Val Gln Ala Ala Asn Thr Ser Gly Asn Trp Glu Glu
            1140                1145                1150
```

```
Leu Val Lys Tyr Leu Gln Met Ala Arg Lys Ala Arg Glu Ser Tyr
    1155                1160                1165

Val Glu Thr Glu Leu Ile Phe Ala Leu Ala Lys Thr Asn Arg Leu Ala
    1170                1175                1180

Glu Leu Glu Glu Phe Ile Asn Gly Pro Asn Asn Ala His Ile Gln Gln
1185                1190                1195                1200

Val Gly Asp Arg Cys Tyr Asp Glu Lys Met Tyr Asp Ala Ala Lys Leu
                1205                1210                1215

Leu Tyr Asn Asn Val Ser Asn Phe Gly Arg Leu Ala Ser Thr Leu Val
                1220                1225                1230

His Leu Gly Glu Tyr Gln Ala Ala Val Asp Gly Ala Arg Lys Ala Asn
    1235                1240                1245

Ser Thr Arg Thr Trp Lys Glu Val Cys Phe Ala Cys Val Asp Gly Lys
    1250                1255                1260

Glu Phe Arg Leu Ala Gln Met Cys Gly Leu His Ile Val His Ala
1265                1270                1275                1280

Asp Glu Leu Glu Glu Leu Ile Asn Tyr Tyr Gln Asp Arg Gly Tyr Phe
                1285                1290                1295

Glu Glu Leu Ile Thr Met Leu Glu Ala Ala Leu Gly Leu Glu Arg Ala
                1300                1305                1310

His Met Gly Met Phe Thr Glu Leu Ala Ile Leu Tyr Ser Lys Phe Lys
    1315                1320                1325

Pro Gln Lys Met Arg Glu His Leu Glu Leu Phe Trp Ser Arg Val Asn
    1330                1335                1340

Ile Pro Lys Val Leu Arg Ala Ala Glu Gln Ala His Leu Trp Ala Glu
1345                1350                1355                1360

Leu Val Phe Leu Tyr Asp Lys Tyr Glu Glu Tyr Asp Asn Ala Ile Ile
                1365                1370                1375

Thr Met Met Asn His Pro Thr Asp Ala Trp Lys Glu Gly Gln Phe Lys
                1380                1385                1390

Asp Ile Ile Thr Lys Val Ala Asn Val Glu Leu Tyr Tyr Arg Ala Ile
                1395                1400                1405

Gln Phe Tyr Leu Glu Phe Lys Pro Leu Leu Leu Asn Asp Leu Leu Met
    1410                1415                1420

Val Leu Ser Pro Arg Leu Asp His Thr Arg Ala Val Asn Tyr Phe Ser
1425                1430                1435                1440

Lys Val Lys Gln Leu Pro Leu Val Lys Pro Tyr Leu Arg Ser Val Gln
                1445                1450                1455

Asn His Asn Asn Lys Ser Val Asn Glu Ser Leu Asn Asn Leu Phe Ile
                1460                1465                1470

Thr Glu Glu Asp Tyr Gln Ala Leu Arg Thr Ser Ile Asp Ala Tyr Asp
                1475                1480                1485

Asn Phe Asp Asn Ile Ser Leu Ala Gln Arg Leu Glu Lys His Glu Leu
    1490                1495                1500

Ile Glu Phe Arg Arg Ile Ala Ala Tyr Leu Phe Lys Gly Asn Asn Arg
1505                1510                1515                1520

Trp Lys Gln Ser Val Glu Leu Cys Lys Lys Asp Ser Leu Tyr Lys Asp
                1525                1530                1535

Ala Met Gln Tyr Ala Ser Glu Ser Lys Asp Thr Glu Leu Ala Glu Glu
                1540                1545                1550

Leu Leu Gln Trp Phe Leu Gln Glu Glu Lys Arg Glu Cys Phe Gly Ala
    1555                1560                1565

Cys Leu Phe Thr Cys Tyr Asp Leu Leu Arg Pro Asp Val Val Leu Glu
    1570                1575                1580
```

Thr Ala Trp Arg His Asn Ile Met Asp Phe Ala Met Pro Tyr Phe Ile
1585                1590                1595                1600

Gln Val Met Lys Glu Tyr Leu Thr Lys Val Asp Lys Leu Asp Ala Ser
            1605                1610                1615

Glu Ser Leu Arg Lys Glu Glu Gln Ala Thr Glu Thr Gln Pro Ile
        1620                1625                1630

Val Tyr Gly Gln Pro Gln Leu Met Leu Thr Ala Gly Pro Ser Val Ala
    1635                1640                1645

Val Pro Pro Gln Ala Pro Phe Gly Tyr Gly Tyr Thr Ala Pro Pro Tyr
1650                1655                1660

Gly Gln Pro Gln Pro Gly Phe Gly Tyr Ser Met
1665                1670                1675

<210> SEQ ID NO 3
<211> LENGTH: 937
<212> TYPE: PRT
<213> ORGANISM: Homo sapiens

<400> SEQUENCE: 3

Met Thr Asp Ser Lys Tyr Phe Thr Thr Asn Lys Lys Gly Glu Ile Phe
1               5                   10                  15

Glu Leu Lys Ala Glu Leu Asn Asn Glu Lys Lys Glu Lys Arg Lys Glu
            20                  25                  30

Ala Val Lys Lys Val Ile Ala Ala Met Thr Val Gly Lys Asp Val Ser
        35                  40                  45

Ser Leu Phe Pro Asp Val Val Asn Cys Met Gln Thr Asp Asn Leu Glu
    50                  55                  60

Leu Lys Lys Leu Val Tyr Leu Tyr Leu Met Asn Tyr Ala Lys Ser Gln
65                  70                  75                  80

Pro Asp Met Ala Ile Met Ala Val Asn Ser Phe Val Lys Asp Cys Glu
                85                  90                  95

Asp Pro Asn Pro Leu Ile Arg Ala Leu Ala Val Arg Thr Met Gly Cys
            100                 105                 110

Ile Arg Val Asp Lys Ile Thr Glu Tyr Leu Cys Glu Pro Leu Arg Lys
        115                 120                 125

Cys Leu Lys Asp Glu Asp Pro Tyr Val Arg Lys Thr Ala Ala Val Cys
    130                 135                 140

Val Ala Lys Leu His Asp Ile Asn Ala Gln Met Val Glu Asp Gln Gly
145                 150                 155                 160

Phe Leu Asp Ser Leu Arg Asp Leu Ile Ala Asp Ser Asn Pro Met Val
                165                 170                 175

Val Ala Asn Ala Val Ala Ala Leu Ser Glu Ile Ser Glu Ser His Pro
            180                 185                 190

Asn Ser Asn Leu Leu Asp Leu Asn Pro Gln Asn Ile Asn Lys Leu Leu
        195                 200                 205

Thr Ala Leu Asn Glu Cys Thr Glu Trp Gly Gln Ile Phe Ile Leu Asp
    210                 215                 220

Cys Leu Ser Asn Tyr Asn Pro Lys Asp Asp Arg Glu Ala Gln Ser Ile
225                 230                 235                 240

Cys Glu Arg Val Thr Pro Arg Leu Ser His Ala Asn Ser Ala Val Val
                245                 250                 255

Leu Ser Ala Val Lys Val Leu Met Lys Phe Leu Glu Leu Leu Pro Lys
            260                 265                 270

Asp Ser Asp Tyr Tyr Asn Met Leu Leu Lys Lys Leu Ala Pro Pro Leu
        275                 280                 285

-continued

```
Val Thr Leu Leu Ser Gly Glu Pro Glu Val Gln Tyr Val Ala Leu Arg
    290                 295                 300

Asn Ile Asn Leu Ile Val Gln Lys Arg Pro Glu Ile Leu Lys Gln Glu
305                 310                 315                 320

Ile Lys Val Phe Phe Val Lys Tyr Asn Asp Pro Ile Tyr Val Lys Leu
                325                 330                 335

Glu Lys Leu Asp Ile Met Ile Arg Leu Ala Ser Gln Ala Asn Ile Ala
            340                 345                 350

Gln Val Leu Ala Glu Leu Lys Glu Tyr Ala Thr Glu Val Asp Val Asp
        355                 360                 365

Phe Val Arg Lys Ala Val Arg Ala Ile Gly Arg Cys Ala Ile Lys Val
    370                 375                 380

Glu Gln Ser Ala Glu Arg Cys Val Ser Thr Leu Leu Asp Leu Ile Gln
385                 390                 395                 400

Thr Lys Val Asn Tyr Val Val Gln Glu Ala Ile Val Val Ile Arg Asp
                405                 410                 415

Ile Phe Arg Lys Tyr Pro Asn Lys Tyr Glu Ser Ile Ile Ala Thr Leu
            420                 425                 430

Cys Glu Asn Leu Asp Ser Leu Asp Glu Pro Asp Ala Arg Ala Ala Met
        435                 440                 445

Ile Trp Ile Val Gly Glu Tyr Ala Glu Arg Ile Asp Asn Ala Asp Glu
    450                 455                 460

Leu Leu Glu Ser Phe Leu Glu Gly Phe His Asp Glu Ser Thr Gln Val
465                 470                 475                 480

Gln Leu Thr Leu Leu Thr Ala Ile Val Lys Leu Phe Leu Lys Lys Pro
                485                 490                 495

Ser Glu Thr Gln Glu Leu Val Gln Gln Val Leu Ser Leu Ala Thr Gln
            500                 505                 510

Asp Ser Asp Asn Pro Asp Leu Arg Asp Arg Gly Tyr Ile Tyr Trp Arg
        515                 520                 525

Leu Leu Ser Thr Asp Pro Val Thr Ala Lys Glu Val Val Leu Ser Glu
    530                 535                 540

Lys Pro Leu Ile Ser Glu Glu Thr Asp Leu Ile Glu Pro Thr Leu Leu
545                 550                 555                 560

Asp Glu Leu Ile Cys His Ile Gly Ser Leu Ala Ser Val Tyr His Lys
                565                 570                 575

Pro Pro Asn Ala Phe Val Glu Gly Ser His Gly Ile His Arg Lys His
            580                 585                 590

Leu Pro Ile His His Gly Ser Thr Asp Ala Gly Asp Ser Pro Val Gly
        595                 600                 605

Thr Thr Thr Ala Thr Asn Leu Glu Gln Pro Gln Val Ile Pro Ser Gln
    610                 615                 620

Gly Asp Leu Leu Gly Asp Leu Leu Asn Leu Asp Leu Gly Pro Pro Val
625                 630                 635                 640

Asn Val Pro Gln Val Ser Ser Met Gln Met Gly Ala Val Asp Leu Leu
                645                 650                 655

Gly Gly Gly Leu Asp Ser Leu Val Gly Gln Ser Phe Ile Pro Ser Ser
            660                 665                 670

Val Pro Ala Thr Phe Ala Pro Ser Pro Thr Pro Ala Val Val Ser Ser
        675                 680                 685

Gly Leu Asn Asp Leu Phe Glu Leu Ser Thr Gly Ile Gly Met Ala Pro
    690                 695                 700

Gly Gly Tyr Val Ala Pro Lys Ala Val Trp Leu Pro Ala Val Lys Ala
```

```
                705                 710                 715                 720
Lys Gly Leu Glu Ile Ser Gly Thr Phe Thr His Arg Gln Gly His Ile
                    725                 730                 735
Tyr Met Glu Met Asn Phe Thr Asn Lys Ala Leu Gln His Met Thr Asp
                740                 745                 750
Phe Ala Ile Gln Phe Asn Lys Asn Ser Phe Gly Val Ile Pro Ser Thr
                755                 760                 765
Pro Leu Ala Ile His Thr Pro Leu Met Pro Asn Gln Ser Ile Asp Val
            770                 775                 780
Ser Leu Pro Leu Asn Thr Leu Gly Pro Val Met Lys Met Glu Pro Leu
785                 790                 795                 800
Asn Asn Leu Gln Val Ala Val Lys Asn Asn Ile Asp Val Phe Tyr Phe
                805                 810                 815
Ser Cys Leu Ile Pro Leu Asn Val Leu Phe Val Glu Asp Gly Lys Met
                820                 825                 830
Glu Arg Gln Val Phe Leu Ala Thr Trp Lys Asp Ile Pro Asn Glu Asn
            835                 840                 845
Glu Leu Gln Phe Gln Ile Lys Glu Cys His Leu Asn Ala Asp Thr Val
        850                 855                 860
Ser Ser Lys Leu Gln Asn Asn Asn Val Tyr Thr Ile Ala Lys Arg Asn
865                 870                 875                 880
Val Glu Gly Gln Asp Met Leu Tyr Gln Ser Leu Lys Leu Thr Asn Gly
                885                 890                 895
Ile Trp Ile Leu Ala Glu Leu Arg Ile Gln Pro Gly Asn Pro Asn Tyr
            900                 905                 910
Thr Leu Ser Leu Lys Cys Arg Ala Pro Glu Val Ser Gln Tyr Ile Tyr
        915                 920                 925
Gln Val Tyr Asp Ser Ile Leu Lys Asn
    930                 935

<210> SEQ ID NO 4
<211> LENGTH: 851
<212> TYPE: PRT
<213> ORGANISM: Homo sapiens

<400> SEQUENCE: 4

Met Gly Asn Arg Gly Met Glu Asp Leu Ile Pro Leu Val Asn Arg Leu
1               5                   10                  15
Gln Asp Ala Phe Ser Ala Ile Gly Gln Asn Ala Asp Leu Asp Leu Pro
            20                  25                  30
Gln Ile Ala Val Val Gly Gly Gln Ser Ala Gly Lys Ser Ser Val Leu
        35                  40                  45
Glu Asn Phe Val Gly Arg Asp Phe Leu Pro Arg Gly Ser Gly Ile Val
    50                  55                  60
Thr Arg Arg Pro Leu Val Leu Gln Leu Val Asn Ala Thr Thr Glu Tyr
65                  70                  75                  80
Ala Glu Phe Leu His Cys Lys Gly Lys Lys Phe Thr Asp Phe Glu Glu
                85                  90                  95
Val Arg Leu Glu Ile Glu Ala Glu Thr Asp Arg Val Thr Gly Thr Asn
            100                 105                 110
Lys Gly Ile Ser Pro Val Pro Ile Asn Leu Arg Val Tyr Ser Pro His
        115                 120                 125
Val Leu Asn Leu Thr Leu Val Asp Leu Pro Gly Met Thr Lys Val Pro
    130                 135                 140

Val Gly Asp Gln Pro Pro Asp Ile Glu Phe Gln Ile Arg Asp Met Leu
```

```
            145                 150                 155                 160
        Met Gln Phe Val Thr Lys Glu Asn Cys Leu Ile Leu Ala Val Ser Pro
                        165                 170                 175
        Ala Asn Ser Asp Leu Ala Asn Ser Asp Ala Leu Lys Val Ala Lys Glu
                        180                 185                 190
        Val Asp Pro Gln Gly Gln Arg Thr Ile Gly Val Ile Thr Lys Leu Asp
                        195                 200                 205
        Leu Met Asp Glu Gly Thr Asp Ala Arg Asp Val Leu Glu Asn Lys Leu
                        210                 215                 220
        Leu Pro Leu Arg Arg Gly Tyr Ile Gly Val Val Asn Arg Ser Gln Lys
        225                 230                 235                 240
        Asp Ile Asp Gly Lys Lys Asp Ile Thr Ala Ala Leu Ala Ala Glu Arg
                        245                 250                 255
        Lys Phe Phe Leu Ser His Pro Ser Tyr Arg His Leu Ala Asp Arg Met
                        260                 265                 270
        Gly Thr Pro Tyr Leu Gln Lys Val Leu Asn Gln Gln Leu Thr Asn His
                        275                 280                 285
        Ile Arg Asp Thr Leu Pro Gly Leu Arg Asn Lys Leu Gln Ser Gln Leu
                        290                 295                 300
        Leu Ser Ile Glu Lys Glu Val Glu Glu Tyr Lys Asn Phe Arg Pro Asp
        305                 310                 315                 320
        Asp Pro Ala Arg Lys Thr Lys Ala Leu Leu Gln Met Val Gln Gln Phe
                        325                 330                 335
        Ala Val Asp Phe Glu Lys Arg Ile Glu Gly Ser Gly Asp Gln Ile Asp
                        340                 345                 350
        Thr Tyr Glu Leu Ser Gly Gly Ala Arg Ile Asn Arg Ile Phe His Glu
                        355                 360                 365
        Arg Phe Pro Phe Glu Leu Val Lys Met Glu Phe Asp Glu Lys Glu Leu
                        370                 375                 380
        Arg Arg Glu Ile Ser Tyr Ala Ile Lys Asn Ile His Gly Ile Arg Thr
        385                 390                 395                 400
        Gly Leu Phe Thr Pro Asp Met Ala Phe Glu Thr Ile Val Lys Lys Gln
                        405                 410                 415
        Val Lys Lys Ile Arg Glu Pro Cys Leu Lys Cys Val Asp Met Val Ile
                        420                 425                 430
        Ser Glu Leu Ile Ser Thr Val Arg Gln Cys Thr Lys Lys Leu Gln Gln
                        435                 440                 445
        Tyr Pro Arg Leu Arg Glu Glu Met Glu Arg Ile Val Thr Thr His Ile
                        450                 455                 460
        Arg Glu Arg Glu Gly Arg Thr Lys Glu Gln Val Met Leu Leu Ile Asp
        465                 470                 475                 480
        Ile Glu Leu Ala Tyr Met Asn Thr Asn His Glu Asp Phe Ile Gly Phe
                        485                 490                 495
        Ala Asn Ala Gln Gln Arg Ser Asn Gln Met Asn Lys Lys Lys Thr Ser
                        500                 505                 510
        Gly Asn Gln Asp Glu Ile Leu Val Ile Arg Lys Gly Trp Leu Thr Ile
                        515                 520                 525
        Asn Asn Ile Gly Ile Met Lys Gly Gly Ser Lys Glu Tyr Trp Phe Val
                        530                 535                 540
        Leu Thr Ala Glu Asn Leu Ser Trp Tyr Lys Asp Asp Glu Glu Lys Glu
        545                 550                 555                 560
        Lys Lys Tyr Met Leu Ser Val Asp Asn Leu Lys Leu Arg Asp Val Glu
                        565                 570                 575
```

-continued

```
Lys Gly Phe Met Ser Ser Lys His Ile Phe Ala Leu Phe Asn Thr Glu
            580                 585                 590

Gln Arg Asn Val Tyr Lys Asp Tyr Arg Gln Leu Glu Leu Ala Cys Glu
        595                 600                 605

Thr Gln Glu Glu Val Asp Ser Trp Lys Ala Ser Phe Leu Arg Ala Gly
610                 615                 620

Val Tyr Pro Glu Arg Val Gly Asp Lys Glu Lys Ala Ser Glu Thr Glu
625                 630                 635                 640

Glu Asn Gly Ser Asp Ser Phe Met His Ser Met Asp Pro Gln Leu Glu
                645                 650                 655

Arg Gln Val Glu Thr Ile Arg Asn Leu Val Asp Ser Tyr Met Ala Ile
            660                 665                 670

Val Asn Lys Thr Val Arg Asp Leu Met Pro Lys Thr Ile Met His Leu
        675                 680                 685

Met Ile Asn Asn Thr Lys Glu Phe Ile Phe Ser Glu Leu Leu Ala Asn
690                 695                 700

Leu Tyr Ser Cys Gly Asp Gln Asn Thr Leu Met Glu Glu Ser Ala Glu
705                 710                 715                 720

Gln Ala Gln Arg Arg Asp Glu Met Leu Arg Met Tyr His Ala Leu Lys
                725                 730                 735

Glu Ala Leu Ser Ile Ile Gly Asp Ile Asn Thr Thr Thr Val Ser Thr
            740                 745                 750

Pro Met Pro Pro Pro Val Asp Asp Ser Trp Leu Gln Val Gln Ser Val
        755                 760                 765

Pro Ala Gly Arg Arg Ser Pro Thr Ser Ser Pro Thr Pro Gln Arg Arg
770                 775                 780

Ala Pro Ala Val Pro Pro Ala Arg Pro Gly Ser Arg Gly Pro Ala Pro
785                 790                 795                 800

Gly Pro Pro Pro Ala Gly Ser Ala Leu Gly Ala Pro Pro Val Pro
                805                 810                 815

Ser Arg Pro Gly Ala Ser Pro Asp Pro Phe Gly Pro Pro Gln Val
                820                 825                 830

Pro Ser Arg Pro Asn Arg Ala Pro Pro Gly Val Pro Arg Ile Thr Ile
                835                 840                 845

Ser Asp Pro
    850

<210> SEQ ID NO 5
<211> LENGTH: 468
<212> TYPE: PRT
<213> ORGANISM: Homo sapiens

<400> SEQUENCE: 5

Met Ala Pro Pro Pro Ala Arg Val His Leu Gly Ala Phe Leu Ala Val
1               5                   10                  15

Thr Pro Asn Pro Gly Ser Ala Ala Ser Gly Thr Glu Ala Ala Ala Ala
            20                  25                  30

Thr Pro Ser Lys Val Trp Gly Ser Ser Ala Gly Arg Ile Glu Pro Arg
        35                  40                  45

Gly Gly Gly Arg Gly Ala Leu Pro Thr Ser Met Gly Gln His Gly Pro
50                  55                  60

Ser Ala Arg Ala Arg Ala Gly Arg Ala Pro Gly Pro Arg Pro Ala Arg
65                  70                  75                  80

Glu Ala Ser Pro Arg Leu Arg Val His Lys Thr Phe Lys Phe Val Val
                85                  90                  95
```

```
Val Gly Val Leu Leu Gln Val Pro Ser Ala Ala Thr Ile Lys
            100                 105                 110

Leu His Asp Gln Ser Ile Gly Thr Gln Gln Trp Glu His Ser Pro Leu
        115                 120                 125

Gly Glu Leu Cys Pro Pro Gly Ser His Arg Ser Glu His Pro Gly Ala
    130                 135                 140

Cys Asn Arg Cys Thr Glu Gly Val Gly Tyr Thr Asn Ala Ser Asn Asn
145                 150                 155                 160

Leu Phe Ala Cys Leu Pro Cys Thr Ala Cys Lys Ser Asp Glu Glu Glu
                165                 170                 175

Arg Ser Pro Cys Thr Thr Thr Arg Asn Thr Ala Cys Gln Cys Lys Pro
            180                 185                 190

Gly Thr Phe Arg Asn Asp Asn Ser Ala Glu Met Cys Arg Lys Cys Ser
        195                 200                 205

Arg Gly Cys Pro Arg Gly Met Val Lys Val Lys Asp Cys Thr Pro Trp
    210                 215                 220

Ser Asp Ile Glu Cys Val His Lys Glu Ser Gly Asn Gly His Asn Ile
225                 230                 235                 240

Trp Val Ile Leu Val Val Thr Leu Val Val Pro Leu Leu Leu Val Ala
                245                 250                 255

Val Leu Ile Val Cys Cys Cys Ile Gly Ser Gly Cys Gly Gly Asp Pro
            260                 265                 270

Lys Cys Met Asp Arg Val Cys Phe Trp Arg Leu Gly Leu Leu Arg Gly
        275                 280                 285

Pro Gly Ala Glu Asp Asn Ala His Asn Glu Ile Leu Ser Asn Ala Asp
    290                 295                 300

Ser Leu Ser Thr Phe Val Ser Glu Gln Gln Met Glu Ser Gln Glu Pro
305                 310                 315                 320

Ala Asp Leu Thr Gly Val Thr Val Gln Ser Pro Gly Glu Ala Gln Cys
                325                 330                 335

Leu Leu Gly Pro Ala Glu Ala Glu Gly Ser Gln Arg Arg Arg Leu Leu
            340                 345                 350

Val Pro Ala Asn Gly Ala Asp Pro Thr Glu Thr Leu Met Leu Phe Phe
        355                 360                 365

Asp Lys Phe Ala Asn Ile Val Pro Phe Asp Ser Trp Asp Gln Leu Met
    370                 375                 380

Arg Gln Leu Asp Leu Thr Lys Asn Glu Ile Asp Val Val Arg Ala Gly
385                 390                 395                 400

Thr Ala Gly Pro Gly Asp Ala Leu Tyr Ala Met Leu Met Lys Trp Val
                405                 410                 415

Asn Lys Thr Gly Arg Asn Ala Ser Ile His Thr Leu Leu Asp Ala Leu
            420                 425                 430

Glu Arg Met Glu Glu Arg His Ala Lys Glu Lys Ile Gln Asp Leu Leu
        435                 440                 445

Val Asp Ser Gly Lys Phe Ile Tyr Leu Glu Asp Gly Thr Gly Ser Ala
    450                 455                 460

Val Ser Leu Glu
465

<210> SEQ ID NO 6
<211> LENGTH: 411
<212> TYPE: PRT
<213> ORGANISM: Homo sapiens

<400> SEQUENCE: 6
```

Met Gln Arg Gly Gln Asn Ala Pro Ala Ser Gly Ala Arg Lys
1               5                   10                  15

Arg His Gly Pro Gly Pro Arg Glu Ala Arg Gly Ala Arg Pro Gly Leu
                20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
                100                 105                 110

Cys Leu Arg Cys Thr Arg Cys Asp Ser Gly Glu Val Glu Leu Ser Pro
                115                 120                 125

Cys Thr Thr Thr Arg Asn Thr Val Cys Gln Cys Glu Glu Gly Thr Phe
    130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Ile Ile Gly Val Thr Val Ala
                180                 185                 190

Ala Val Val Leu Ile Val Ala Val Phe Val Cys Lys Ser Leu Leu Trp
    195                 200                 205

Lys Lys Val Leu Pro Tyr Leu Lys Gly Ile Cys Ser Gly Gly Gly Gly
210                 215                 220

Asp Pro Glu Arg Val Asp Arg Ser Ser Gln Arg Pro Gly Ala Glu Asp
225                 230                 235                 240

Asn Val Leu Asn Glu Ile Val Ser Ile Leu Gln Pro Thr Gln Val Pro
                245                 250                 255

Glu Gln Glu Met Glu Val Gln Glu Pro Ala Glu Pro Thr Gly Val Asn
                260                 265                 270

Met Leu Ser Pro Gly Glu Ser Glu His Leu Leu Glu Pro Ala Glu Ala
                275                 280                 285

Glu Arg Ser Gln Arg Arg Arg Leu Leu Val Pro Ala Asn Glu Gly Asp
                290                 295                 300

Pro Thr Glu Thr Leu Arg Gln Cys Phe Asp Asp Phe Ala Asp Leu Val
305                 310                 315                 320

Pro Phe Asp Ser Trp Glu Pro Leu Met Arg Lys Leu Gly Leu Met Asp
                325                 330                 335

Asn Glu Ile Lys Val Ala Lys Ala Glu Ala Ala Gly His Arg Asp Thr
                340                 345                 350

Leu Tyr Thr Met Leu Ile Lys Trp Val Asn Lys Thr Gly Arg Asp Ala
                355                 360                 365

Ser Val His Thr Leu Leu Asp Ala Leu Glu Thr Leu Gly Glu Arg Leu
                370                 375                 380

Ala Lys Gln Lys Ile Glu Asp His Leu Leu Ser Ser Gly Lys Phe Met
385                 390                 395                 400

Tyr Leu Glu Gly Asn Ala Asp Ser Ala Leu Ser
                405                 410

<210> SEQ ID NO 7

<211> LENGTH: 281
<212> TYPE: PRT
<213> ORGANISM: Homo sapiens

<400> SEQUENCE: 7

```
Met Ala Met Met Glu Val Gln Gly Gly Pro Ser Leu Gly Gln Thr Cys
 1               5                  10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280
```

<210> SEQ ID NO 8
<211> LENGTH: 335
<212> TYPE: PRT
<213> ORGANISM: Homo sapiens

<400> SEQUENCE: 8

```
Met Leu Gly Ile Trp Thr Leu Leu Pro Leu Val Leu Thr Ser Val Ala
 1               5                  10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60
```

```
Pro Gly Glu Arg Lys Ala Arg Asp Cys Thr Val Asn Gly Asp Glu Pro
 65                  70                  75                  80

Asp Cys Val Pro Cys Gln Glu Gly Lys Glu Tyr Thr Asp Lys Ala His
                 85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335

<210> SEQ ID NO 9
<211> LENGTH: 281
<212> TYPE: PRT
<213> ORGANISM: Homo sapiens

<400> SEQUENCE: 9

Met Gln Gln Pro Phe Asn Tyr Pro Tyr Pro Gln Ile Tyr Trp Val Asp
  1               5                  10                  15

Ser Ser Ala Ser Ser Pro Trp Ala Pro Pro Gly Thr Val Leu Pro Cys
             20                  25                  30

Pro Thr Ser Val Pro Arg Arg Pro Gly Gln Arg Arg Pro Pro Pro Pro
         35                  40                  45

Pro Pro Pro Pro Pro Leu Pro Pro Pro Pro Pro Pro Leu Pro
     50                  55                  60

Pro Leu Pro Leu Pro Pro Leu Lys Lys Arg Gly Asn His Ser Thr Gly
 65                  70                  75                  80

Leu Cys Leu Leu Val Met Phe Phe Met Val Leu Val Ala Leu Val Gly
             85                  90                  95

Leu Gly Leu Gly Met Phe Gln Leu Phe His Leu Gln Lys Glu Leu Ala
            100                 105                 110
```

-continued

```
Glu Leu Arg Glu Ser Thr Ser Gln Met His Thr Ala Ser Ser Leu Glu
        115                 120                 125
Lys Gln Ile Gly His Pro Ser Pro Pro Glu Lys Lys Glu Leu Arg
        130                 135                 140
Lys Val Ala His Leu Thr Gly Lys Ser Asn Ser Arg Ser Met Pro Leu
145                 150                 155                 160
Glu Trp Glu Asp Thr Tyr Gly Ile Val Leu Leu Ser Gly Val Lys Tyr
                165                 170                 175
Lys Lys Gly Gly Leu Val Ile Asn Glu Thr Gly Leu Tyr Phe Val Tyr
            180                 185                 190
Ser Lys Val Tyr Phe Arg Gly Gln Ser Cys Asn Asn Leu Pro Leu Ser
        195                 200                 205
His Lys Val Tyr Met Arg Asn Ser Lys Tyr Pro Gln Asp Leu Val Met
    210                 215                 220
Met Glu Gly Lys Met Met Ser Tyr Cys Thr Thr Gly Gln Met Trp Ala
225                 230                 235                 240
Arg Ser Ser Tyr Leu Gly Ala Val Phe Asn Leu Thr Ser Ala Asp His
                245                 250                 255
Leu Tyr Val Asn Val Ser Glu Leu Ser Leu Val Asn Phe Glu Glu Ser
            260                 265                 270
Gln Thr Phe Phe Gly Leu Tyr Lys Leu
        275                 280
```